US008043343B2

(12) United States Patent  (10) Patent No.: US 8,043,343 B2
Miller et al.  (45) Date of Patent: Oct. 25, 2011

(54) STABILIZATION SYSTEM AND METHOD

(75) Inventors: Peter Thomas Miller, Austin, TX (US); Brian J. Bergeron, Austin, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 455 days.

(21) Appl. No.: 11/770,366

(22) Filed: Jun. 28, 2007

(65) Prior Publication Data
US 2009/0005814 A1  Jan. 1, 2009

(51) Int. Cl.
*A61B 17/70* (2006.01)
(52) U.S. Cl. ............ 606/279; 606/246; 606/914
(58) Field of Classification Search ............ 606/60, 606/246, 250–279, 86 A, 86 B, 86 R, 99, 606/103, 104, 914
See application file for complete search history.

(56) References Cited

U.S. PATENT DOCUMENTS

| | | | |
|---|---|---|---|
| 5,496,322 A | 3/1996 | Mathews | |
| 6,520,907 B1 | 2/2003 | Foley et al. | |
| 6,723,096 B1 * | 4/2004 | Dorchak et al. | 606/86 A |
| 6,746,487 B2 * | 6/2004 | Scifert et al. | 623/22.12 |
| 6,755,790 B2 | 6/2004 | Stewart et al. | |
| 6,929,606 B2 | 8/2005 | Ritland | |
| 7,396,360 B2 * | 7/2008 | Lieberman | 606/247 |
| 7,465,306 B2 * | 12/2008 | Pond et al. | 606/86 A |
| 7,497,869 B2 | 3/2009 | Justis | |
| 2002/0000227 A1 | 1/2002 | Duyke et al. | |
| 2003/0208203 A1 * | 11/2003 | Lim et al. | 606/61 |
| 2004/0039384 A1 * | 2/2004 | Boehm et al. | 606/61 |
| 2004/0073110 A1 | 4/2004 | Stewart et al. | |
| 2004/0143265 A1 | 7/2004 | Landry et al. | |
| 2005/0065517 A1 * | 3/2005 | Chin | 606/61 |
| 2005/0080418 A1 * | 4/2005 | Simonson et al. | 606/61 |
| 2005/0085813 A1 * | 4/2005 | Spitler et al. | 606/61 |
| 2005/0131421 A1 * | 6/2005 | Anderson et al. | 606/99 |
| 2005/0154389 A1 | 7/2005 | Selover et al. | |
| 2005/0192579 A1 * | 9/2005 | Jackson | 606/72 |
| 2005/0245928 A1 * | 11/2005 | Colleran et al. | 606/61 |
| 2005/0251192 A1 * | 11/2005 | Shluzas et al. | 606/191 |
| 2005/0256525 A1 | 11/2005 | Culbert et al. | |
| 2006/0009777 A1 * | 1/2006 | Lim et al. | 606/90 |
| 2006/0030872 A1 | 2/2006 | Culbert et al. | |
| 2006/0036240 A1 | 2/2006 | Colleran et al. | |
| 2006/0036244 A1 | 2/2006 | Spitler et al. | |
| 2006/0036255 A1 | 2/2006 | Pond, Jr. et al. | |
| 2006/0069404 A1 | 3/2006 | Shluzas et al. | |
| 2006/0074445 A1 | 4/2006 | Gerber | |
| 2006/0084993 A1 | 4/2006 | Landry et al. | |

(Continued)

FOREIGN PATENT DOCUMENTS
WO  WO 2006091863 A2 *  8/2006

*Primary Examiner* — Eduardo C Robert
*Assistant Examiner* — Jerry Cumberledge
(74) *Attorney, Agent, or Firm* — Seager Tufte Wickhem LLC

(57) ABSTRACT

The disclosure relates generally to embodiments of systems and methods of spinal stabilization. Embodiments include methods that use a dilator to displace tissue proximate to a sleeve. An embodiment of a surgical system can comprise a dilator that may define a working channel from a first opening to a second opening. The dilator can be positioned to displace tissue proximate to the sleeve. The dilator may be shaped to allow a first end of an elongated member to enter the working channel through the first opening and exit the dilator through the second opening to be percutaneously moved to another assembly.

22 Claims, 61 Drawing Sheets

U.S. PATENT DOCUMENTS

| | | |
|---|---|---|
| 2006/0106394 A1 | 5/2006 | Colleran |
| 2006/0111713 A1* | 5/2006 | Jackson .......................... 606/61 |
| 2006/0189997 A1* | 8/2006 | Guenther et al. ............... 606/88 |
| 2006/0200139 A1 | 9/2006 | Michelson |
| 2006/0235391 A1 | 10/2006 | Sutterlin, III |
| 2006/0247630 A1* | 11/2006 | Iott et al. ........................ 606/61 |
| 2006/0293693 A1* | 12/2006 | Farr et al. ...................... 606/104 |
| 2007/0016219 A1 | 1/2007 | Levine |
| 2007/0055247 A1 | 3/2007 | Jahng |
| 2007/0073290 A1 | 3/2007 | Boehm, Jr. |
| 2007/0078460 A1 | 4/2007 | Frigg et al. |
| 2007/0078461 A1 | 4/2007 | Shluzas |
| 2007/0083210 A1 | 4/2007 | Hestad et al. |
| 2007/0100341 A1 | 5/2007 | Reglos et al. |
| 2007/0191836 A1* | 8/2007 | Justis .............................. 606/61 |
| 2007/0219553 A1* | 9/2007 | Chappuis ........................ 606/61 |
| 2007/0270842 A1* | 11/2007 | Bankoski et al. ............... 606/61 |
| 2008/0009678 A1* | 1/2008 | Ritland .......................... 600/201 |
| 2008/0015582 A1* | 1/2008 | DiPoto et al. ................... 606/61 |
| 2008/0065072 A1* | 3/2008 | Spitler et al. ................... 606/61 |
| 2008/0114403 A1* | 5/2008 | Kuester et al. ................ 606/308 |
| 2008/0125788 A1* | 5/2008 | Cohen et al. .................. 606/104 |
| 2008/0140120 A1* | 6/2008 | Hestad et al. ................. 606/246 |
| 2008/0140132 A1* | 6/2008 | Perez-Cruet .................. 606/301 |
| 2008/0312703 A1* | 12/2008 | Hestad et al. ............... 606/86 A |
| 2009/0143829 A1* | 6/2009 | Shluzas ....................... 606/86 A |

* cited by examiner

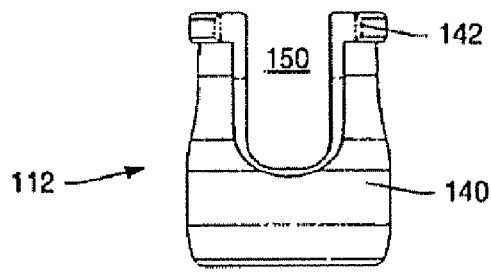
FIG. 9A
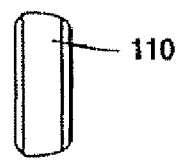
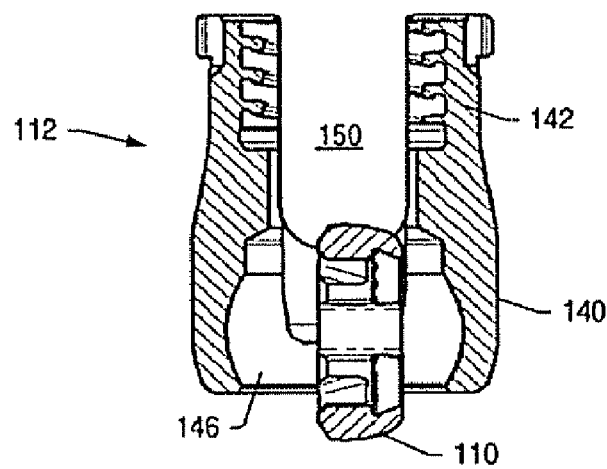
FIG. 9B
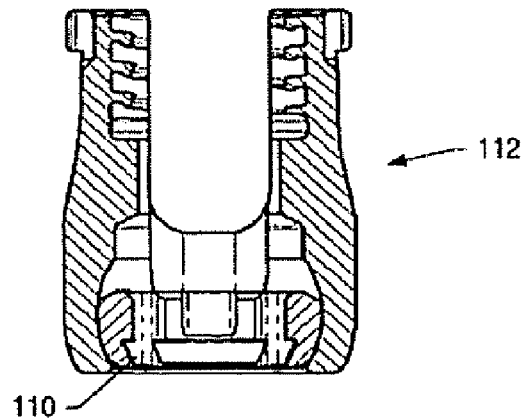
FIG. 9C

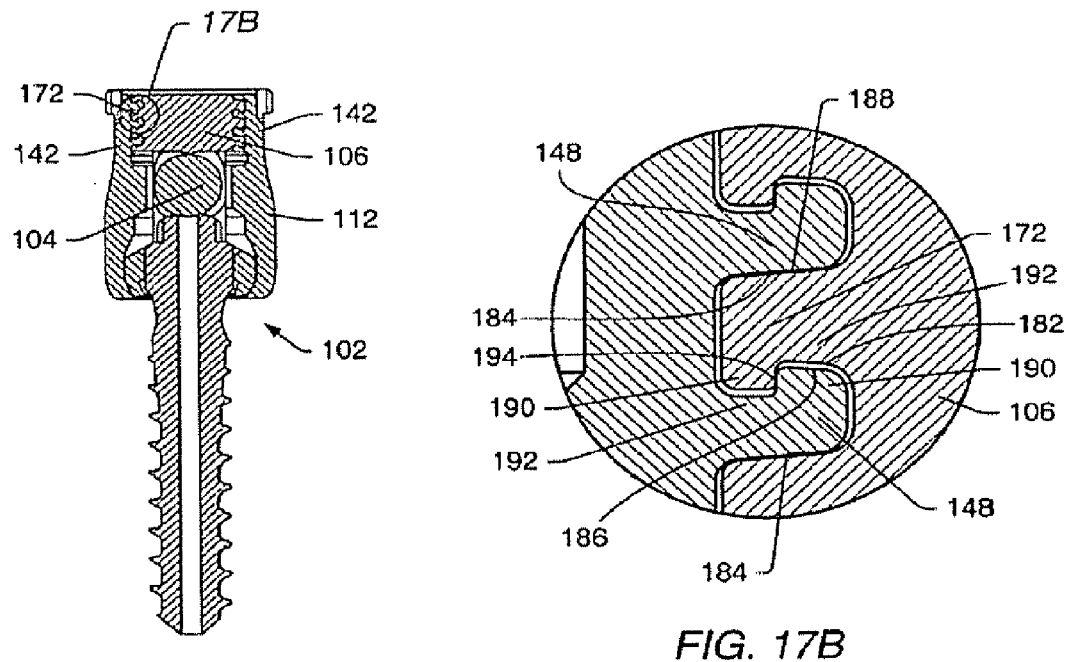
FIG. 17A
FIG. 17B
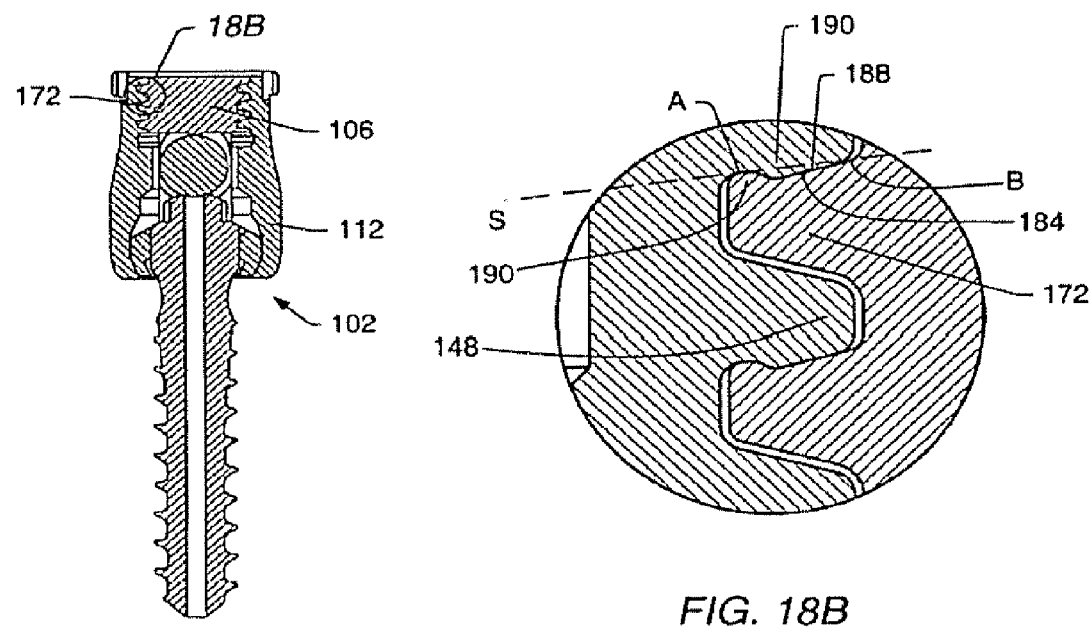
FIG. 18A
FIG. 18B

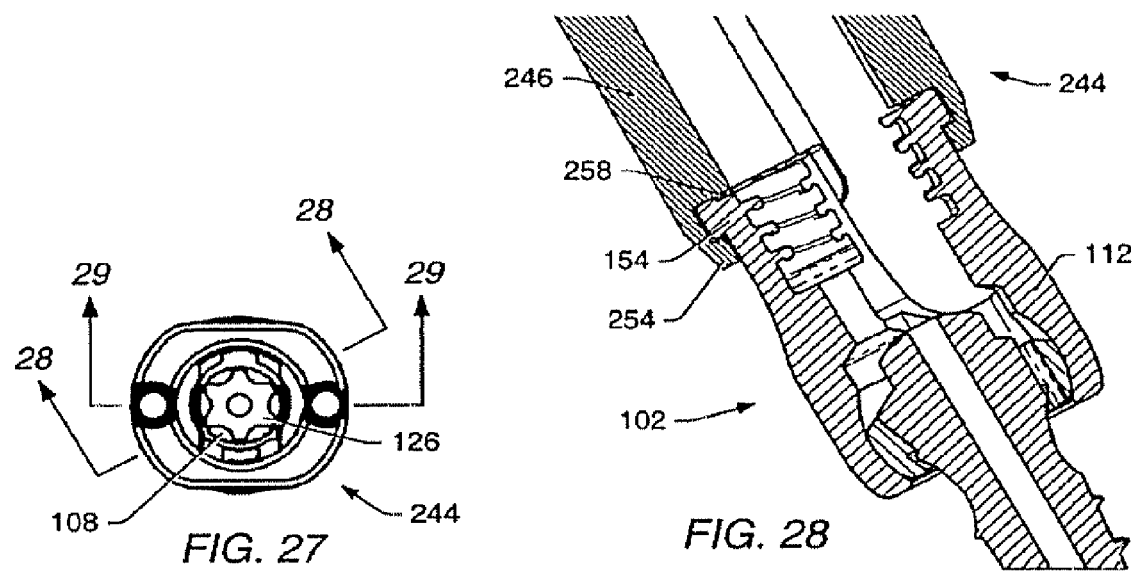
FIG. 27
FIG. 28
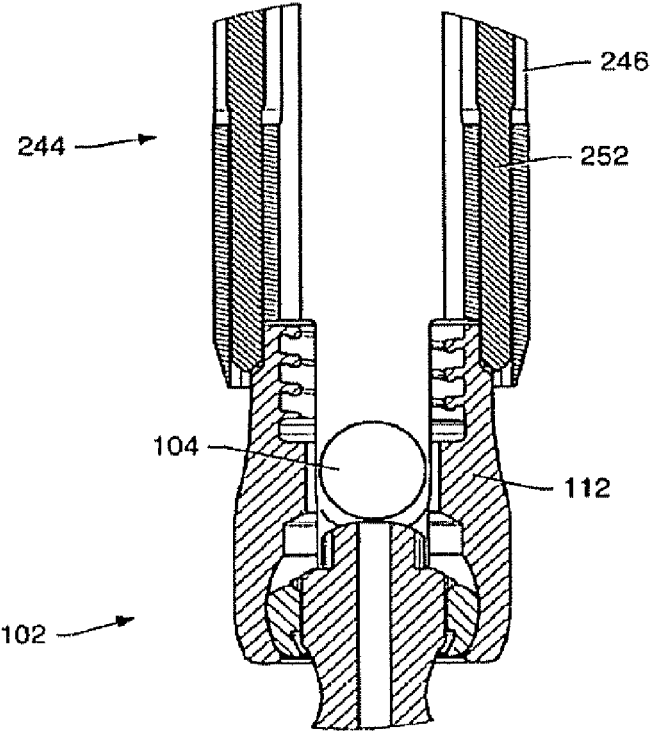
FIG. 29

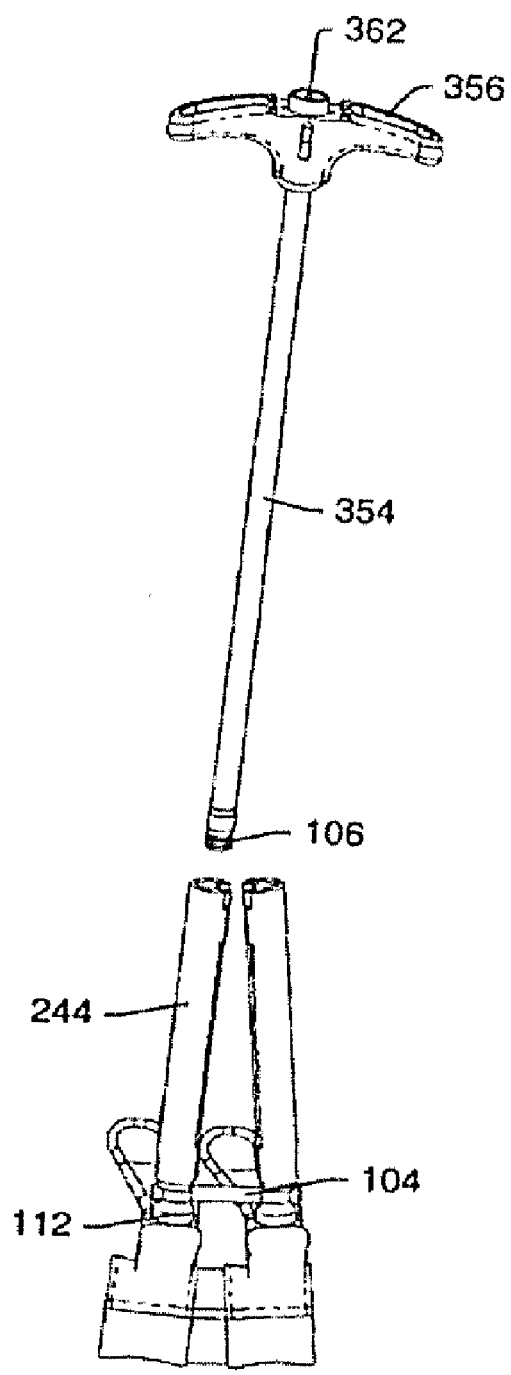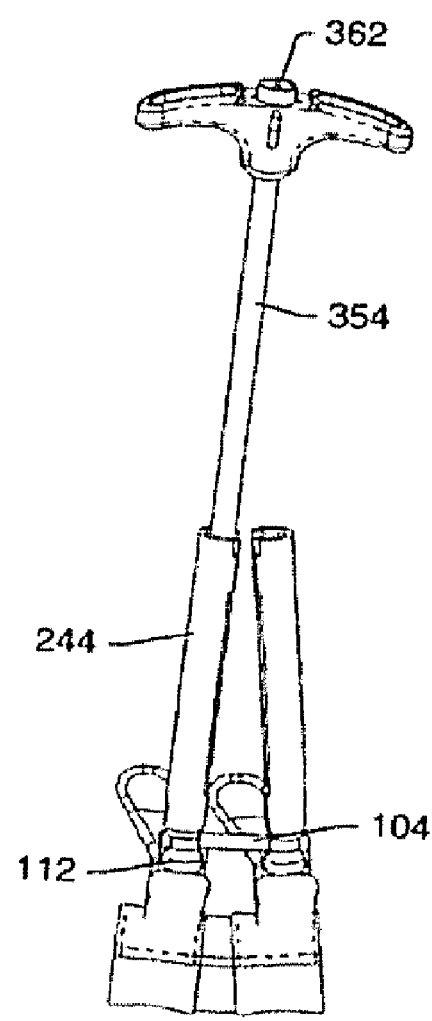
FIG. 60A
FIG. 60B

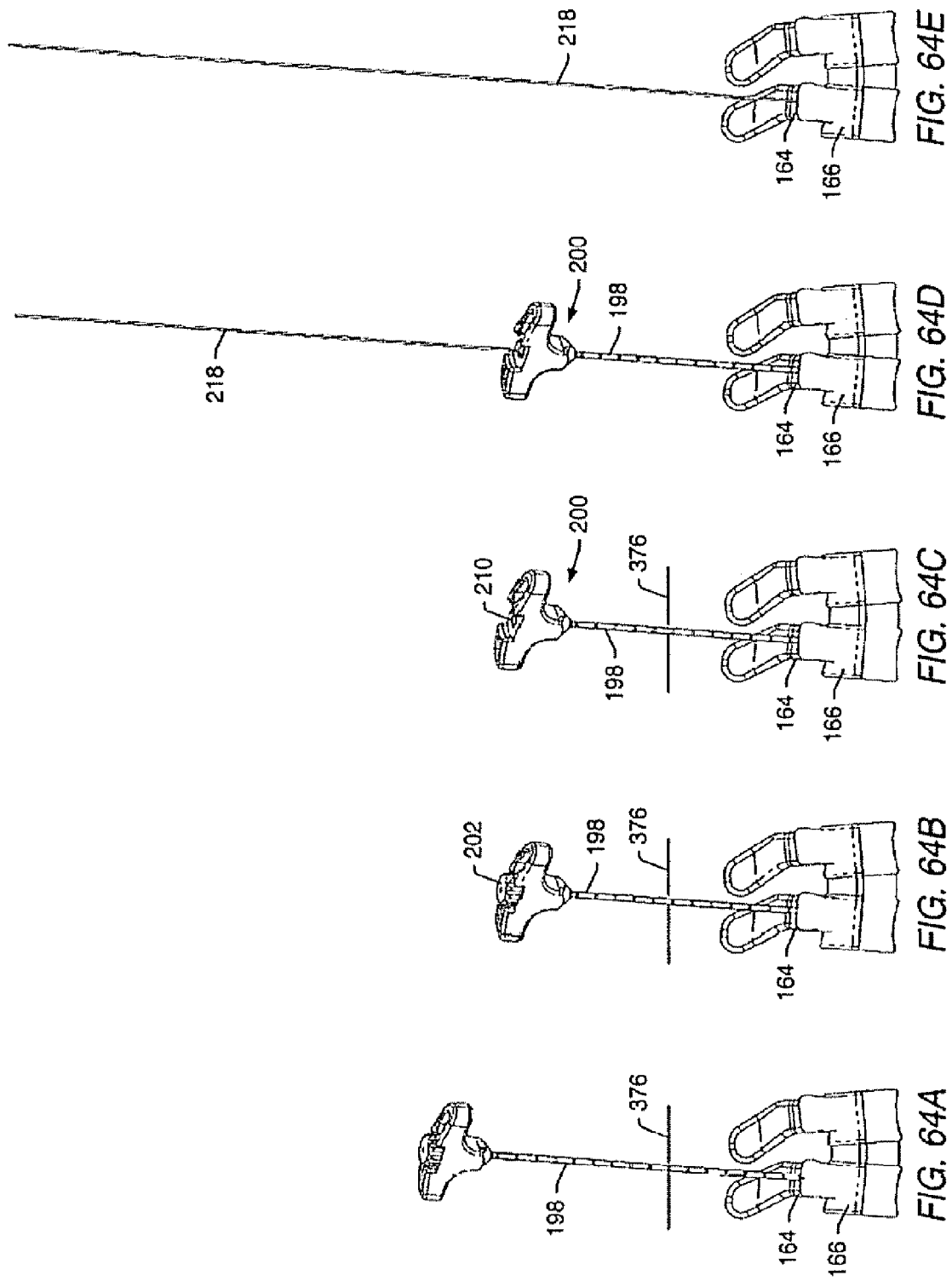

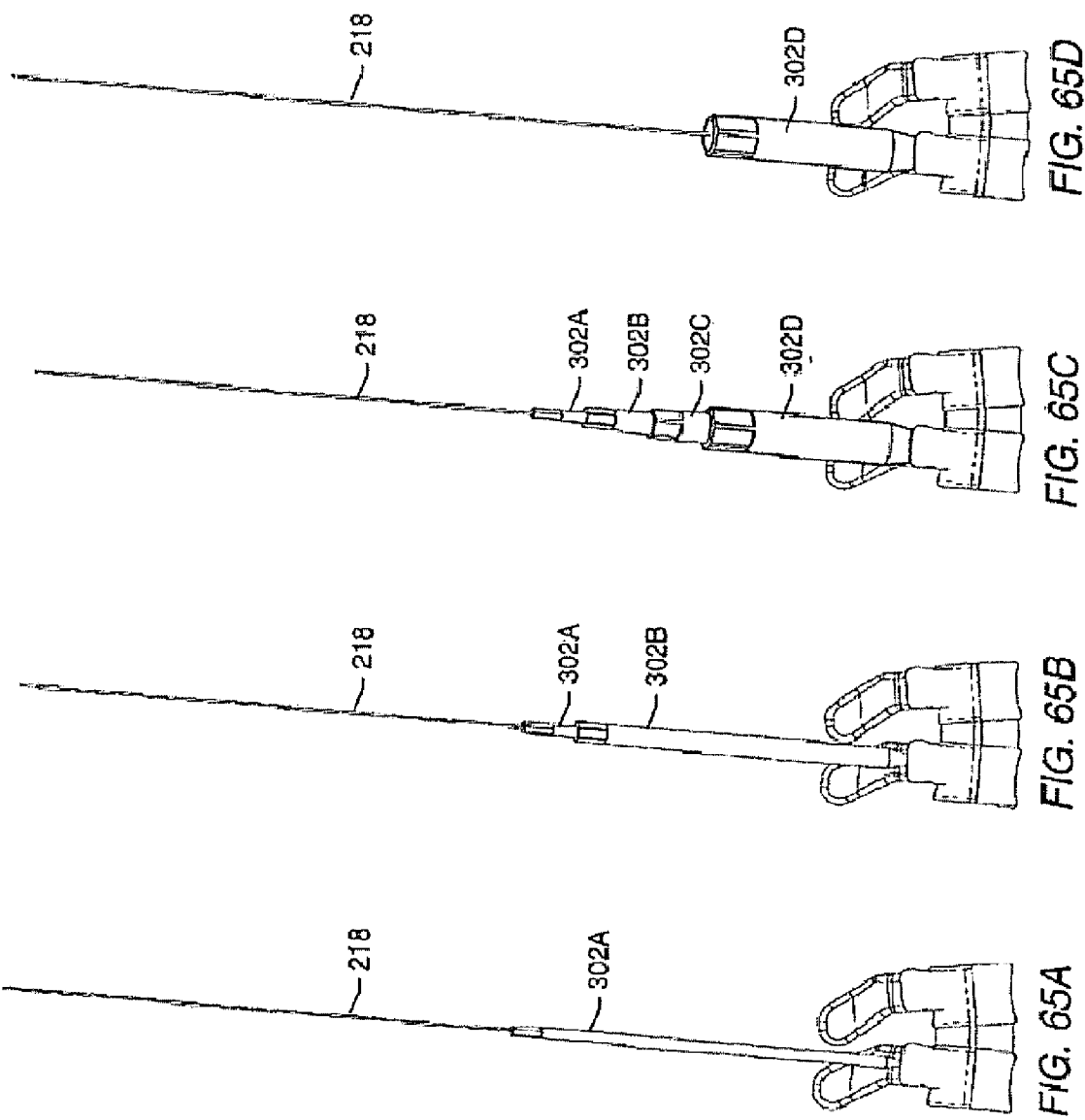

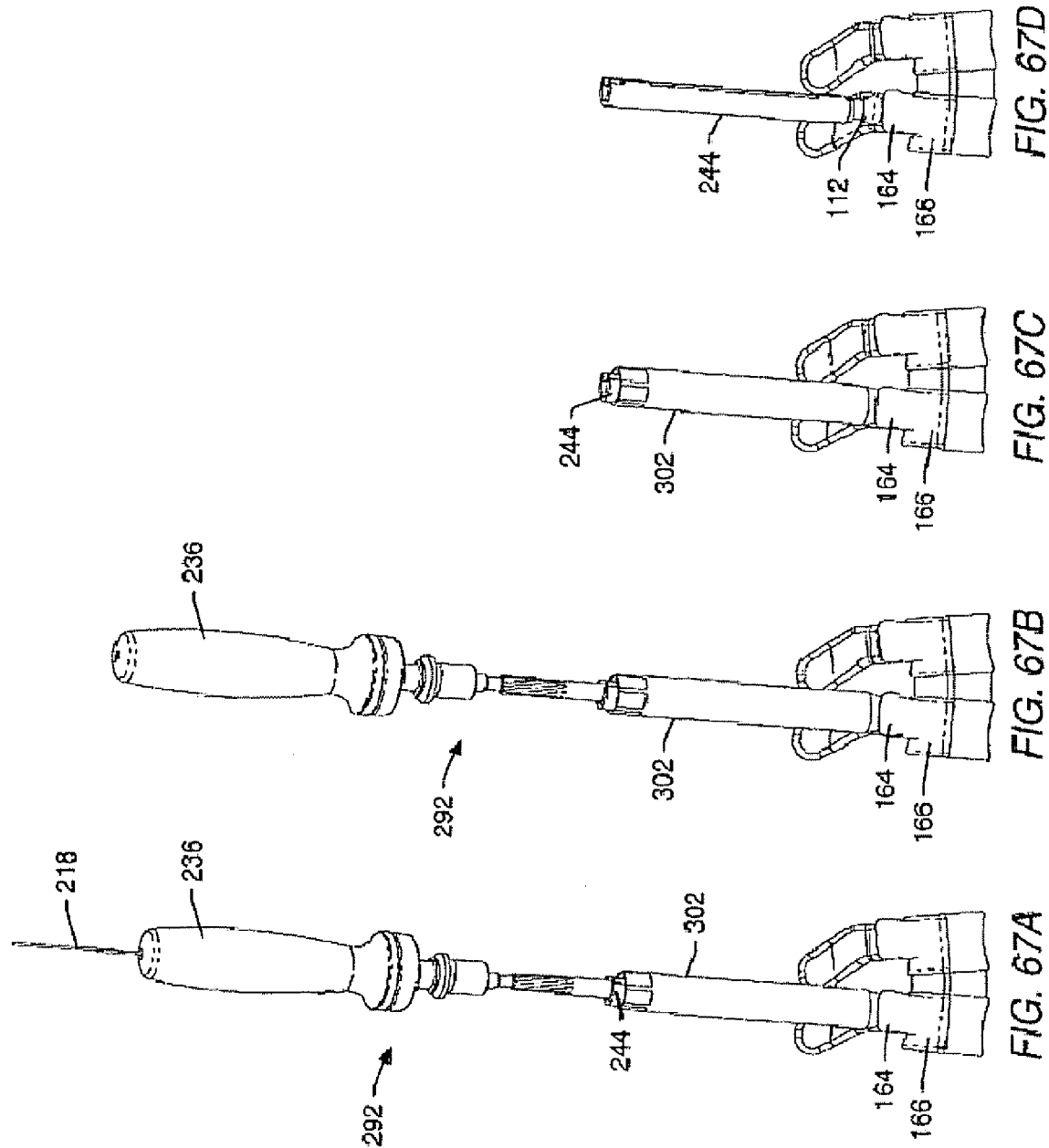

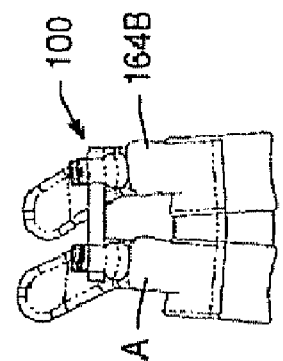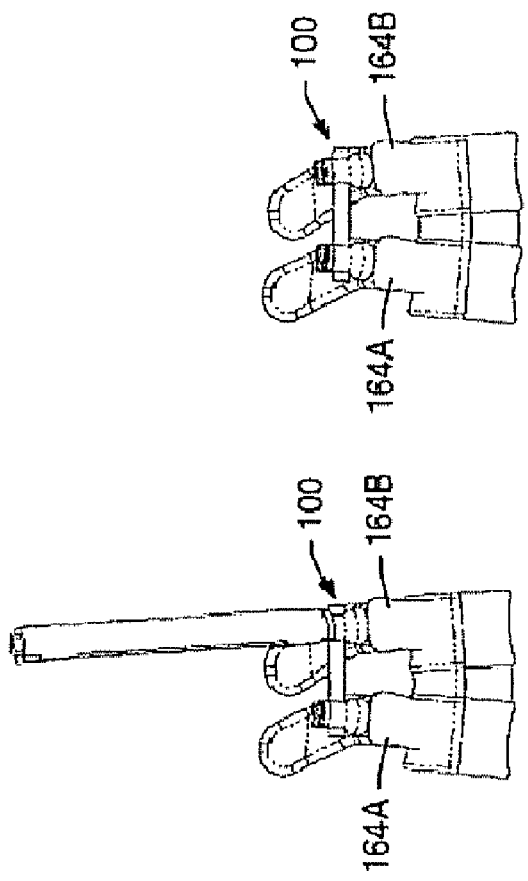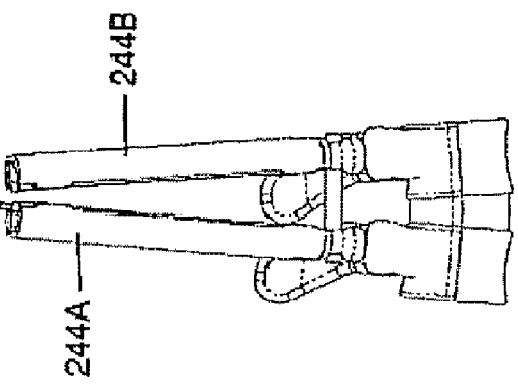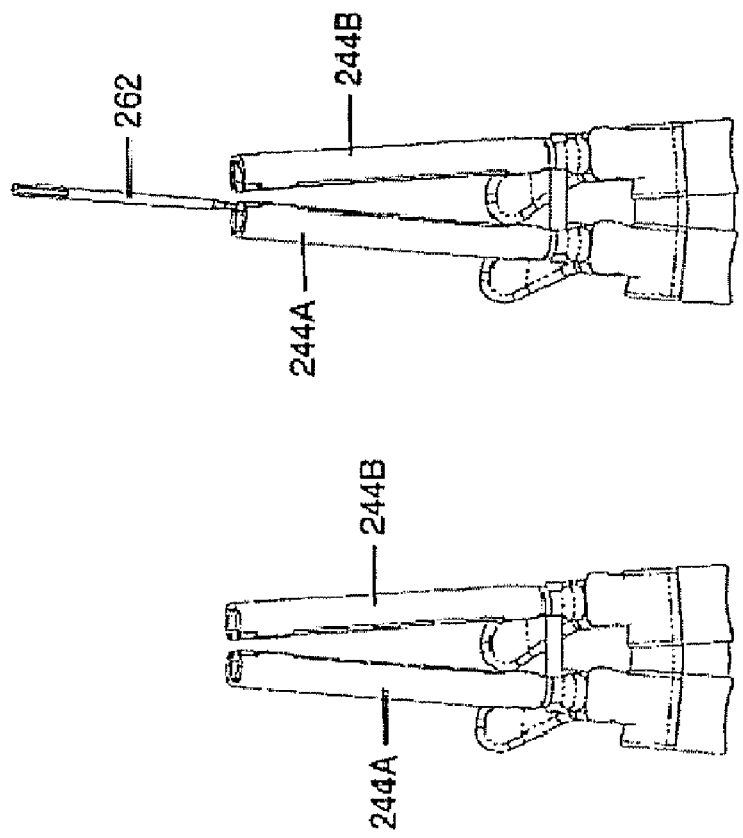

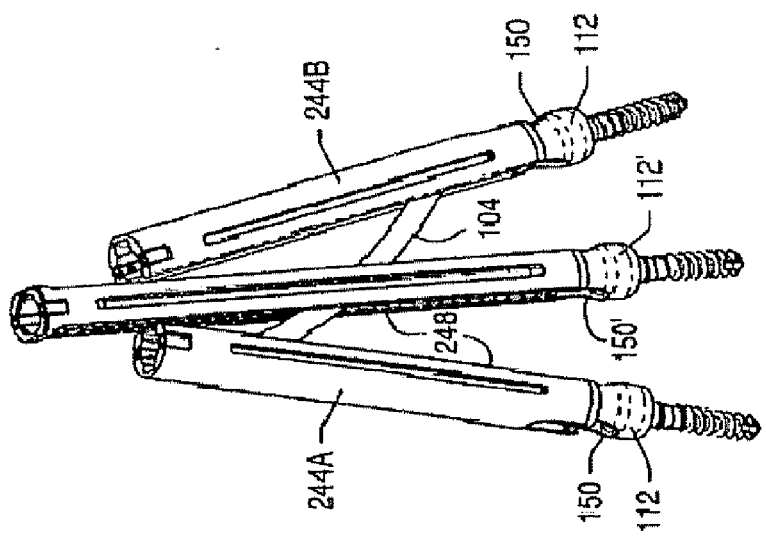
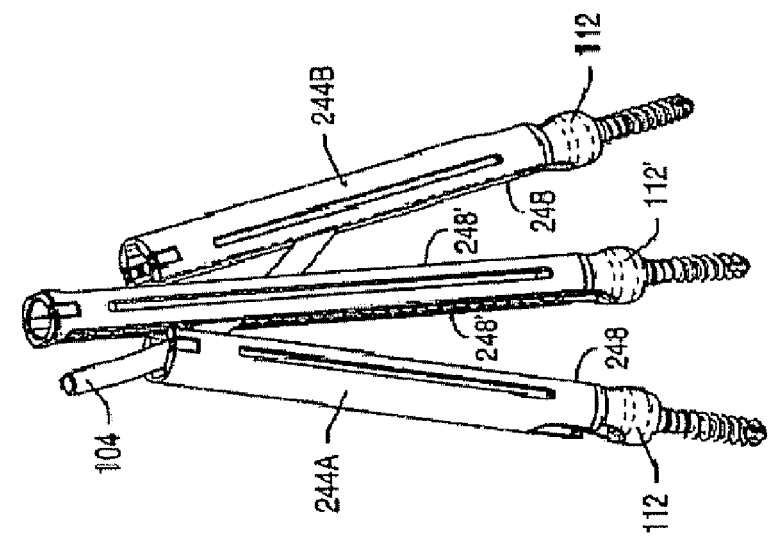
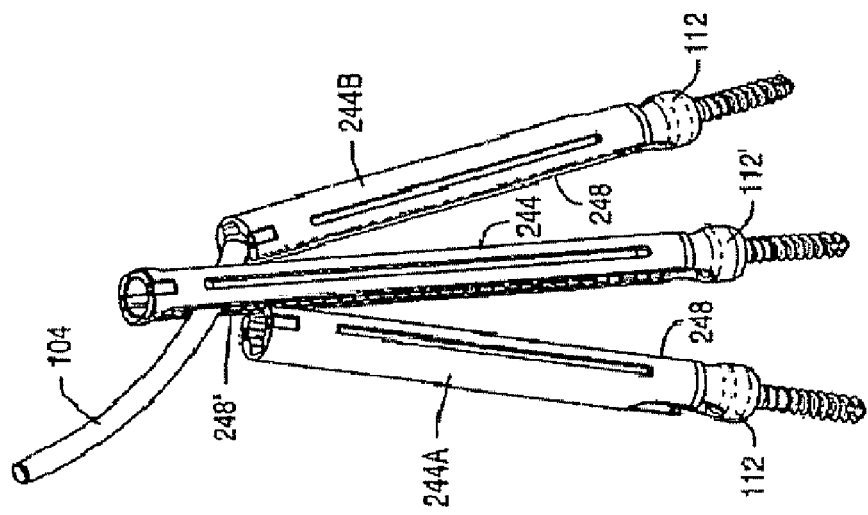

STABILIZATION SYSTEM AND METHOD

TECHNICAL FIELD OF THE DISCLOSURE

The disclosure describes various spinal stabilization systems and methods, including systems and methods for inserting spinal stabilization rods in minimally invasive surgery.

BACKGROUND OF THE DISCLOSURE

Bone may be subject to degeneration caused by trauma, disease, and/or aging. Degeneration may destabilize bone and affect surrounding structures. For example, destabilization of a spine may result in alteration of a natural spacing between adjacent vertebrae. Alteration of a natural spacing between adjacent vertebrae may subject nerves that pass between vertebral bodies to pressure. Pressure applied to the nerves may cause pain and/or nerve damage. Maintaining the natural spacing between vertebrae may reduce pressure applied to nerves that pass between vertebral bodies. A spinal stabilization procedure may be used to maintain the natural spacing between vertebrae and promote spinal stability. Spinal stabilization may involve accessing a portion of the spine through soft tissue. Conventional stabilization systems may require a large incision and/or multiple incisions in the soft tissue to provide access to a portion of the spine to be stabilized. Conventional procedures may result in trauma to the soft tissue, for example, due to muscle stripping. Spinal stabilization systems for a lumbar region of the spine may be inserted during a spinal stabilization procedure using a posterior spinal approach. Conventional systems and methods for posterolateral spinal fusion may involve dissecting and retracting soft tissue proximate the surgical site. Dissection and retraction of soft tissue may cause trauma to the soft tissue, and extend recovery time. Minimally invasive procedures and systems may reduce recovery time as well as trauma to the soft tissue surrounding a stabilization site.

SUMMARY OF THE DISCLOSURE

The disclosure describes embodiments of systems and methods for spinal stabilization, particularly systems and methods that utilize a shaped dilator to deliver, preferably percutaneously, an elongated member so that a portion of the elongated member can be seated in a collar of a bone fastener assembly. According to one embodiment, a surgeon can form a first assembly and a second assembly. The first assembly can comprise a first bone fastener, a first collar, and a first sleeve wherein the first bone fastener is fastened to a first vertebra. The second assembly can comprise a second bone fastener, a second collar, a second sleeve. The surgeon can position a dilator in an incision through which the first assembly enters a patient to displace tissue proximate to the first sleeve. The dilator can comprise a first opening, a second opening and a working channel running from the first opening to the second opening. The surgeon can move at least a first portion of an elongated member into the working channel, through the first assembly and to the second assembly. The surgeon can further seat the first portion of the elongated member in the second collar and seat a second portion of the elongated member in the first collar. Preferably, the first portion of the elongated member is moved percutaneously to the second collar.

Another embodiment can include a surgical system comprising a first assembly and a dilator. The first assembly can comprise a bone fastener coupled to a vertebra, a collar coupled to the bone fastener said collar comprising a slot for seating an elongated member, and a sleeve coupled to the collar. The dilator can define a working channel from a first opening to a second opening. The dilator can be positioned to displace tissue proximate to the sleeve. According to an embodiment of the dilator, the dilator is shaped to allow a first end of the elongated member to enter the working channel through the first opening and exit the dilator through the second opening to be percutaneously moved to another assembly.

Another embodiment can include a tissue dilator comprising a first wall configured to be approximately parallel to a sleeve of a spinal stabilization system during use and a second wall disposed at an angle to the first wall. The tissue dilator defines a working channel from a first opening to a second opening. Furthermore the tissue dilator is shaped so that when the dilator is in position proximate to a first sleeve-collar assembly, a portion of an elongated member can enter the working channel through the first opening and exit the dilator through the second opening to be percutaneously moved to a second sleeve-collar assembly.

One advantage provided by various embodiments of the spinal stabilization system and method disclosed herein is that a spinal rod can be installed percutaneously without requiring additional incisions in the patient.

Another advantage provided by embodiments of the spinal stabilization system and method disclosed herein is that a spinal rod is not confined to a fixed arc during insertion.

Yet another advantage provided by embodiments of the spinal stabilization system and method disclosed herein is that the additional components used for percutaneous delivery of a spinal rod are generally easy to place and use.

BRIEF DESCRIPTION OF THE FIGURES

Advantages of the embodiments will become apparent to those skilled in the art with the benefit of the following detailed description and upon reference to the accompanying drawings in which:

FIGS. 9A-9C depict schematic views of a method of positioning a ring in a collar of a bone fastener assembly.

FIG. 17A depicts a cross-sectional representation of an embodiment of a spinal stabilization system.

FIG. 17B depicts a detailed view of a portion of FIG. 17A.

FIG. 18A depicts a cross-sectional representation of an embodiment of a spinal stabilization system.

FIG. 18B depicts a detailed view of a portion of FIG. 18A.

FIG. 27 depicts a top view of an embodiment of a multi-channel sleeve with a bone fastener assembly coupled to the sleeve.

FIG. 28 depicts a cross-sectional representation of a portion of the sleeve with the bone fastener assembly taken substantially along line 28-28 of FIG. 27.

FIG. 29 depicts a cross-sectional representation of a portion of the sleeve with the bone fastener assembly taken substantially along line 29-29 of FIG. 27.

FIGS. 60A and 60B depict perspective views of a tool designed to position a closure member in a collar coupled to a bone fastener.

FIGS. 64A-64E depict schematic views of guide wire placement during a minimally invasive spinal stabilization procedure.

FIGS. 65A-65D depict schematic views of tissue dilation during a minimally invasive spinal stabilization procedure.

FIGS. 67A-67D depict schematic views of insertion of a sleeve and bone fastener assembly during a minimally invasive spinal stabilization procedure.

FIGS. 78A-78D depict schematic views of a sleeve removal during a minimally invasive spinal stabilization procedure.

FIGS. 79A-79E depict schematic views of elongated member placement in sleeves for a multi-level spinal stabilization system.

Figure 1:
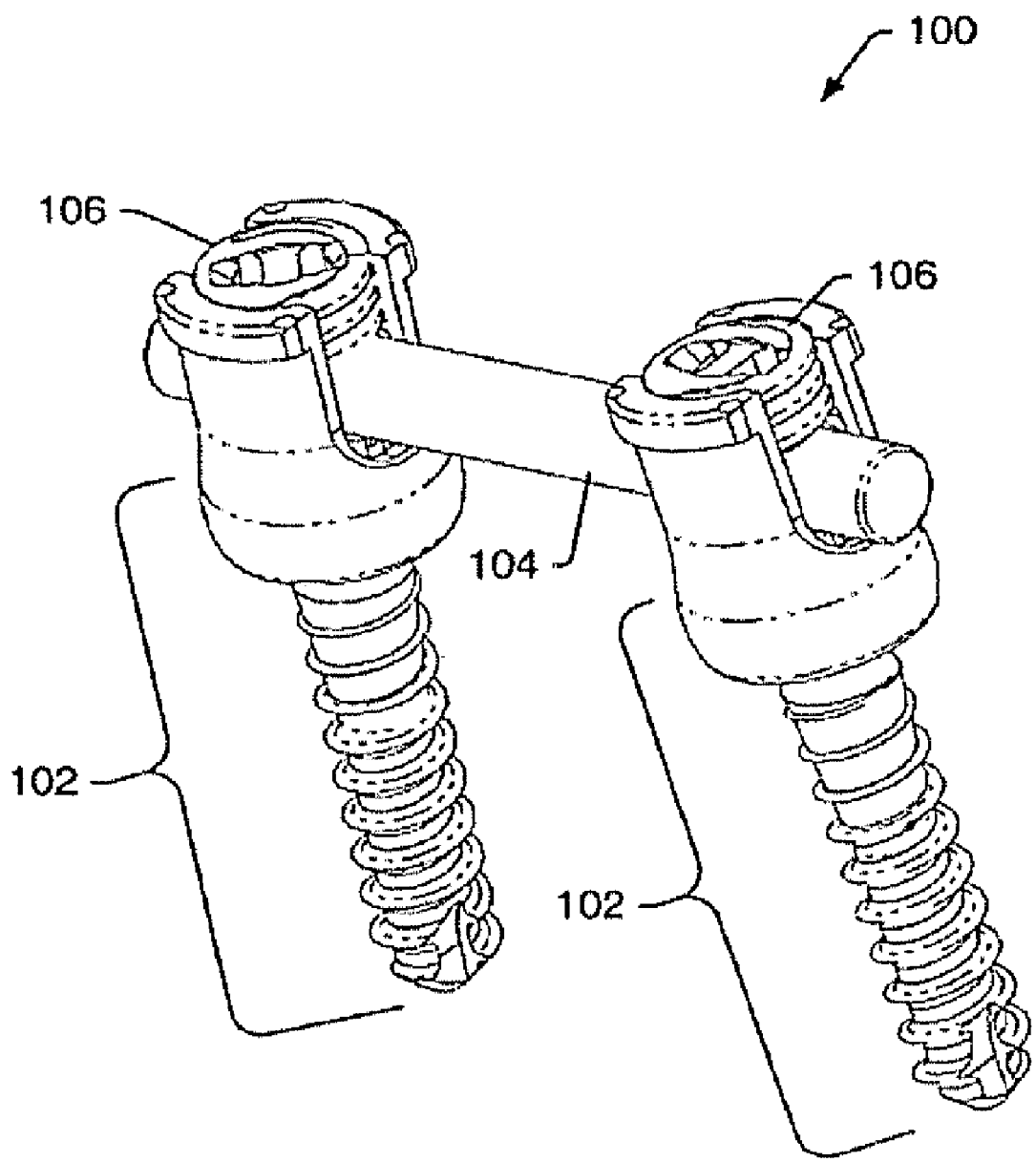
FIG. 1 depicts a perspective view of an embodiment of a spinal stabilization system.

Specific embodiments are shown by way of example in the drawings and will herein be described in detail. The drawings may not be to scale. It should be understood that the drawings and detailed description thereto are not intended to limit the embodiments to the particular form disclosed.

DETAILED DESCRIPTION OF THE DISCLOSURE

A spinal stabilization system may be installed in a patient to stabilize a portion of a spine. Spinal stabilization may be used, but is not limited to use, in patients having degenerative disc disease, spinal stenosis, spondylolisthesis, pseudoarthrosis, and/or spinal deformities; in patients having fracture or other vertebral trauma; and in patients after tumor resection. A spinal stabilization system may be installed using a minimally invasive procedure. An instrumentation set may include instruments and spinal stabilization system components for forming a spinal stabilization system in a patient.

A minimally invasive procedure may be used to limit an amount of trauma to soft tissue surrounding vertebrae that are to be stabilized. Particularly, a procedure may be used to percutaneously deliver a spinal rod. In some embodiments, the natural flexibility of skin and soft tissue may be used to limit the length and/or depth of an incision or incisions needed during the stabilization procedure. Minimally invasive procedures may provide limited direct visibility in vivo. Forming a spinal stabilization system using a minimally invasive procedure may include using tools to position system components in the body. A minimally invasive procedure may be performed after installation of one or more spinal implants in a patient. The spinal implant or spinal implants may be inserted using an anterior procedure and/or a lateral procedure. The patient may be turned and a minimally invasive procedure may be used to install a posterior spinal stabilization system. A minimally invasive procedure for stabilizing the spine may be performed without prior insertion of one or more spinal implants in some patients. In some patients, a minimally invasive procedure may be used to install a spinal stabilization system after one or more spinal implants are inserted using a posterior spinal approach. A spinal stabilization system may be used to achieve rigid pedicle fixation while minimizing the amount of damage to surrounding tissue. In some embodiments, a spinal stabilization system may be used to provide stability to two adjacent vertebrae (i.e., one vertebral level). A spinal stabilization system may include two bone fastener assemblies. One bone fastener assembly may be positioned in each of the vertebrae to be stabilized. An elongated member may be coupled and secured to the bone fastener assemblies. As used herein, "coupled" components may directly contact each other or may be separated by one or more intervening members. In some embodiments, a single spinal stabilization system may be installed in a patient. Such a system may be referred to as a unilateral, single-level stabilization system or a single-level, two-point stabilization system. In some embodiments, two spinal stabilization systems may be installed in a patient on opposite sides of a spine. Such a system may be referred to as a bilateral, single-level stabilization system or a single-level, four-point stabilization system.

In some embodiments, a spinal stabilization system may provide stability to three or more vertebrae (i.e., two or more vertebral levels). In a two vertebral level spinal stabilization system, the spinal stabilization system may include three bone fastener assemblies. One bone fastener assembly may be positioned in each of the vertebrae to be stabilized. An elongated member may be coupled and secured to the three bone fastener assemblies. In some embodiments, a single two-level spinal stabilization system may be installed in a patient. Such a system may be referred to as a unilateral, two-level stabilization system or a two-level, three-point stabilization system. In some embodiments, two three-point spinal stabilization systems may be installed in a patient on opposite sides of a spine. Such a system may be referred to as a bilateral, two-level stabilization system or a two-level, six-point stabilization system. In some embodiments, combination systems may be installed. For example, a two-point stabilization system may be installed on one side of a spine, and a three-point stabilization system may be installed on the opposite side of the spine. The composite system may be referred to a five-point stabilization system. Minimally invasive procedures may reduce trauma to soft tissue surrounding vertebrae that are to be stabilized. Only a small opening may need to be made in a patient. For example, for a single-level stabilization procedure on one side of the spine, the surgical procedure may be performed through a 2 cm to 4 cm incision formed in the skin of the patient.

Figure 2:
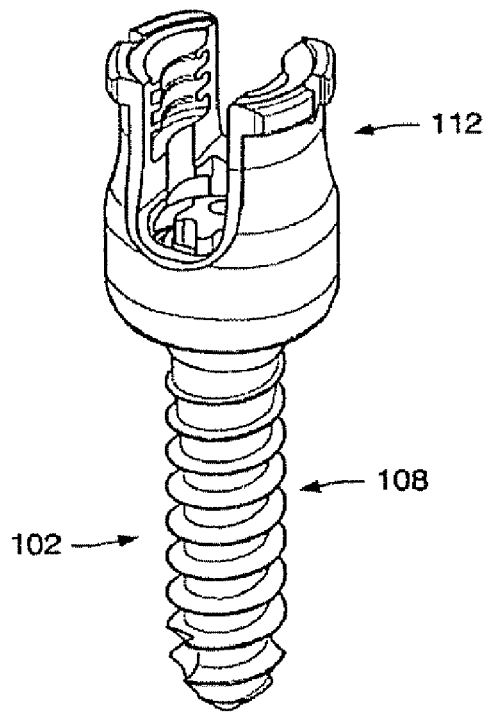
FIG. 2 depicts a perspective view of an embodiment of a bone fastener assembly.

Components of spinal stabilization systems may be made of materials including, but not limited to, titanium, titanium alloys, stainless steel, ceramics, and/or polymers. Some components of a spinal stabilization system may be autoclaved and/or chemically sterilized. Components that may not be autoclaved and/or chemically sterilized may be made of sterile materials. Components made of sterile materials may be placed in working relation to other sterile components during assembly of a spinal stabilization system. Spinal stabilization systems may be used to correct problems in lumbar, thoracic, and/or cervical portions of a spine. Various embodiments of a spinal stabilization system may be used from the C1 vertebra to the sacrum. For example, a spinal stabilization system may be implanted posterior to the spine to maintain distraction between adjacent vertebral bodies in a lumbar portion of the spine. FIG. 1 depicts an embodiment of spinal stabilization system that may be implanted using a minimally invasive surgical procedure. Spinal stabilization system 100 may include bone fastener assemblies 102, elongated member 104, and/or closure members 106. Other spinal stabilization system embodiments may include, but are not limited to, plates, dumbbell-shaped members, and/or transverse connectors. FIG. 1 depicts a spinal stabilization system for one vertebral level. In some embodiments, the spinal stabilization system of FIG. 1 may be used as a multi-level spinal stabilization system if one or more vertebrae are located between the vertebrae in which bone fastener assemblies 102 are placed. In other embodiments, multi-level spinal stabilization systems may include additional bone fastener assemblies to couple to one or more other vertebrae. FIG. 2 depicts a perspective view of bone fastener assembly 102. FIG. 3, FIGS. 4A and 4B, and FIG. 5 depict embodiments of bone fastener assembly components. Components of bone fastener assembly 102 may include, but are not limited to, bone fastener 108 (shown in FIG. 3), ring 110 (shown in FIGS. 4A and 4B), and collar 112 (shown in FIG. 5). Bone fastener 108 may couple bone fastener assembly 102 to a vertebra. Ring 110 may be positioned between a head of bone fastener 108 and collar 112.

Figure 3:
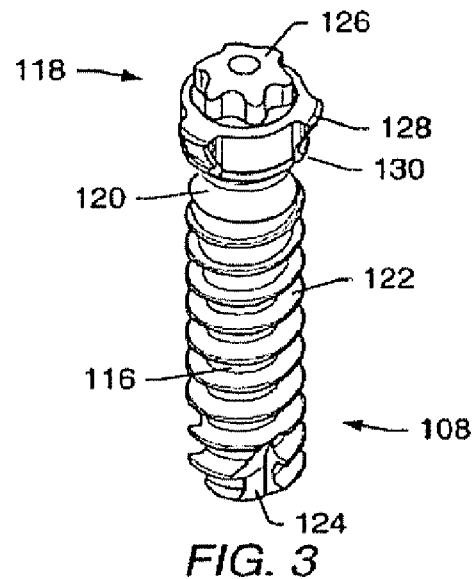
FIG. 3 depicts a perspective view of an embodiment of a bone fastener.
Figure 6:
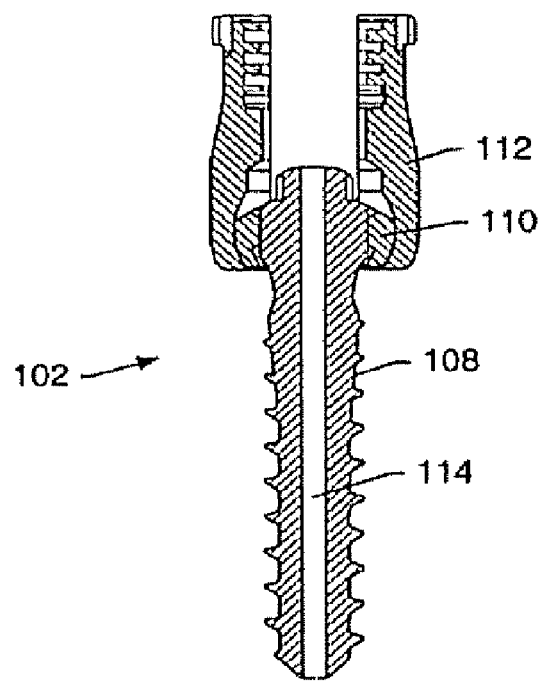
FIG. 6 depicts a cross-sectional view of an embodiment of a bone fastener assembly.
Figure 7:
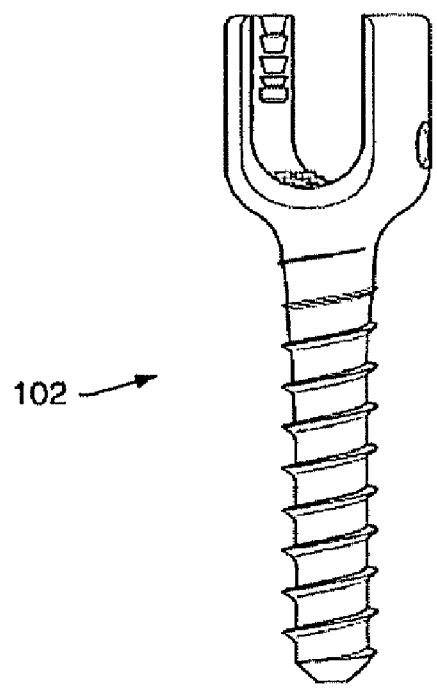
FIG. 7 depicts a perspective view of an embodiment of a bone fastener assembly.

FIG. 6 depicts a cross-sectional representation of bone fastener 108, ring 110, and collar 112 of bone fastener assembly 102. Bone fastener 108 of bone fastener assembly 102 may include passage 114. Bone fastener 108 may be cannulated (i.e., passage 114 may run through the full length of the bone fastener). A guide wire may be placed through passage 114 so that bone fastener 108 may be inserted into a vertebra at a desired location and in a desired angular orientation relative to the vertebra with limited or no visibility of the vertebra. In some embodiments, a bone fastener assembly may be a fixed angle fastener. FIG. 7 depicts an embodiment of a fixed angle bone fastener. Collar and bone fastener may be formed as a unitary piece of metal. A fixed angle fastener may be positioned as the first bone fastener assembly inserted into a vertebra. A bone fastener may be, but is not limited to, a bone screw, a ring shank fastener, a barb, a nail, a brad, or a trocar. Bone fasteners and/or bone fastener assemblies may be provided in various lengths in an instrumentation set to accommodate variability in vertebral bodies. For example, an instrumentation set for stabilizing vertebrae in a lumbar region of the spine may include bone fastener assemblies with lengths ranging from about 30 mm to about 75 mm in 5 mm increments. A bone fastener assembly may be stamped with indicia (i.e., printing on a side of the collar). In some embodiments, a bone fastener assembly or a bone fastener may be color-coded to indicate a length of the bone fastener. In certain embodiments, a bone fastener with a 30 mm thread length may have a magenta color, a bone fastener with a 35 mm thread length may have an orange color, and a bone fastener with a 55 mm thread length may have a blue color. Other colors may be used as desired. Each bone fastener provided in an instrumentation set may have substantially the same thread profile and thread pitch. In an embodiment, the thread may have about a 4 mm major diameter and about a 2.5 mm minor diameter with a cancellous thread profile. In certain embodiments, the minor diameter of the thread may be in a range from about 1.5 mm to about 4 mm or larger. In certain embodiments, the major diameter of the thread may be in a range from about 3.5 mm to about 6.5 mm or larger. Bone fasteners with other thread dimensions and/or thread profiles may also be used. A thread profile of the bone fasteners may allow bone purchase to be maximized when the bone fastener is positioned in vertebral bone. FIG. 3 depicts an embodiment of bone fastener 108. Bone fastener 108 may include shank 116, head 118, and neck 120. Shank 116 may include threading 122. In some embodiments, threading 122 may include self-tapping start 124. Self-tapping start 124 may facilitate insertion of bone fastener 108 into vertebral bone. Head 118 of bone fastener 108 may include various configurations to engage a driver that inserts the bone fastener into a vertebra. In some embodiments, the driver may also be used to remove an installed bone fastener from a vertebra. In some embodiments, head 118 may include one or more tool portions 126. Tool portions 126 may be recesses and/or protrusions designed to engage a portion of the driver. In some embodiments, bone fastener 108 may be cannulated for use in a minimally invasive procedure. Head 118 of bone fastener 108 may include one or more splines 128, as depicted in FIG. 3. In some head embodiments, head 118 may include three splines. Splines 128 may be equally spaced circumferentially around head 118 of bone fastener 108. In some head embodiments, spines 128 may be spaced at unequal distances circumferentially around head 118. Splines 128 may include various surface configurations and/or texturing to enhance coupling of bone fastener 108 with a ring of a bone fastener assembly. In some embodiments, sides of the splines may be tapered so that the splines form a dovetail connection with a ring. In some embodiments, spline width may be tapered so that a good interference connection is established when the bone screw is coupled to a ring. Splines 128 may include one or more projections 130 to facilitate coupling bone fastener 108 with an inner surface of a ring. In some embodiments, projections 130 may be positioned on a lower portion of splines 128. In some embodiments, the splines may include recessed surfaces that accept projections extending from surfaces of the ring. Neck 120 of bone fastener 108 may have a smaller diameter than adjacent portions of head 118 and shank 116.

The diameter of neck 120 may fix the maximum angle that the collar of the bone fastener assembly can be rotated relative to bone fastener 108.

Figure 4A:
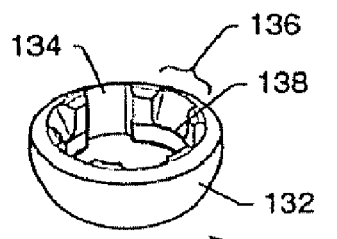
FIGS. 4A and 4B depict perspective views of embodiments of bone fastener assembly rings.
Figure 4B:
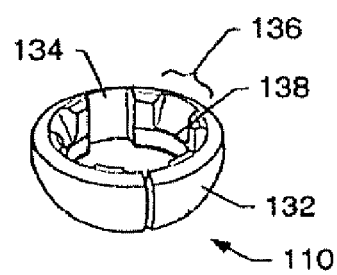

In some embodiments, neck 120 may be sized to allow up to about 40" or more of angulation of the collar relative to the bone fastener. In some embodiments, the neck may be sized to allow up to about 30" of angulation of the collar relative to the bone fastener. In some embodiments, the neck may be sized to allow up to about 20" of angulation of the collar relative to the bone fastener. FIGS. 4A and 4B depict perspective views of embodiments of ring 110. Outer surface 132 of ring 110 may have a contour that substantially complements a contour of an inner surface of a collar in which the ring resides. A contour of the outer surface of the ring may be a spherical portion. When the ring is positioned in the collar, the complementary shape of the ring outer surface and the inner surface of the collar that contacts the ring allows angulation of the collar relative to a bone fastener coupled to the ring. The contour of the outer surface of the ring and the inner surface of the collar may inhibit removal of the ring from the collar after insertion of the ring into the collar. Outer surface 132 of ring 110 may have a smooth finish. In some embodiments, outer surface 132 may be surface treated or include coatings and/or coverings. Surface treatments, coatings, and/or coverings may be used to adjust frictional and/or wear properties of the outer surface of the ring. In some embodiments, a portion of the outer surface of the ring may be shaped and/or textured to limit a range of motion of the collar relative to a bone fastener of a bone fastener assembly. An inner surface of ring 110 may include one or more grooves 134 and/or one or more seats 136. Seats 136 may be circumferentially offset from grooves 134. Grooves 134 may be sized to allow passage of splines of a bone fastener (e.g., splines 128 shown in FIG. 3) through the ring. When the splines are inserted through grooves 134, the bone fastener may be rotated until the splines align with seats 136. The bone fastener may be pulled or driven so that the splines are positioned in seats 136. In some embodiments, projections (e.g., projections 130 in FIG. 3) may pass over ridges 138 of ring 110. Passage of the projections over ridges 138 may securely couple the bone fastener to the ring and inhibit separation of the ring from the bone fastener.

In a ring embodiment, a number of grooves 134 and a number of seats 136 may equal a number of splines 128 on a head of a bone fastener. Seats 136 and grooves 134 may be equally spaced circumferentially around the inner surface of ring 110. In some embodiments, seats 136 may be circumferentially offset about 60" from grooves 134. In some embodiments, as shown in FIG. 4A, a ring may be a complete ring without a split or slots. In some embodiments, a ring may include a split or slots to facilitate insertion of the ring into a collar. FIG. 4B depicts a ring with a split. In some embodiments, a ring with a split and/or slots may be compressed to ease insertion into a collar. Once positioned in the collar, the ring may expand to its original uncompressed dimensions, thus inhibiting removal from the collar. As used herein, the term "collar" includes any element that wholly or partially encloses or receives one or more other elements. A collar may enclose or receive elements including, but not limited to, a bone fastener, a closure member, a ring, and/or an elongated member. In some embodiments, a collar may couple two or more other elements together (e.g., an elongated member and a bone fastener). A collar may have any of various physical forms. In some embodiments, a collar may have a "U" shape, however it is to be understood that a collar may also have other shapes. A collar may be open or closed. A collar having a slot and an open top, such as collar 112 shown in FIG. 2 and in FIG. 5, may be referred to as an "open collar." A bone fastener assembly that includes an open collar may be referred to as an "open fastener." In some embodiments, an elongated member may be top loaded into the open fastener. A closure member may be coupled to the collar to secure the elongated member to the open fastener. A collar that does not include a slot and an open top may be referred to as a "closed collar." A spinal implant that includes a closed collar may be referred to as a "closed implant." A closed collar may include an aperture, bore, or other feature in side surfaces for accommodating other components of a stabilization system (e.g., an elongated member). A setscrew may be used to securely couple an elongated member to a closed implant.

Collar 112 may include body 140 and arms 142. Arms 142 may extend from body 140. Body 140 of collar 112 may be greater in width than a width across arms 142 of collar 112 (i.e., body 140 may have a maximum effective outer diameter greater than a maximum effective outer diameter of arms 142). A reduced width across arms 142 may allow a detachable member to be coupled to the arms without substantially increasing a maximum effective outer diameter along a length of collar 112. Thus, a reduced width across arms 142 may reduce bulk at a surgical site. A height of body 140 may range from about 3 millimeters (mm) to about 7 mm. In an embodiment, a height of body 140 is about 5 mm. Body 140 may include opening 144 in a lower surface of the body. To inhibit passage of a ring from collar 112, opening 144 may be smaller than an outer diameter of the ring. Inner surface 146 may be machined to complement a portion of an outer surface of a ring that is to be positioned in collar 112. Machining of inner surface 146 may enhance retention of a ring in collar 112. Inner surface 146 of body 140 may be complementary in shape to a portion of outer surface 132 of ring 110 (see FIG. 4) so that the ring is able to swivel in the collar. Inner surfaces and/or outer surfaces of collar 112 may be surface treated or include coatings and/or coverings to modify frictional properties or other properties of the collar. Inner surfaces of arms 142 may include modified thread 148. Modified threads 148 may engage complementary modified threads of a closure member to secure an elongated member to a bone fastener assembly. Modified threads 148 may have a constant pitch or a variable pitch. A height and a width of arms 142 may vary. Arms 142 may range in height from about 8 mm to about 15 mm. In an embodiment, a height of arms 142 is about 11 mm. A width (i.e., effective diameter) of arms 142 may range from about 5 mm to 14 mm. Arms 142 and body 140 may form slot 150. Slot 150 may be sized to receive an elongated member. Slot 150 may include, but is not limited to, an elongated opening of constant width, an elongated opening of variable width, a rectangular opening, a trapezoidal opening, a circular opening, a square opening, an ovoid opening, an egg-shaped opening, a tapered opening, and combinations and/or portions thereof. In some embodiments, a first portion of slot 150 may have different dimensions than a second portion of slot 150. In certain embodiments, a portion of slot 150 in first arm 142 may have different dimensions than a portion of slot 150 in second arm 142.

When an elongated member is positioned in slot 150, a portion of the elongated member may contact a head of a bone fastener positioned in the collar. In an embodiment of a collar, arms 142 of collar 112 may include one or more openings and/or indentions 152. Indentions 152 may vary in size and shape (e.g., circular, triangular, rectangular). Indentions 152 may be position markers and/or force application regions for instruments that perform reduction, compression, or distraction of adjacent vertebrae. In some embodiments, openings and/or indentions may be positioned in the body of the collar. Arms 142 may include ridges or flanges 154. Flange 154 may allow collar 112 to be coupled to a detachable member so that translational motion of the collar relative to the detachable member is inhibited. Flanges 154 may also include notches 156. A movable member of a detachable member may extend into notch 156. When the movable member is positioned in notch 156, a channel in the detachable member may align with a slot in collar 112. With the movable member positioned in notch 156, rotational movement of collar 112 relative to the detachable member may be inhibited.

Figure 8A:
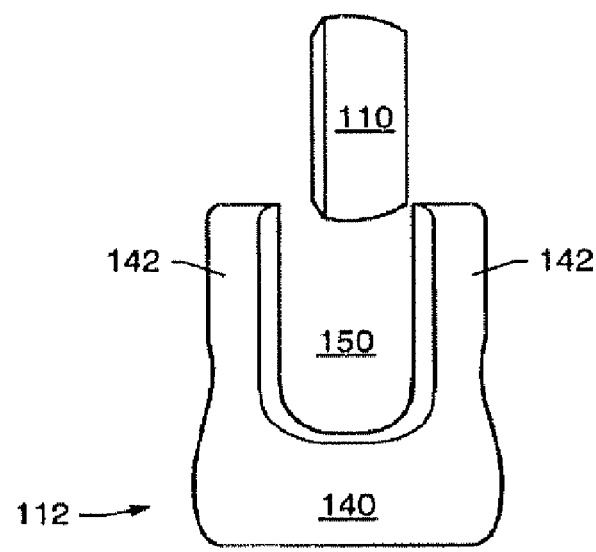
FIGS. 8A-8C depict schematic views of a method of positioning a ring in a collar of a bone fastener assembly.
Figure 8B:
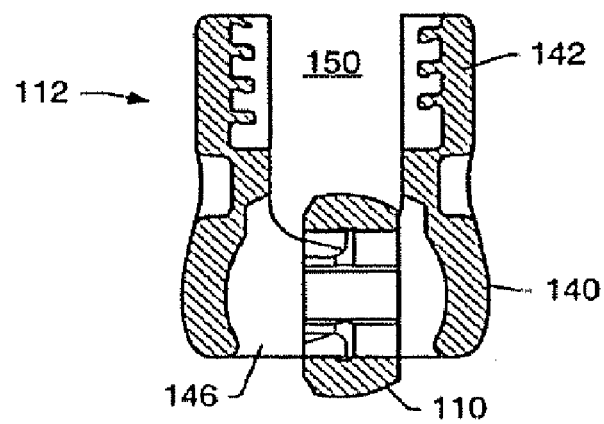
Figure 8C:
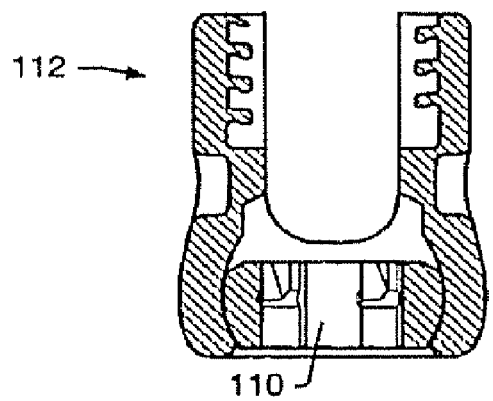

FIGS. 8A-8C show views of collar 112 and ring 110 during top loading insertion of the ring into the collar. Ring 110 may be positioned as shown in FIG. 8A and inserted past arms 142 into body 140. FIG. 8B depicts a cross-sectional view of ring 110 and collar 112 after insertion of the ring into the collar through slot 150. After insertion of ring 110 into collar 112, the ring may be rotated so that a bone fastener may be positioned through the ring. FIG. 8C depicts a cross-sectional view of ring 110 and collar 112 after rotation of the ring in the collar.

FIGS. 9A-9C show views of collar 112 and ring 110 during bottom loading insertion of the ring into the collar. Ring 110 may be positioned as shown in FIG. 9A and inserted into body 140 through an opening in the bottom of collar 112. In some embodiments, ring 110 may be inserted into body 140 through a groove or a slot in the bottom of collar 112. In certain embodiments, collar 112 designed for bottom insertion of ring 110 may have narrower slot 150 than a collar designed for top insertion of a ring. Collar 112 with narrower slot 150 may allow an elongated member with a reduced diameter to be used in a spinal stabilization system. Collar 112 with narrower slot 150 may be used to reduce bulk at a surgical site. FIG. 9B depicts a cross-sectional view of ring 110 and collar 112 after insertion of the ring into the collar through the opening in the bottom of the collar. After insertion of ring 110 into collar 112, the ring may be rotated so that a bone fastener may be positioned through the ring. Tolerance between an outer surface of ring 110 and an inner surface of body 140 shown in FIGS. 8A-8C and 9A-9C may require force to be applied to the ring to drive the ring into the body. Once ring 110 is positioned in body 140, the ring may expand slightly. In certain embodiments, significant force may be required to remove ring 110 from body 140 (i.e., the ring may be substantially unreleasable from the body). The required force may inhibit unintentional removal of ring 110 from body 140. FIG. 9C depicts a cross-sectional view of ring 110 and collar 112 after rotation of the ring in the collar.

Figure 10A:
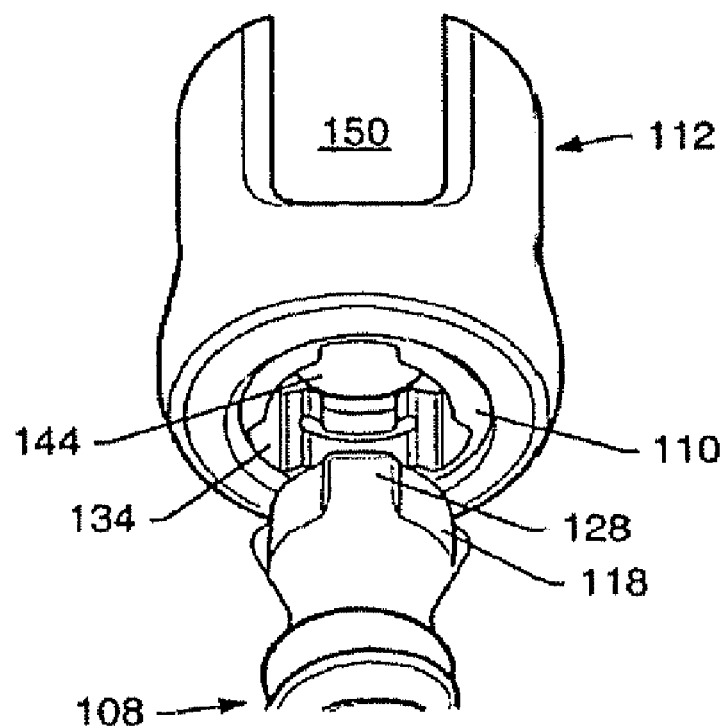
FIGS. 10A and 10B depict schematic views of positioning a bone fastener in a ring and collar to form a bone fastener assembly.
Figure 10B:
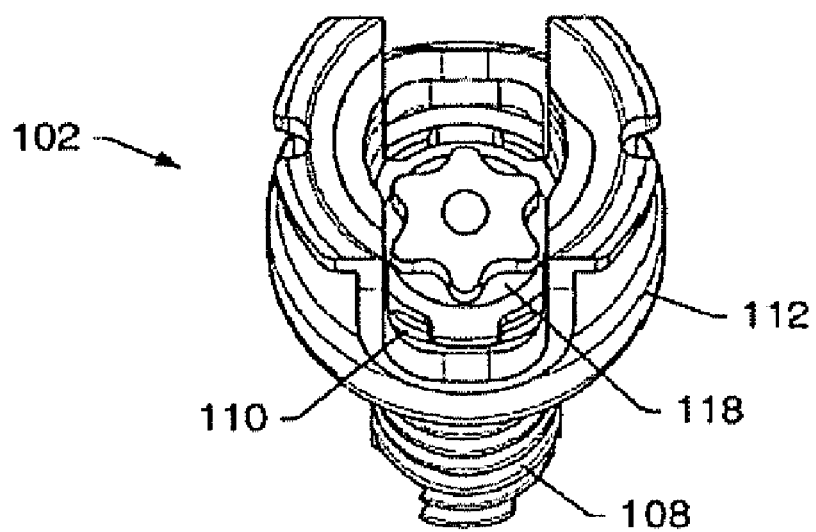

FIG. 10A depicts bone fastener 108 before insertion of the bone fastener into ring 110 positioned in collar 112. Splines 128 may be aligned with grooves 134 to allow passage of head 118 through ring 110 and into collar 112. FIG. 10B depicts bone fastener 108, ring 110, and collar 112 after the bone fastener has been rotated and head 118 has been coupled to seats in the ring to form bone fastener assembly 102. Inserting bone fastener 108 through opening 144 in collar 112 (depicted in FIG. 10A) may allow use of bone fasteners that have shanks and/or heads with larger diameters than can pass through slot 150. Bone fasteners with large diameter shanks may form a bone fastener assembly (threaded or otherwise) that securely fastens to vertebral bone during use. A bone fastener may be rotatably positioned in a collar such that the bone fastener is able to move radially and/or rotationally relative to the collar (or the collar relative to the bone fastener) within a defined range of motion. The range of motion may be provided within a plane, such as by a hinged connection, or within a three-dimensional region, such as by a ball and socket connection. Motion of the bone fastener relative to the collar (or the collar relative to the bone fastener) may be referred to as "angulation" and/or "polyaxial movement".

Figure 11:
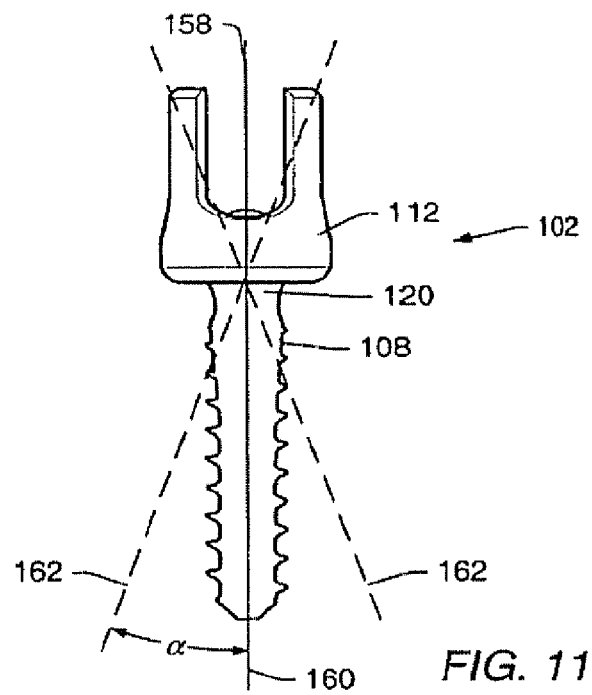
FIG. 11 depicts a front view of an embodiment of a bone fastener assembly with a collar that allows for angulation of a bone fastener relative to the collar in a conical range of motion that is symmetrical relative to an axis that passes through a central axis of the collar and a central axis of a bone fastener.

FIG. 11 depicts bone fastener assembly 102 with central axis 158 of collar 112 aligned with central axis 160 of bone fastener 108. Bone fastener 108 may be angulated in a symmetrical conical range of motion characterized by angle a about the aligned axes. Bone fastener 108 may be constrained from motion outside of limit axis 162 by contact between neck 120 of bone fastener 108 and collar 112. Alignment of axis 160 of bone fastener 108 with central axis 158 of collar 112 may be considered a neutral position relative to the range of motion. The alignment is a neutral position because bone fastener 108 may be angulated an equal amount in any direction from central axis 158. When a driver is inserted into bone fastener 108, axis 160 of bone fastener 108 may be substantially aligned with axis 158 of collar 112 to facilitate insertion of the bone fastener into a vertebral body. In certain embodiments, a range of motion of a collar may be skewed from a full conical range of motion relative to aligned central axes of the collar and a bone fastener coupled to the collar. In some embodiments, a distal end of a collar may be shaped to skew, or bias, the range of motion from the range of motion depicted in FIG. 11.

Figures 12A, 12B:
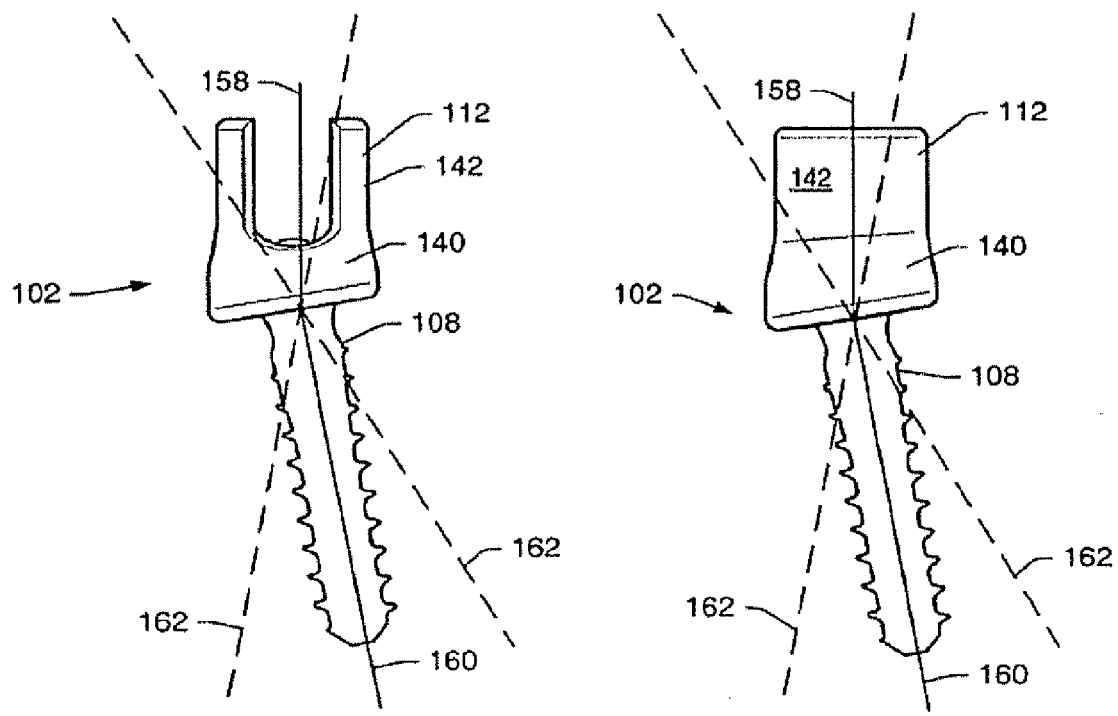
FIG. 12A depicts a front view of an embodiment of a bone fastener assembly with a collar that allows for angulation of a bone fastener relative to the collar in a conical range of motion that is not symmetrical relative to an axis that passes through a central axis of the collar and a central axis of a bone fastener. The collar allows additional lateral bias relative to a non-biased collar.
FIG. 12B depicts a side view of an embodiment of a bone fastener assembly with a collar that allows for angulation of a bone fastener relative to the collar in a conical range of motion that is not symmetrical relative to an axis that passes through a central axis of the collar and a central axis of a bone fastener. The collar allows additional caudal or cephalid bias relative to a non-biased collar.

FIGS. 12A and 12B depict bone fastener assemblies 102 with biased collars 112. Body 140 of biased collar 112 may be shaped to restrict relative movement of bone fastener 108 (and/or the collar) to a skewed conical range of motion defined by limit axes 162. As depicted by limit axes 162 in FIG. 12A, a first arm 142 of collar 112 may approach bone fastener 108 more closely than a second arm of the collar. As suggested by limit axes 162 in FIG. 12B, a first opening of the slot between arms 142 of collar 112 may approach bone fastener 108 more closely than a second opening of the slot. Other biased collars may be designed to selectively restrict relative movement of collars and/or bone fasteners. In some embodiments, a biased collar may be attached to a detachable member such that a surgeon performing a minimally invasive procedure may selectively align the portion of the collar with the greater range of motion as needed. For example, the collar depicted in FIG. 12A-B may be coupled to a single-level (e.g., C-shaped) sleeve so that the side of the collar (i.e., the side of the slot) with a larger range of motion is positioned next to a channel opening of the sleeve.

When a biased collar of a bone fastener assembly is coupled to a detachable member and a drive mechanism is coupled to a bone fastener of the bone fastener assembly, central axis 158 of collar 112 may align with central axis 160 of bone fastener 108 to facilitate insertion of the bone fastener into bone. In some embodiments, the bias of the collar may be so large that a flexible drive member is needed to drive the bone fastener into bone. In some embodiments, one or more biased collars may be used in a spinal stabilization system. The spinal stabilization systems may be single-level systems or multi-level systems. Biased collars may be used to accommodate the increasing angle of the pedicle corridor for each lumbar vertebra. The angle may increase by about degrees for each successive lumbar vertebra.

Figure 13A:
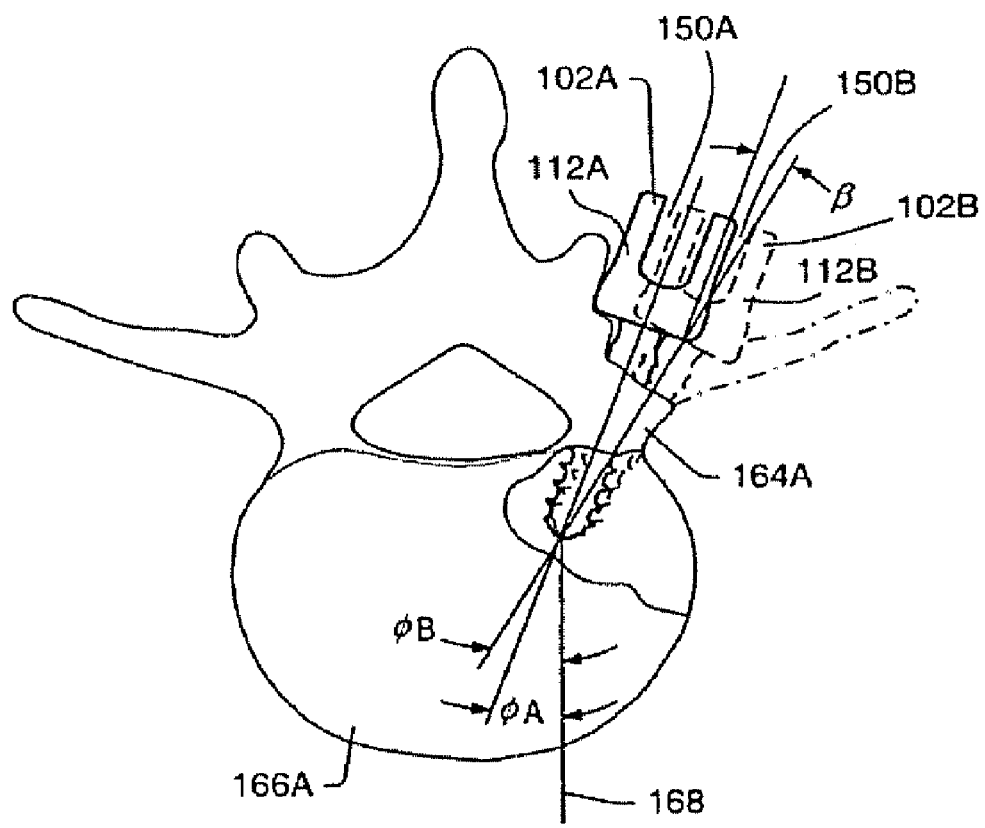
FIG. 13A depicts a schematic side view representation of embodiments of bone fastener assemblies positioned in vertebrae.
Figure 13B:
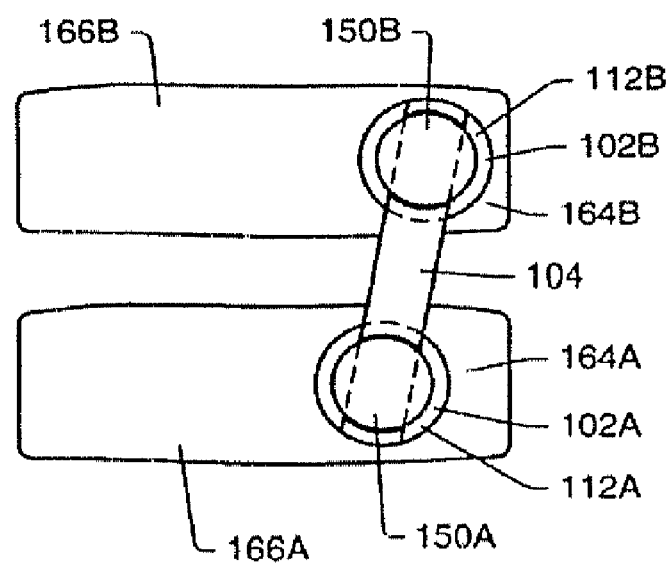
FIG. 13B depicts a schematic top view representation of an embodiment of a single-level spinal stabilization system.

FIGS. 13A and 13B depict a single-level spinal stabilization system including bone fastener assembly 102A coupled to pedicle 164A and vertebra 166A and bone fastener assembly 102B coupled to pedicle 164B and vertebra 166B. A bone fastener of bone fastener assembly 102A may engage pedicle 164A at pedicle angle ΦA relative to sagittal plane 168. Pedicle angle ΦA may range between about 13" and about 17". Collar 112A of bone fastener assembly 102A may be unbiased. Pedicle angle ΦB may range between about 18" and about 22". Collar 112B may have a bias angle P of about 5". Bone fastener assembly 102B may engage pedicle 164B at pedicle angle ΦB. Because the bias of collar 112B is approximately equal to the difference between the pedicle angles of the two vertebrae, slots 150A and 150B in bone fastener assemblies 102A and 102B, respectively, may be generally aligned when both bone fasteners are in neutral positions. Angulation of either or both collars of the bone fastener assemblies may allow fine adjustment of engagement angles of the bone fasteners. In addition, collar angulation may allow adjustment in the orientation of bone fasteners in a sagittal plane (i.e., to conform to lordosis of a spine) while still allowing the collars to be easily coupled with elongated member 104. Elongated member 104 may be disposed in slots 150A and 150B and secured by closure members.

In some embodiments, a flexible driver or a polyaxial driver (e.g., a driver with a universal joint) may be used to drive the heads of the bone fasteners from a position that is off axis from the bone fasteners to reduce the size of an opening of the body needed to implant the spinal stabilization system. A closure member may be coupled to a collar of a bone fastener assembly to fix an elongated member positioned in the collar to the bone fastener assembly. In some embodiments, a closure member may be cannulated. In certain embodiments, a closure member may have a solid central core. A closure member with a solid central core may allow more contact area between the closure member and a driver used to couple the closure member to the collar. A closure member with a solid central core may provide a more secure connection to an elongated member than a cannulated closure member by providing contact against the elongated member at a central portion of the closure member as well as near an edge of the closure member.

Figure 14:
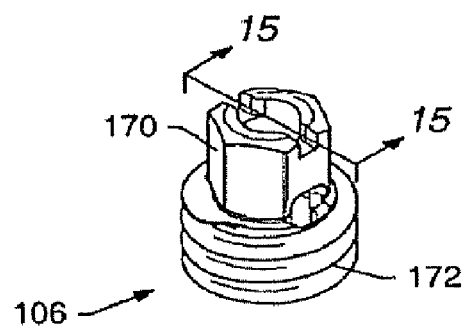
FIG. 14 depicts a perspective view of an embodiment of a closure member.
Figure 15:
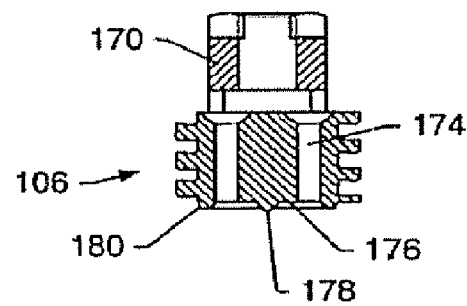
FIG. 15 depicts a cross-sectional representation of the closure member taken substantially along plane 15-15 indicated in FIG. 14.

FIG. 1 depicts closure members 106 coupled to bone fastener assemblies 102. FIG. 14 depicts closure member 106 prior to insertion of the closure member into a collar of a bone fastener assembly. Closure member 106 may include tool portion 170 and male modified thread 172. Tool portion 170 may couple to a tool that allows closure member 106 to be positioned in a collar. Tool portion 170 may include various configurations (e.g., threads, hexalobular connections, hexes) for engaging a tool (e.g., a driver). Male modified thread 172 may have a shape that complements the shape of a female modified thread in arms of a collar (e.g., modified thread 148 depicted in FIG. 5). FIG. 15 depicts a cross-sectional representation of closure member 106 taken substantially along plane 15-15 of FIG. 14. Closure member 106 may include removal openings 174. A drive tool may be inserted into removal openings 174 to allow removal of closure member 106 after tool portion 170 has been sheared off. Removal openings 174 may include any of a variety of features including, but not limited to, sockets, holes, slots, and/or combinations thereof. In an embodiment, removal openings 174 are holes that pass through bottom surface 176 of closure member 106. A bottom surface of a closure member may include structure and/or texturing that promotes contact between the closure member and an elongated member. A portion of the structure and/or texturing may enter and/or deform an elongated member when the closure member is coupled to the elongated member. Having a portion of the closure member enter and/or deform the elongated member may couple the elongated member to the closure member and a bone fastener assembly so that movement of the elongated member relative to the bone fastener assembly is inhibited.

In a closure member embodiment, such as the embodiment depicted in FIG. 15, bottom surface 176 of closure member 106 may include point 178 and rim 180. In some embodiments, rim 180 may come to a sharp point. In some embodiments, a height of rim 180 may be less than a height of point 178. In other embodiments, a height of rim 180 may be the same or larger than a height of point 178. In some embodiments, rim 180 may not extend completely around the closure member. For example, eight or more portions of rim 180 may be equally spaced circumferentially around closure member 106. In certain embodiments, a solid central core including point 178 and rim 180 may enhance the ability of closure member 106 to secure an elongated member in a collar.

Figure 16:
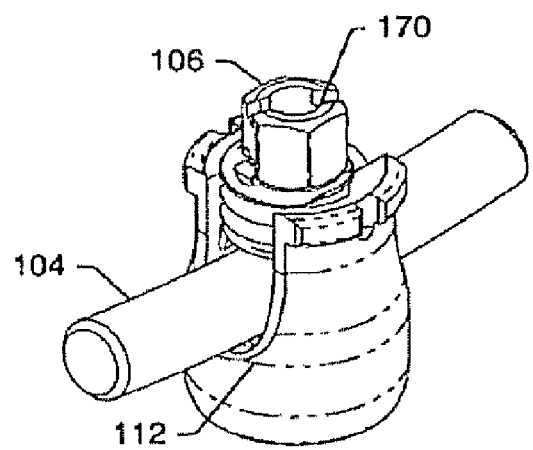
FIG. 16 depicts a perspective view of an embodiment of a portion of a spinal stabilization system.

FIG. 16 depicts a portion of a spinal stabilization system with closure member 106 coupled to collar 112 before tool portion 170 is sheared off. Closure member 106 may couple to collar 112 by a variety of systems including, but not limited to, standard threads, modified threads, reverse angle threads, buttress threads, or helical flanges. A buttress thread on a closure member may include a rearward-facing surface that is substantially perpendicular to the axis of the closure member. Closure member 106 may be advanced into an opening in a collar to engage a portion of elongated member 104. In some embodiments, closure member 106 may inhibit movement of elongated member 104 relative to collar 112.

FIG. 17A depicts a cross-sectional view of closure member 106 coupled to bone fastener assembly 102. Closure member 106 may include male modified thread 172. Male modified thread 172 may include male distal surface 182 and male proximal surface 184, as shown in FIG. 17B. Collar 112 may include female modified thread 148 on an inside surface of arms 142. Female modified thread 148 may include female proximal surface 186 and female distal surface 188. Male proximal surface 184 may couple to female distal surface 188 during use. Male proximal surface 184 and female distal surface 188 may be load-bearing surfaces. A load may result from an upward load on closure member 106, such as a load resulting when elongated member 104 positioned in a slot of collar 112 is secured to bone fastener assembly 102 by closure member 106.

Raised portions 190 and recessed portions 192 may be included on male distal surface 182 and female proximal surface 186. Cooperating surfaces 194 of modified threads 172 and 148 may contact or be proximate to one another during use. As used herein, "proximate" means near to or closer to one portion of a component than another portion of a component. Engagement of cooperating surfaces 194 of modified threads 172 and 148 during use may inhibit radial expansion of collar 112. Engagement of cooperating surfaces 194 may inhibit spreading of arms 142 away from each other (i.e., inhibit separation of the arms).

In some embodiments, cooperating surfaces 194 may be substantially parallel to a central axis of closure member 106. In other embodiments, cooperating surfaces 194 may be angled relative to a central axis of closure member 106. In some embodiments, a proximal surface of a male modified thread may include raised and recessed portions. FIG. 18A depicts a cross-sectional view of bone fastener assembly 102 coupled to closure member 106 with raised and recessed portions on a proximal surface of male modified thread 172. FIG. 18B depicts a cross-sectional view of raised portions 190 at male proximal surface 184 of male modified thread 172 and female distal surface 188 of female modified thread 148. Male proximal surface 184 may include an overall positive slope S such that point. A near the top of male modified thread 172 is distal from point B at the base of the male modified thread. Alternatively, male proximal surface 184 may include an overall negative slope or a slope of about zero.

In an embodiment, a bone fastener assembly and a closure member may be coupled with a running fit. A running fit (i.e., a fit in which parts are free to rotate) may result in predictable loading characteristics of a coupling of a bone fastener assembly and a closure member. Predictable loading characteristics may facilitate use of a closure member with a break-off portion designed to shear off at a predetermined torque. A running fit may also facilitate removal and replacement of closure members. In some embodiments, a closure member may include an interference fit (e.g., crest-to-root radial interference).

In an embodiment, a position (i.e., axial position and angular orientation) of a modified thread of a collar may be controlled, or "timed," relative to selected surfaces of the collar. For example, a modified thread form may be controlled relative to a top surface of a collar and an angular orientation of the slots of the collar. In some embodiments, positions of engaging structural elements of other coupling systems (e.g., thread forms) may be controlled.

Figure 5:
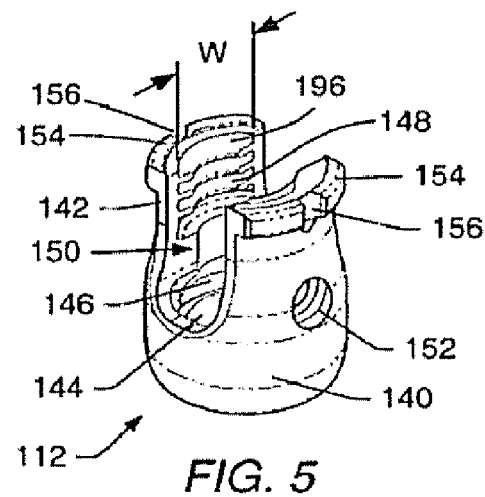
FIG. 5 depicts a perspective view of an embodiment of a bone fastener assembly collar.

Controlling a position of a modified thread form may affect a thickness of a top modified thread portion of a collar. In FIG. 5, top modified thread portion 196 is the first modified thread portion to engage a closure member. In an embodiment, a position of a modified thread form may be selected such that the thickness of the leading edge of a top modified thread portion is substantially equal to the full thickness of the rest of the modified thread.

Controlling a position of a modified thread form of a collar may increase a combined strength of engaged modified thread portions for a collar of a given size (e.g., wall height, modified thread dimensions, and thread pitch). Controlling a position of the modified thread form may reduce a probability of failure of modified thread portions, and thus reduce a probability of coupling failure between a collar and a closure member. Controlling the position of a modified thread form in a collar of a bone fastener assembly may increase a combined strength of engaged collar and closure member modified thread portions such that failure of the modified thread portions does not occur prior to the intended shearing off of a tool portion of the closure member. For example, a tool portion of a closure member may be designed to shear off at about 90 in-lbs of torque, while the combined modified thread portions may be designed to withstand a torque on the closure member of at least 120 in-lbs.

If a thickness of a modified thread portion of a given size and profile is reduced below a minimum thickness, the modified thread portion may not significantly contribute to the holding strength of the modified thread of a collar. In an embodiment, a position of a modified thread form of a collar may be controlled such that a thickness of a top modified thread portion is sufficient for the portion to increase a holding strength of the collar. In one embodiment, a top modified thread portion may have a leading edge thickness of about 0.2 mm.

In an embodiment, a position of a modified thread form of a collar may be selected to ensure that a closure member engages a selected minimum number of modified thread portions on each arm of the collar. In an embodiment, at least two modified thread portions having a full thickness over width w of a collar arm (shown in FIG. 5) may be engaged by a closure member at each arm. Alternatively, a closure member may engage parts of three or more modified thread portions on each arm, with the total width of the portions equal to at least two full-width portions. Allowances may be made for tolerances in the components (e.g., diameter of the elongated member) and/or anticipated misalignment between the components, such as misalignment between an elongated member and a slot. In an embodiment, a substantially equal number of modified thread portions in each arm may engage the closure member when an elongated member is coupled to a bone fastener assembly.

Various instruments may be used in a minimally invasive procedure to form a spinal stabilization system in a patient. The instruments may include, but are not limited to, positioning needles, guide wires, dilators, bone awls, bone taps, sleeves, drivers, tissue wedges, elongated member length estimating tools, mallets, tissue retractors, and tissue dilators. The instruments may be provided in an instrumentation set. The instrumentation set may also include components of the spinal stabilization system. The components of the spinal stabilization system may include, but are not limited to, bone fastener assemblies of various sizes and/or lengths, elongated members, and closure members. Instruments used to install a spinal stabilization system may be made of materials including, but not limited to, stainless steel, titanium, titanium alloys, ceramics, and/or polymers. Some instruments may be autoclaved and/or chemically sterilized. Some instruments may include components that cannot be autoclaved or chemically sterilized. Components of instruments that cannot be autoclaved or chemically sterilized may be made of sterile materials. The sterile materials may be placed in working relation to other parts of the instrument that have been sterilized.

Figure 20:
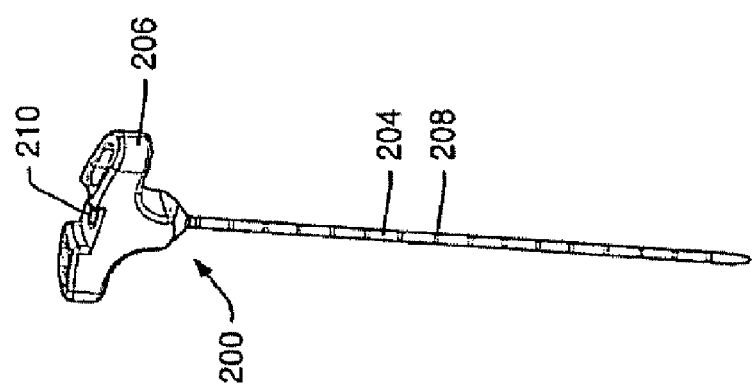
FIG. 20 depicts a perspective view of an outer housing of a targeting needle.
Figure 19:
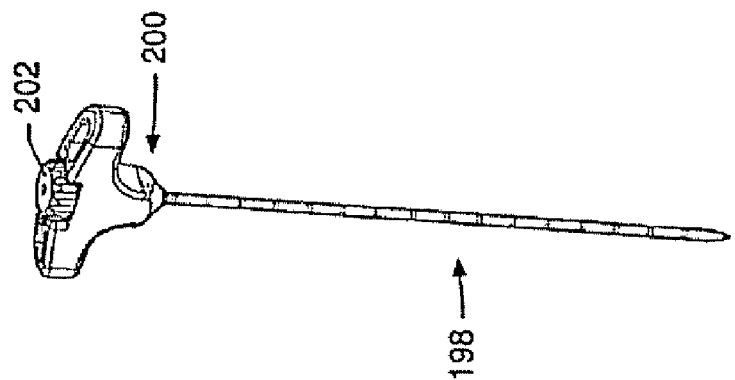
FIG. 19 depicts a perspective view of an embodiment of a targeting needle.

A targeting needle may be used to locate an entry point in a vertebral body for a bone fastener of a bone fastener assembly. In some embodiments, the targeting needle may be a bone marrow biopsy needle. FIG. 19 depicts an embodiment of targeting needle 198. Targeting needle 198 may include outer housing 200 and member 202. FIG. 20 depicts an embodiment of outer housing 200. Outer housing 200 may include hollow shaft 204 and handle 206. Scale markings 208 may be printed, etched, or otherwise placed on hollow shaft 204. Scale markings 208 may be used to approximate a length of a bone fastener needed for a vertebra. Handle 206 may provide a grip that allows a user to manipulate the targeting needle. Handle 206 may include threaded portion 210. Threaded portion 210 may couple to threading on a portion of a targeting needle member to secure the member to outer housing 200.

Figure 21:
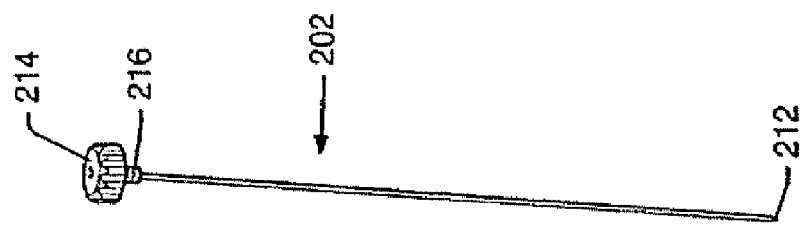
FIG. 21 depicts a perspective view of an embodiment of a member of a targeting needle.

FIG. 21 depicts an embodiment of member 202 of a targeting needle. Member 202 may include point 212 and cap 214. Point 212 may be placed through a hollow shaft of an outer housing of the targeting needle. Cap 214 may include threading 216. Member 202 may be rotated relative to the outer housing to couple threading 216 with threading in a handle of the outer housing. In some embodiments, the member may be coupled to the outer housing by another type of connection system (e.g., by placement of a key in a keyway). With member 202 positioned in an outer housing, point 212 may extend from a distal end of a hollow shaft of the outer housing. Cap 214 may be used as an impact surface for driving the targeting needle in bone.

Figure 22:
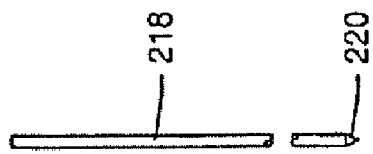
FIG. 22 depicts a perspective view of an embodiment of a guide wire.
Figure 23:
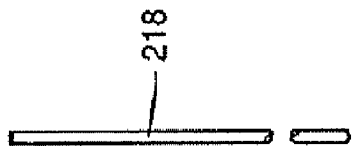
FIG. 23 depicts a perspective view of an embodiment of a guide wire.

FIG. 22 and FIG. 23 depict embodiments of guide wire 218. Guide wire 218 may be an 18-gauge K-wire. Guide wire 218 may pass down a shaft of a targeting needle outer housing. A guide wire may be from about 15 cm to about 65 cm in length. In some embodiments, guide wires provided in an instrumentation set are about 46 cm in length. The length of guide wire 218 may allow a surgeon and/or assistants to hold at least one portion of the guide wire at all times when the guide wire is inserted into vertebral bone, even during insertion, use, and removal of instruments along a length of the guide wire. A guide wire that can be held continuously during a surgical procedure may inhibit removal or advancement of the guide wire from a desired position during a minimally invasive surgical procedure.

As depicted in FIG. 22, a distal end of guide wire 218 may include point 220. Point 220 may facilitate insertion of the distal end of guide wire 218 into vertebral bone. As depicted in FIG. 23, a distal end of guide wire 218 may not be pointed. A position of an unpointed guide wire in bone may be easier to maintain during a spinal stabilization procedure.

Dilators may be used during a minimally invasive surgical procedure to push aside tissue and create space to access vertebral bone. In some embodiments, four tissue dilators of increasing diameter may be used to establish sufficient working space to accommodate instruments and spinal stabilization system components. In some embodiments, especially for a mid-vertebra or for mid-vertebrae of a multi-level stabilization system, only three dilators may be needed to form sufficient working space. Dilators in an instrumentation set may increase in diameter incrementally by a selected amount. For example, outside diameters of dilators in an instrumentation set may increase sequentially by increments of about 0.5 mm.

Figure 24:
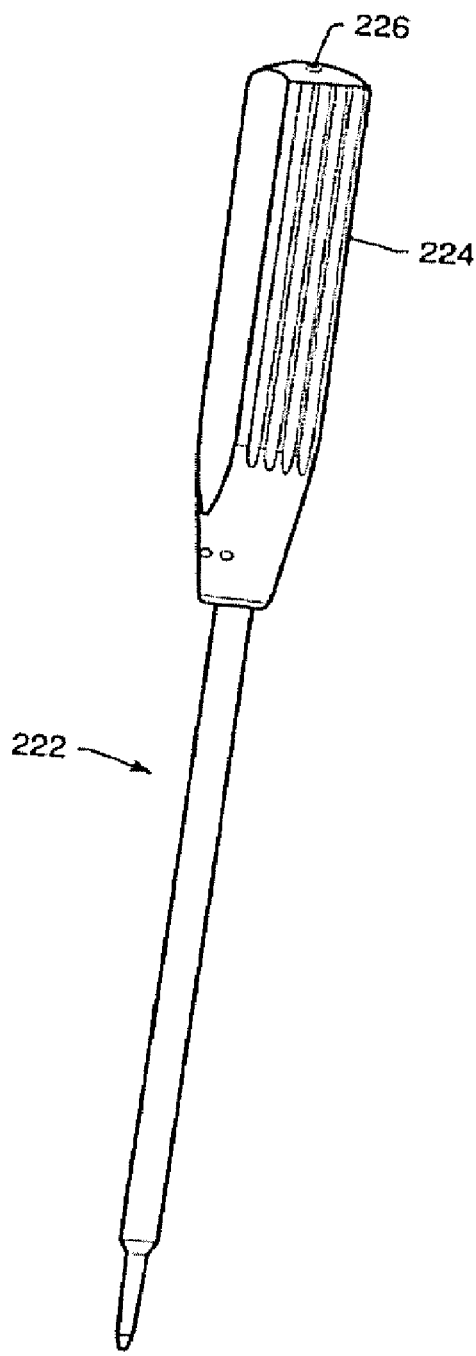
FIG. 24 depicts a perspective view of an embodiment of a bone awl.

A bone awl may be used to breach cortical bone of a pedicle. FIG. 24 depicts an embodiment of bone awl 222. Bone awl 222 may include handle 224, passage 226, and tip 228. Handle 224 may provide a secure grip that allows a surgeon to breach cortical bone of a pedicle with tip 228. A guide wire that is inserted in vertebral bone in a desired orientation may be inserted through passage 226 that extends through bone awl 222. Bone awl 222 may be moved down the guide wire so that tip 228 contacts the pedicle. Bone awl 222 may have a length that allows a guide wire positioned in vertebral bone to always be held in at least one location when the guide wire is placed through passage 226 in the needle. In some embodiments, handle 224 may be removable from a shaft of bone awl 222 so that the guide wire may always be held during use of the bone awl. During some surgical procedures downward force and some rotation of the bone awl may be-sufficient to breach cortical of a vertebra.

During some surgical procedures, an impact force may be needed for the bone awl to breach cortical bone. In some embodiments, a guide wire may be removed, the bone awl may be used to breach cortical bone, and the guide wire may be reinserted. In some embodiments, a small dilator may be placed over the portion of the guide wire extending from the bone awl so that a first end of the dilator contacts the bone awl. A mallet or other impact device may be used against a second end of the dilator so that the bone awl breaches cortical bone of the vertebra. The dilator may be removed from the bone awl and contact with the guide wire may be reestablished.

Figure 25:
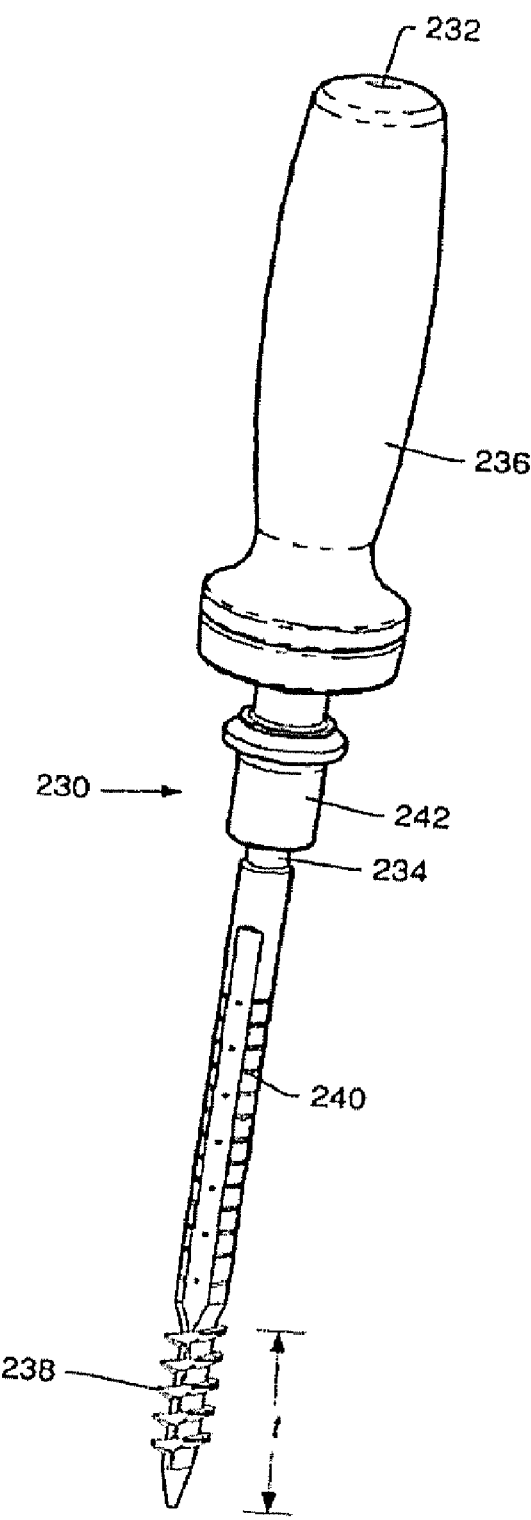
FIG. 25 depicts a perspective view of an embodiment of a bone tap.

A bone tap may be used to form a threaded passage of a desired depth through a pedicle and into a vertebral body. FIG. 25 depicts an embodiment of tap 230. Tap 230 may include passage 232, shaft 234, removable handle 236, flutes 238, and indicia 240. Passage 232 may extend through a length of shaft 234 and removable handle 236. A guide wire positioned in vertebral bone may be inserted into a distal end of passage 232 so that tap 230 can be moved down the guide wire toward the bone. In an embodiment of tap 230, a proximal portion of shaft 234 may include at least one flat portion that fits in a mating portion of removable handle 236. Proximal end of shaft 234 may also include a detent depression. The flat portion may allow for rotation of shaft 234 when removable handle 236 is rotated. An embodiment of removable handle 236 may include spring-loaded release 242. When spring-loaded release 242 is compressed (i.e., drawn upwards), a detent in removable handle 236 may be movable. When spring-loaded release 242 is not compressed, movement of the detent may be inhibited. When shaft 234 is positioned in removable handle 236, the detent of the removable handle may be positioned in the detent depression of shaft 234 to couple the shaft to the removable handle.

A tap portion of tap 230 may have a known length. As shown in FIG. 25, a tap portion of tap 230 may have a length t. In some embodiments, t may be about 20 mm, about 40 mm, about 60 mm, or greater. For example, t may be about 45 mm. X-ray monitoring of a depth of a tap portion of known length may allow a medical practitioner to assess a depth of a hole tapped in a bone. In some embodiments, the hole may be tapped to accommodate a bone fastener of a desired length. In certain embodiments, a bone fastener may be chosen to accommodate a hole tapped to a desired depth.

A guide wire positioned in vertebral bone may be held near a top of a dilator inserted over the guide wire at a surgical site. A proximal end of the guide wire may be positioned through a distal end of a passage in shaft 234 of tap 230 without a removable handle coupled to the shaft. A proximal portion of the guide wire may be held when the proximal portion of the guide wire extends beyond the top of shaft 234. A portion of the guide wire may always be held during use of tap 230. Shaft 234 may be moved down the guide wire until the shaft contacts the vertebral bone. The guide wire may be held near the top of shaft 234 and the guide wire may be positioned through passage 232 of removable handle 236. When the guide wire extends out of passage 232 through removable handle 236, the guide wire may be held above the removable handle. The handle may be coupled to the shaft using spring-loaded release 242.

A first reading of indicia 240 relative to a proximal end of a dilator may be taken when a first flute of flutes 238 is located at a pedicle. Tap 230 may be rotated so that flutes 238 form a threaded opening through the pedicle and into a vertebral body. Flutes 238 may have a diameter that is about 0.1 mm to about 0.7 mm less than a maximum thread flight of a bone fastener to be positioned in the threaded opening formed by the flutes. In an embodiment, tap may form a thread that is about 0.5 mm less than a maximum thread flight of a bone fastener to be positioned in the threaded opening formed by the flutes. A position of tap 230 may be monitored using a fluoroscope. When the threaded opening is formed to a desired depth, a second reading of indicia 240 relative to the dilator may be taken. A length of a bone fastener to be inserted into the vertebral body may be estimated by taking the difference between the indicia readings.

After a threaded opening is formed to a desired depth, tap 230 may be removed by rotating the tap until flutes 238 are disengaged from vertebral bone. Removable handle 236 may be separated from shaft 234, and the removable handle may be removed with the guide wire always held in at least one location. After removable handle 236 is removed from the guide wire, shaft 234 may be removed with the guide wire always held in at least one location. A detachable member may be used as a guide to install bone fasteners of a bone fastener assembly in vertebral bone. A detachable member may be coupled to a collar of a bone fastener assembly. A distal end of a detachable member may be tapered or angled to reduce bulk at a surgical site. Instruments may be inserted into the detachable member to manipulate the bone fastener assembly. Movement of the detachable member may alter an orientation of a collar relative to a bone fastener of the bone fastener assembly. In some embodiments, a detachable member may be used as a retractor during a spinal stabilization procedure.

A detachable member for a single-level vertebral stabilization system may include one or more channels in a wall of the detachable member to allow access to an adjacent vertebra. For some single-level vertebral stabilization procedures, only single-channel detachable members (i.e., detachable members with a single channel in a wall of the detachable member) may be used. For other single-level vertebral stabilization procedures, one or more multi-channel detachable members (i.e., detachable members with two or more channels in a wall of the detachable member) may be used. Channels may provide flexibility to or enhance flexibility of a multi-channel detachable member. In some embodiments, a proximal portion of a multi-channel detachable member may have a solid circumference. A region of solid circumference in a multi-channel detachable member may enhance stability of the multi-channel detachable member. In some embodiments, a multi-channel detachable member may be longer than a single-channel detachable member.

A detachable member used at a middle vertebra in a multi-level stabilization procedure may be a multi-channel detachable member. Channels in a multi-channel detachable member may allow access to adjacent vertebrae from a middle vertebra. A detachable member used at an end vertebra of a multi-level stabilization system may be a single-channel detachable member or a multi-channel detachable member. A system for coupling a bone fastener assembly to a multi-channel detachable member may include a limiter that inhibits spreading of arms of the detachable member to inhibit release of the bone fastener assembly from the detachable member.

A channel in a wall of a detachable member may allow access to a vertebra that is to be stabilized with a spinal stabilization system being formed. In some embodiments, a single-channel detachable member may be coupled to a bone fastener assembly to be inserted into vertebral bone of a first vertebra. The single-channel detachable member may allow access to a second vertebra from the first vertebra. In other embodiments, a multi-channel detachable member may be coupled to a bone fastener assembly to be inserted into vertebral bone of a first vertebra. The multi-channel detachable member may allow access from the first vertebra to adjacent vertebrae.

Instruments may access a bone fastener assembly through a passage in a detachable member. In some embodiments, a channel in a wall of a detachable member may extend a full length of the detachable member. In some embodiments, especially in embodiments of multi-channel detachable members, a channel in a wall of a detachable member may extend only a portion of the length of the detachable member. In some embodiments, a channel in a wall of a detachable member may extend 25%, 50%, 75%, 80%, 90%, 95% or more of the length of the detachable member. A channel may extend to a distal end of a detachable member such that an elongated member inserted in the channel may pass from the detachable member into a slot of a collar of a bone fastener assembly coupled to the detachable member.

A channel in a detachable member may be any of a variety of shapes. A channel may have a width that exceeds a width (e.g., a diameter) of an elongated member that is to be inserted in the channel. In some embodiments, a channel may be a linear opening parallel to a longitudinal axis of the detachable member. In some embodiments, a channel may have a non-linear shape including, but not limited to, a helical pattern, an arc, an "L" shape, or an "S" shape. A non-linear channel may allow an elongated member to travel along a predetermined path. In certain embodiments, adjacent detachable members may include channels with matching profiles, allowing ends of an elongated member to follow similar paths down the detachable member channels.

Movable members may extend through portions of a detachable member proximate a channel in the detachable member. Movable members may engage notches in a collar to establish a radial orientation of the detachable member on the collar and/or to inhibit rotation of the collar relative to the detachable member. A distal end of a movable member may be flat, curved, or angled. In some embodiments, a distal end of a movable member may be threaded. In other embodiments, a distal end of a movable member may be a projection that engages an opening in a collar. In some embodiments, an upper surface of a collar and/or a surface of a distal end of a movable member may be textured to inhibit rotation of the collar relative to the detachable member. In certain embodiments, a proximal end of a movable member may include a tool engaging portion. A tool engaging portion may include, but is not limited to, a hex section, a hexalobular section, a tapered section, a bead, a knot, a keyed opening, a coating, a threading, and/or a roughened surface for engaging a drive that rotates or otherwise displaces the movable member.

A cross section transverse to a longitudinal axis of a detachable member may have shapes including, but not limited to, circular, ovoid, square, pentagonal, hexagonal, and combinations thereof. In some embodiments, a detachable member may be hollow. In certain embodiments, a thickness of a hollow detachable member may be uniform. In certain embodiments, a thickness of a hollow detachable member may vary along the length of the detachable member. A detachable member with a passage extending longitudinally from a first end of the detachable member to a second end of the detachable member may be referred to as a "sleeve".

Figure 26:
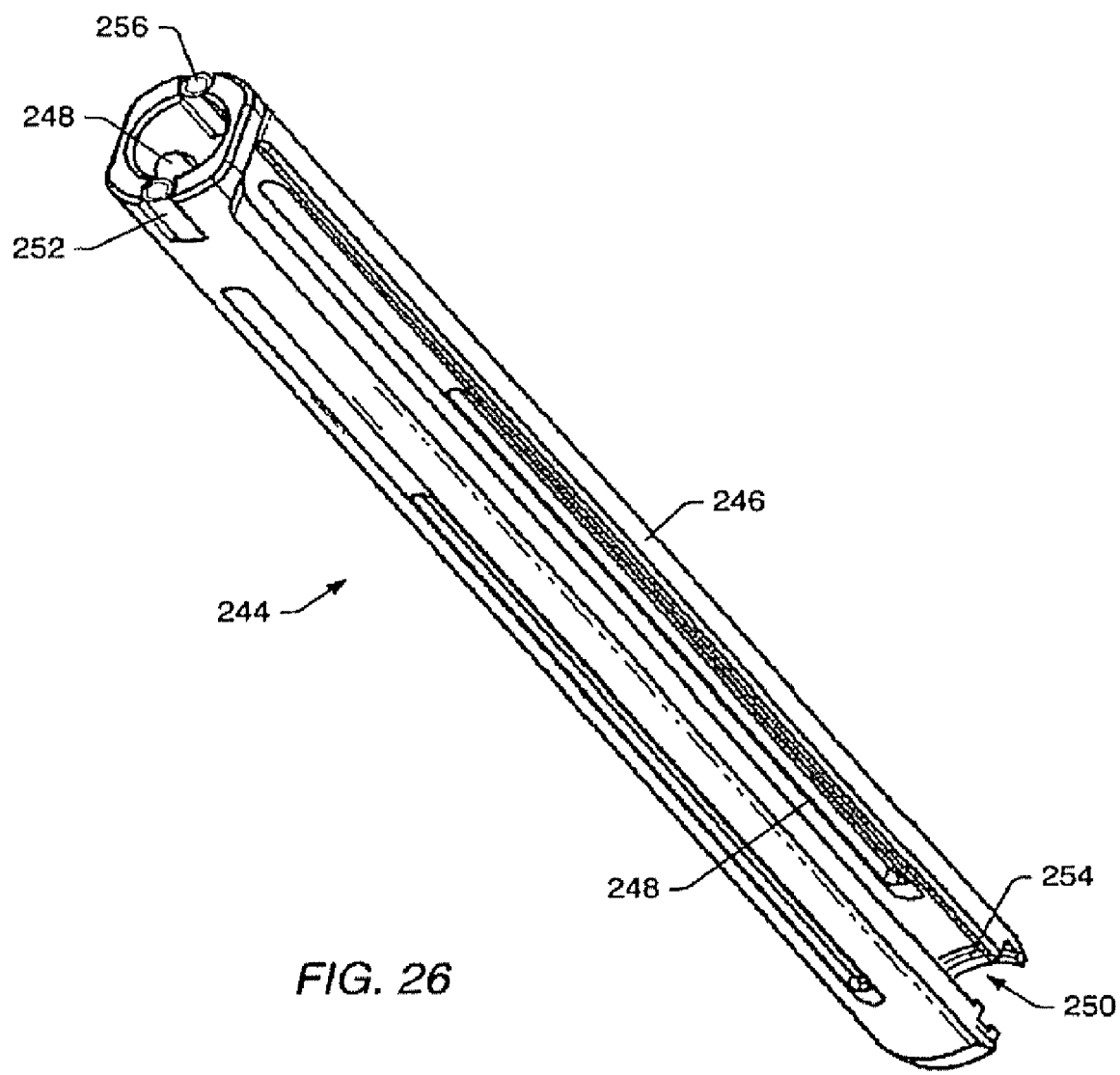
FIG. 26 depicts a perspective view of an embodiment of a multi-channel sleeve.

FIG. 26 depicts an embodiment of sleeve 244. Sleeve 244 may be a multi-channel sleeve. Sleeve 244 may include wall 246, channels 248, passage 250, movable members 252, and flange 254. Channels 248 may extend from a distal end of sleeve 244 through a portion of wall 246. Channels 248 may allow instruments to be positioned and used to form a plane through soft tissue to one or more adjacent vertebrae. An elongated member may be inserted in the tissue plane and positioned in collars of bone fastener assemblies anchored in vertebrae and coupled to sleeves. Passage 250 may allow instruments to be positioned and used to manipulate a bone fastener assembly that is coupled to a distal end of sleeve 244. Movable members 252 may be part of a system that couples a bone fastener assembly to sleeve 244. In some embodiments, movable members 252 may include tool engaging portion 256. A driver may be positioned in tool portion 256. The driver (e.g., a hex wrench) may be used to extend or retract a distal end of movable member 252. A distal end of sleeve 244 may include flange 254 that mates with a complementary flange on a collar of a bone fastener assembly. A distal end of sleeve 244 may be tapered to reduce bulk (e.g., reduce spin diameter) at a surgical site.

FIG. 27 depicts a top view of an embodiment of sleeve 244 coupled to a bone fastener assembly. Tool portion 126 of bone fastener 108 is a hexalobular connection.

FIG. 28 depicts a cross-sectional representation of a portion of sleeve 244 with bone fastener assembly 102 taken substantially along line 2828 of FIG. 27. Flange 254 of sleeve 244 may mate with flange 154 of collar 112 to inhibit translation of the sleeve relative to the collar. Sleeve 244 may also include stop 258. Stop 258 may engage a portion of collar 112 to inhibit separation of walls 246. During use, stop 258 may inhibit undesired separation of bone fastener assembly 102 from sleeve 244.

FIG. 29 depicts a cross-sectional representation of a portion of sleeve 244 with bone fastener assembly 102 and elongated member 104 taken substantially along line 29-29 of FIG. 27. Distal ends of movable members 252 may extend into notches (e.g. notches 156 depicted in FIG. 5) in collar 112. Portions of walls 246 of sleeve 244 may include threading. Portions of movable members 252 may include threading complementary to threaded portions of walls 246. Threading of movable members 252 may engage threading in walls 246 such that rotation of the movable members advances or retracts the movable members relative to the walls.

As shown in FIG. 29, collar 112 may be designed such that elongated member 104 lies below a distal end of sleeve 244. Coupling sleeve 244 to collar 112 above elongated member 104 may reduce bulk at a surgical site. With elongated member 104 coupled to collar 112 below a distal end of sleeve 244, the sleeve may be removed without interference from the elongated member of a spinal stabilization system.

Figure 30:
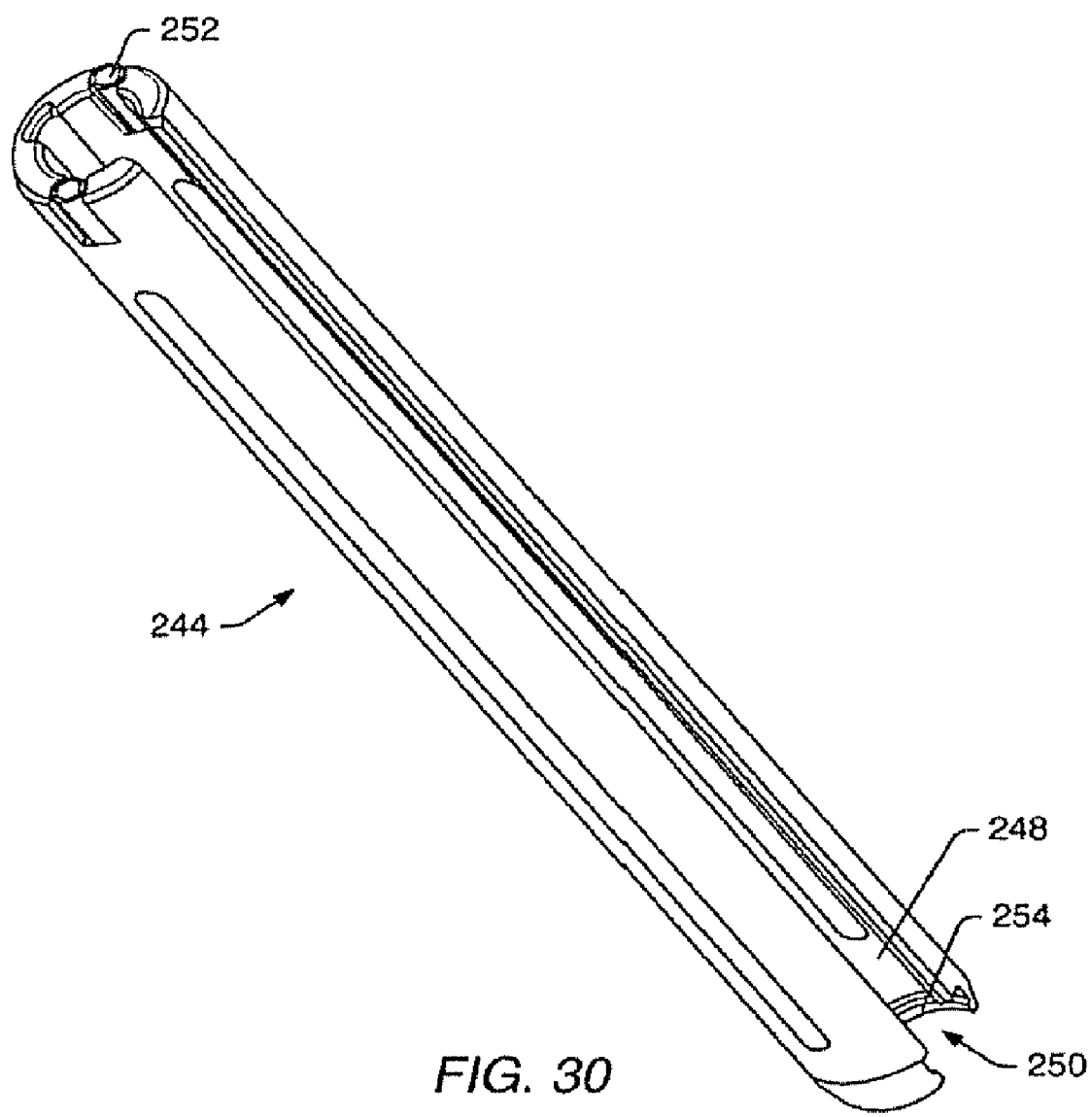
FIG. 30 depicts a perspective view of an embodiment of a single-channel sleeve.

FIG. 30 depicts an embodiment of sleeve 244. Sleeve 244 may be a single-channel sleeve for use in single-level or multi-level spinal stabilization procedures. Sleeve 244 may be used at the outermost vertebrae to be stabilized during installation of a multi-level vertebral stabilization system. Sleeve 244 may be coupled to a collar of a bone fastener assembly with movable members 252 and/or flange 254. Instruments may be inserted through passage 250 of sleeve 244 to access an anchored bone fastener assembly coupled to the sleeve. An instrument may be moved through channel 248 toward an adjacent vertebra to form a tissue plane in soft tissue between sleeve 244 and the adjacent vertebra.

A sleeve may be coupled to a bone fastener assembly in various ways to inhibit movement of the sleeve relative to a collar of the bone fastener assembly. A system used to couple the sleeve to the bone fastener assembly may inhibit rotation and translation of the sleeve relative to the collar.

Figures 31, 31A:
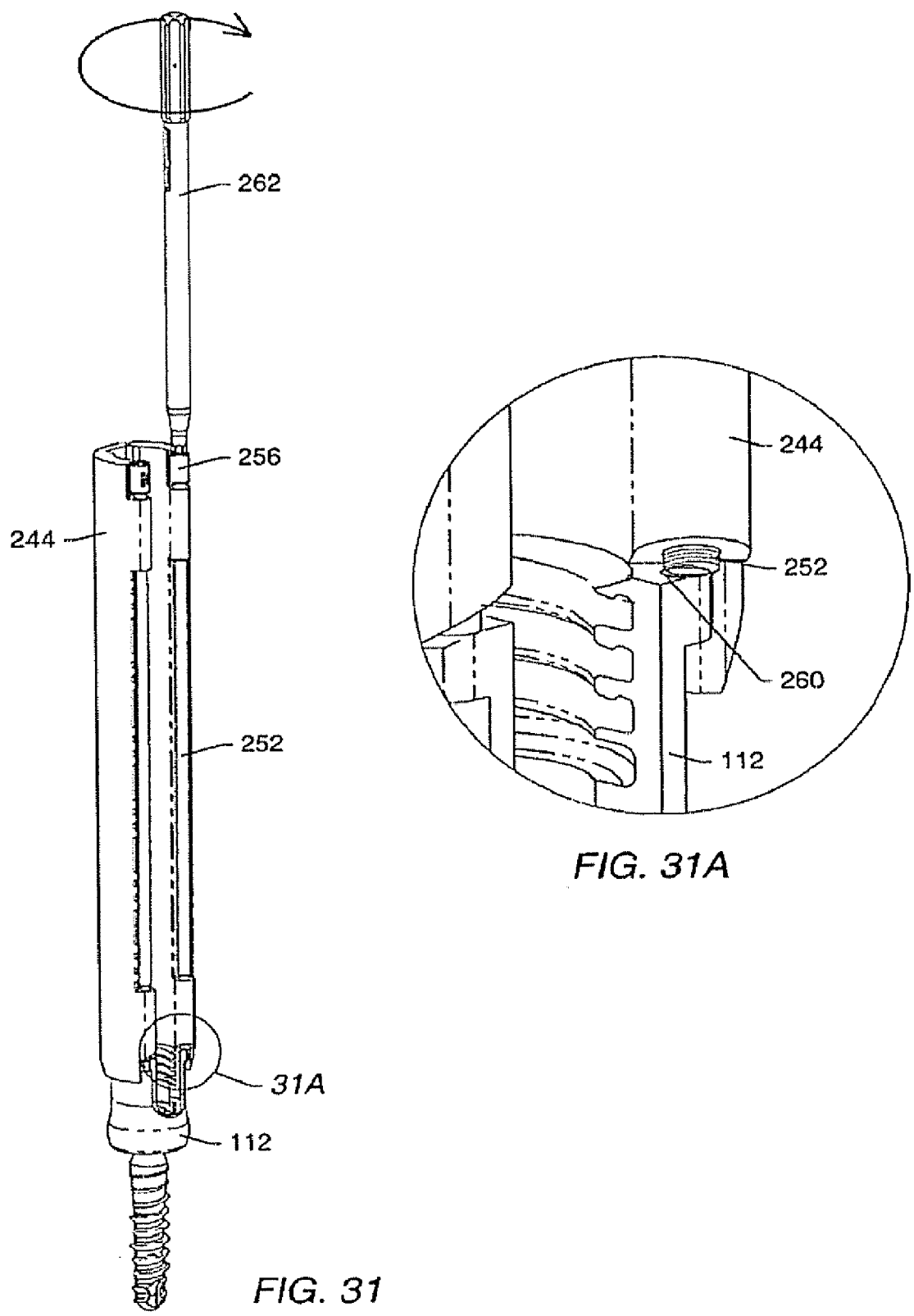
FIG. 31 depicts a perspective view of an embodiment of a sleeve during connection of the sleeve to a collar of a bone fastener assembly.
FIG. 31A depicts a detailed view of a portion of FIG. 31.

FIG. 31 depicts a perspective view of a sleeve embodiment during connection of the sleeve to collar 112 of a bone fastener assembly. Sleeve 244 may include movable members 252. Movable members 252 may include threaded distal end portions. FIG. 31A depicts a detailed view of a portion of sleeve 244 and collar 112. Collar 112 may include openings 260. Openings 260 may be threaded. Openings 260 of collar 112 may be aligned with movable members 252. A drive end of driver 262 may be positioned in tool engaging portion 256 of movable member 252. Driver 262 may be rotated to couple a threaded end of movable member 252 with threads in opening 260. The driver may be positioned in a tool opening of second movable member 252. The driver may be used to couple a threaded end of second movable member 252 with threads in second opening 260. Threaded connections between movable members 252 and collar 112 may inhibit movement of the collar relative to sleeve 244.

A detachable member may be coupled to a collar of a bone fastener assembly in various ways. When a detachable member is coupled to a collar, rotation and translation of the detachable member relative to the collar may be inhibited. A system used to couple a detachable member and collar should be simple, inexpensive to implement, and should not significantly weaken the mechanical strength of the collar and/or the detachable member. Detachable members may be coupled to collars using various coupling systems including, but not limited to, flanges, threaded connections, interlocking connections (e.g., ratcheting connection systems), and/or interference fits.

In an embodiment of an interlocking connection system, a detachable member may include an opposing pair of deflectable arms. Each deflectable arm may include a tooth. The deflectable arms may be forced outwards during coupling of a collar to the detachable member. When the collar is coupled to the detachable member, the deflectable arms may be positioned in channels in the collar, with the teeth positioned in indentions in the collar. The presence of the deflectable arms in the channels of the collar may inhibit rotation and translation of the detachable member relative to the collar. Separation of the detachable member from the collar may be achieved by insertion of an expander in the detachable member. The expander may be used to force the deflectable arms outwards and expel the teeth from the indentions.

FIGS. 32-45 depict embodiments of sleeves coupled to bone fastener assemblies. In each bone fastener assembly/sleeve embodiment depicted in FIGS. 32-43 and FIG. 45, an elongated member seated in the collar of the bone fastener assembly would lie below a distal end of sleeve 244. Having the elongated member below the distal end of sleeve 244 reduces bulk at the surgical site. With sleeve 244 positioned above the elongated member, interference of the secured elongated member with the sleeve is avoided during removal of the sleeve.

Figure 32:
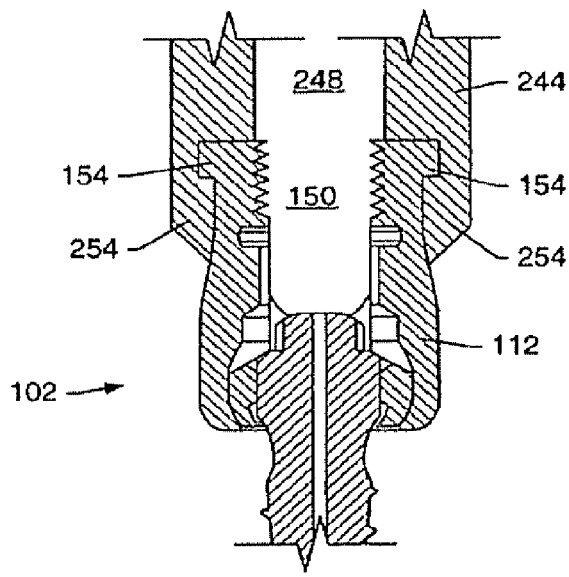
FIG. 32 depicts a partial cross-sectional representation of an embodiment of a sleeve coupled to a collar of a bone fastener assembly.

FIG. 32 depicts a cross-sectional representation of sleeve 244 including sleeve flange 254. Sleeve 244 may be rotated onto collar 112 until slot 150 aligns with channel 248. Sleeve flange 254 may engage flange 154 of collar 112 to inhibit translation of sleeve 244 relative to collar 112 of bone fastener assembly 102.

Figure 33:
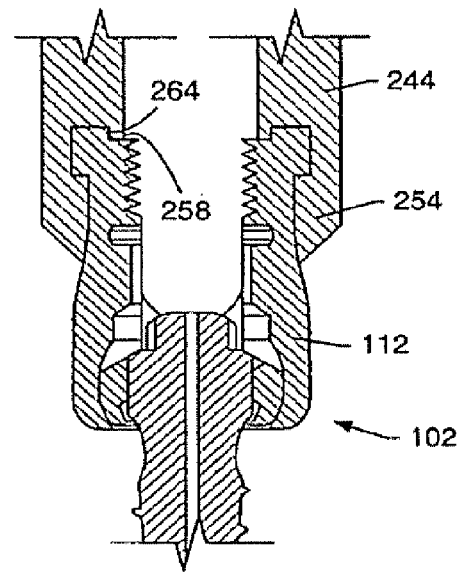
FIG. 33 depicts a partial cross-sectional representation of an embodiment of a sleeve coupled to a collar of a bone fastener assembly.

In some detachable member and collar coupling embodiments, the detachable member and the collar may include members that work together to inhibit radial expansion of walls of the detachable member. FIG. 33 depicts an embodiment of sleeve 244 coupled to an embodiment of bone fastener assembly 102. Sleeve 244 may include sleeve flange 254 and stop 258. Sleeve flange 254 may engage flange 154 of collar 112 to inhibit translation of sleeve 244 relative to the collar. Stop 258 may contact ledge 264 of collar 112. Contact of stop 258 against ledge 264 may inhibit release of collar 112 from sleeve 244 caused by radial expansion of walls of the sleeve. A stop in a sleeve and a ledge in a collar may be needed in a multi-channel sleeve embodiment. A stop in a sleeve and/or a ledge in a collar may not be needed in a single-channel sleeve embodiment or in a collar for a single-level stabilization.

Figure 34:
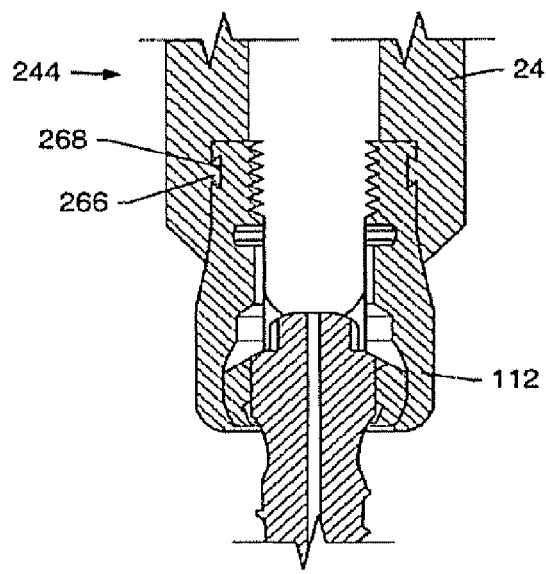
FIG. 34 depicts a partial cross-sectional representation of an embodiment of a sleeve coupled to a collar of a bone fastener assembly.
Figure 35:
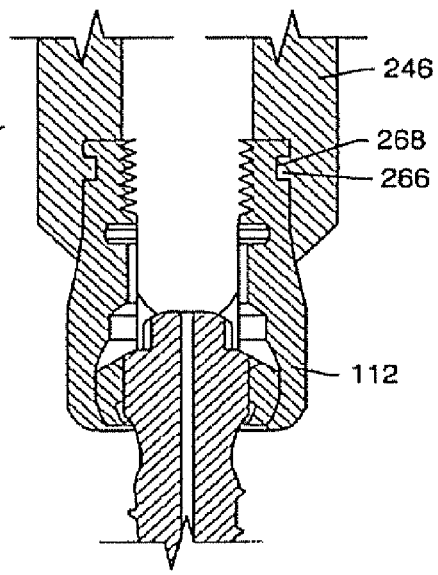
FIG. 35 depicts a partial cross-sectional representation of an embodiment of a sleeve coupled to a collar of a bone fastener assembly.

In some detachable member and collar coupling embodiments, a detachable member may include a protrusion that mates with a complementary groove in a collar. Alternatively, a detachable member may include a groove that mates with a complementary protrusion of a collar. FIG. 34 depicts a cross-sectional view of sleeve 244 with ridge 266. Ridge 266 may couple with groove 268 in collar 112 Ridge 266 and groove 268 may form a dovetail joint. The dovetail joint may inhibit radial expansion of sleeve walls 246. In some embodiments, such as the embodiment depicted in FIG. 35, ridge 266 and groove 268 may not form a dovetail joint.

In some embodiments, a detachable member and/or a collar may include a locking system to inhibit rotation of the detachable member relative to the collar. The locking system may be, but is not limited to, threading, interference fits, frictional engagement, or a press-fit connection. In some embodiments, a locking system may inhibit translation and/or rotation of a detachable member relative to a collar.

Figure 36:
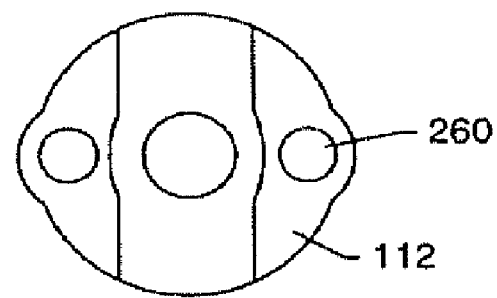
FIG. 36 depicts top view representation of an embodiment of a collar.

FIG. 36 depicts a top view representation of an embodiment of collar 112 of a bone fastener assembly. Collar 112 includes openings 260. In some embodiments, openings 260 may be threaded. In some embodiments, openings 260 may not include threading. The body of collar 112 adjacent to openings 260 may include extra material to provide strength to the collar.

Figure 37:
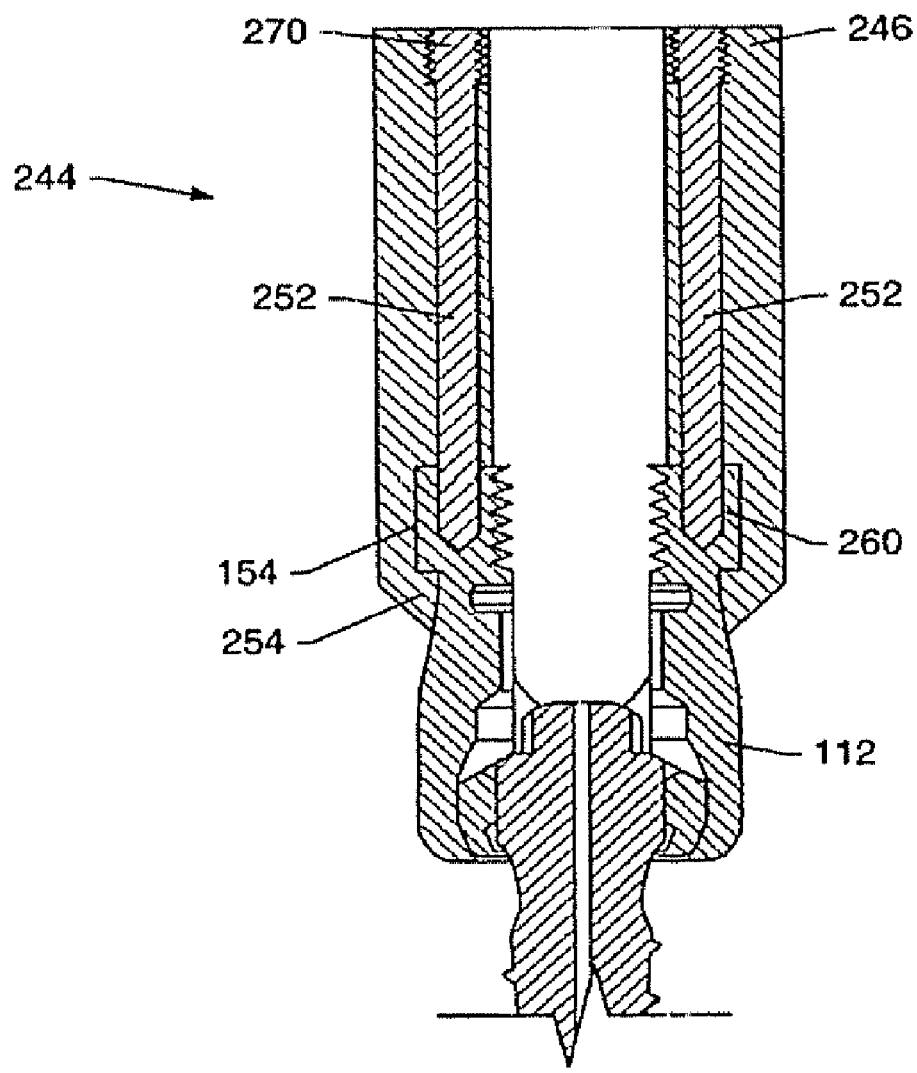
FIG. 37 depicts a partial cross-sectional representation of an embodiment of a sleeve coupled to an embodiment of a collar of a bone fastener assembly, such as the collar depicted in FIG. 36.

FIG. 37 depicts a partial cross-sectional representation of an embodiment of sleeve 244 coupled to an embodiment of collar 112, such as the collar depicted in FIG. 36. Distal end portions of movable members 252 may extend into openings 260. When distal end portions of movable members 252 are positioned in openings 260, rotational movement of sleeve 244 relative to collar 112 may be inhibited. Sleeve 244 may include flange 254. Flange 254 may engage flange 154 of collar 112 to inhibit translation of sleeve 244 relative to the collar. In an embodiment in which distal end portions of movable members in a sleeve are threaded and openings in the collar are threaded, rotation and translation of the collar relative to the sleeve may be inhibited when distal end portions of the movable members are positioned in the openings.

As depicted in FIG. 37, portion 270 of movable member 252 may include threading. Threading of portion 270 may engage threading in wall 246 of sleeve 244. Engagement of threading of portion 270 with threading in wall 246 may allow distal end portion of movable member 252 to advance towards, or retract from, a distal end of sleeve 244 when the movable member is rotated.

Figure 38:
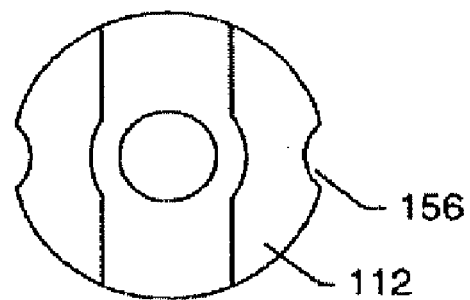
FIG. 38 depicts a top view representation of an embodiment of a collar.
Figure 39:
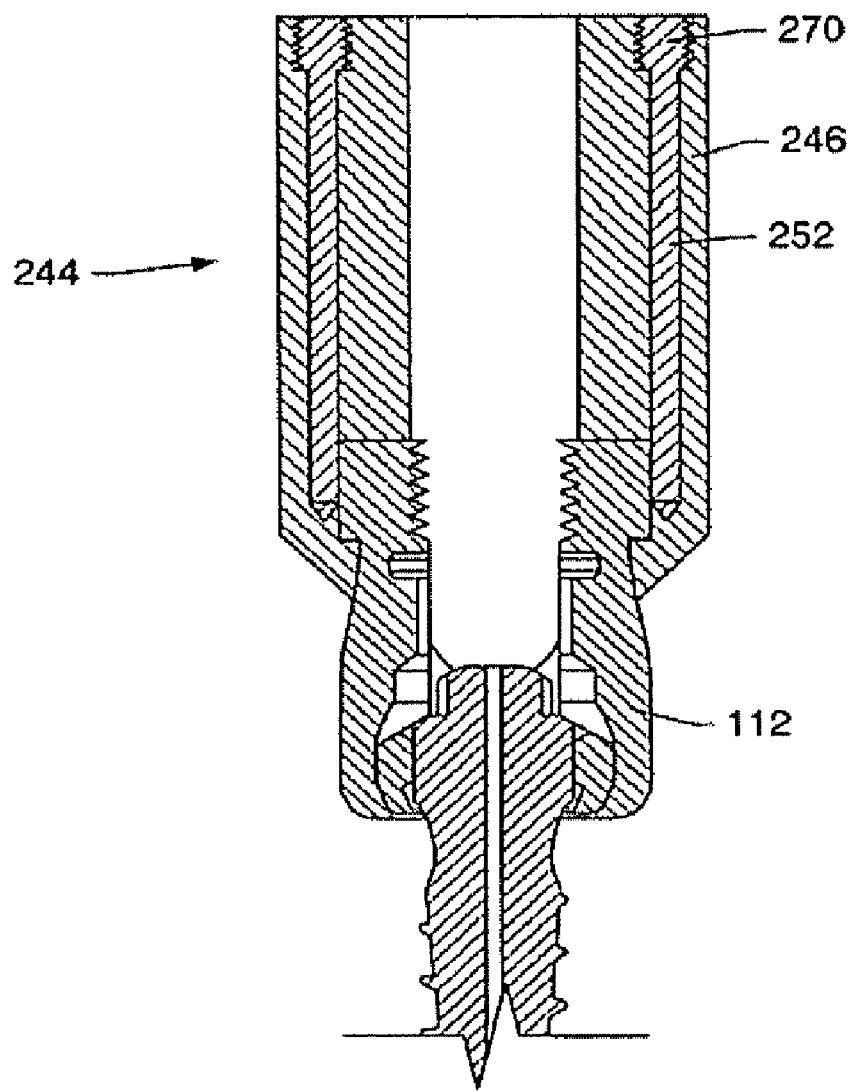
FIG. 39 depicts a partial cross-sectional representation of an embodiment of a sleeve coupled to an embodiment of a collar of a bone fastener assembly, such as the collar depicted in FIG. 38.

FIG. 38 depicts a top view representation of an embodiment of collar 112 of a bone fastener assembly. Collar 112 may include notches 156. FIG. 39 depicts a partial cross-sectional representation of an embodiment of sleeve 244 coupled to an embodiment of collar 112, such as the collar depicted in FIG. 38. Distal end portions of movable members 252 of sleeve 244 may be extended and positioned in notches 156 of collar 112. An interference fit between the distal end portions of movable members 252 and the body of collar 112 that defines the notches may inhibit rotation of sleeve 244 relative to the collar.

Portion 270 of movable member 252 may include threading. Threading of portion 270 may engage threading in wall 246 of sleeve 244. Engagement of threading of portion 270 with threading in wall 246 may allow a distal end portion of movable member 252 to advance towards, or retract from, a distal end of sleeve 244 when the movable member is rotated.

Figure 40:
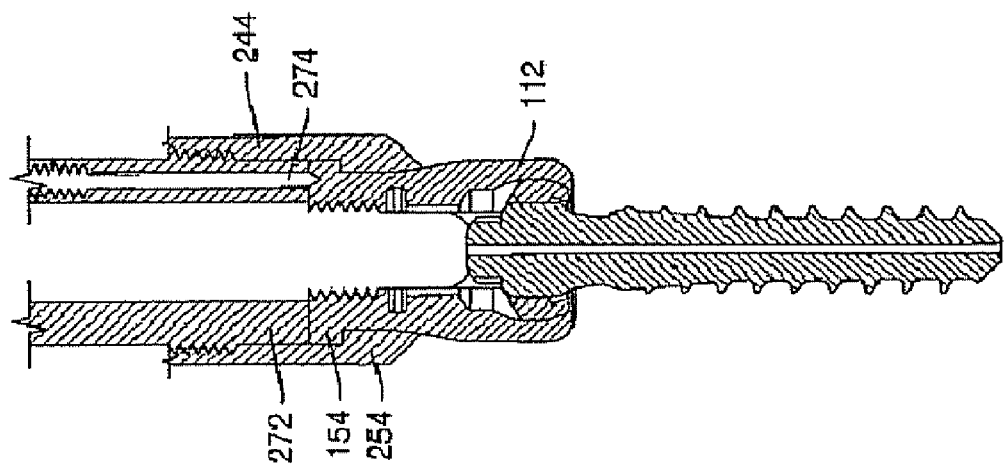
FIG. 40 depicts a partial cross-sectional view of an embodiment of a sleeve with an inner sleeve.

In an embodiment, an inner sleeve may be positioned in a sleeve to inhibit translation and/or rotation of the sleeve relative to a collar of a bone fastener assembly. FIG. 40 depicts a cross-sectional view of sleeve 244 with inner sleeve 272. A distal end of inner sleeve 272 may contact an upper end of collar 112. A proximal portion of inner sleeve 272 may engage a proximal portion of sleeve 244. The engagement may allow inner sleeve 272 to apply a force against collar 112 that presses flange 154 against flange 254 of sleeve 244 to inhibit translation of the sleeve relative to the collar. The engagement may be, but is not limited to, a threaded connection, an interference fit, a frictional fit, or a keyway type of connection.

In some embodiments, a distal end of an inner sleeve may be roughened or textured to frictionally engage a proximal surface of the collar. The frictional engagement may inhibit rotation of the sleeve relative to the collar. In some embodiments, inner sleeve 272 may include passage 274. A pin may pass through passage 274 into an opening in collar 112. When a pin is positioned through passage 274 into the opening, rotation of sleeve 244 relative to collar 112 may be inhibited.

Figure 42:
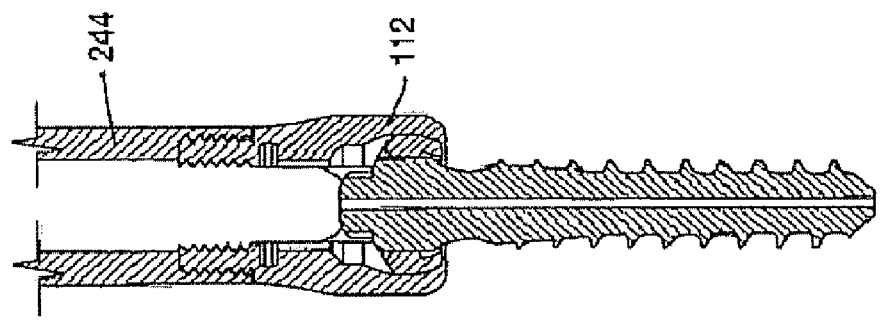
FIG. 42 depicts a partial cross-sectional representation of an embodiment of a sleeve coupled to a collar of a bone fastener assembly.
Figure 41:
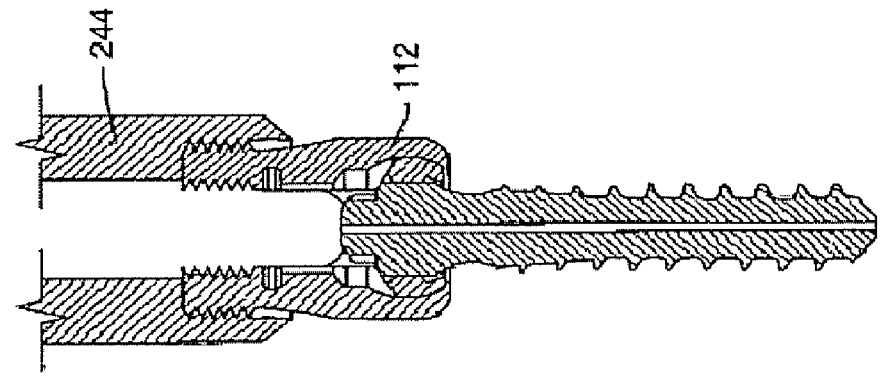
FIG. 41 depicts a partial cross-sectional representation of an embodiment of a sleeve coupled to a collar of a bone fastener assembly.

In some embodiments, threading may be used to couple a detachable member to a collar. FIG. 41 and FIG. 42 depict partial cross-sectional representations of sleeves 244 that couple to collars 112 by threaded connections. Sleeves 244 may include female threading that is complementary to male threading of collar 112. In some embodiments, threading of the sleeve and threading of the collar may be modified threads.

Figure 43:
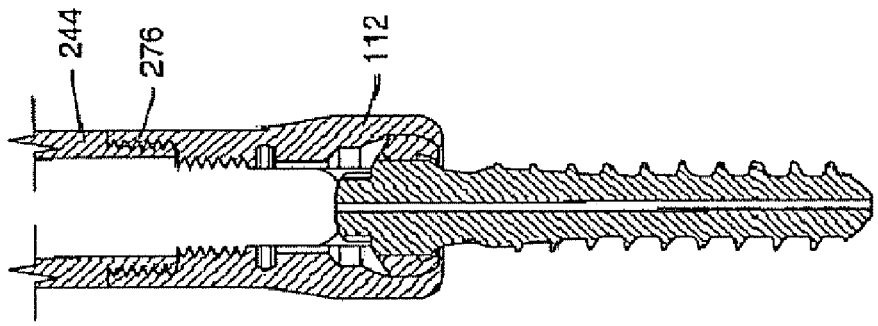
FIG. 43 depicts a partial cross-sectional representation of an embodiment of a sleeve coupled to a collar of a bone fastener assembly.

FIG. 43 depicts a partial cross-sectional representation of sleeve 244 that couples to collar 112 by a threaded connection. Sleeve 244 may include male threading, and collar 112 may include complementary female threading. In some embodiments, portion 276 of collar 112 that includes threading which mates with threading of sleeve 244 may be a break-off section. Collar 112 may be held in a fixed position. Torque may be applied to sleeve 244 to shear off portion 276.

Figure 44:
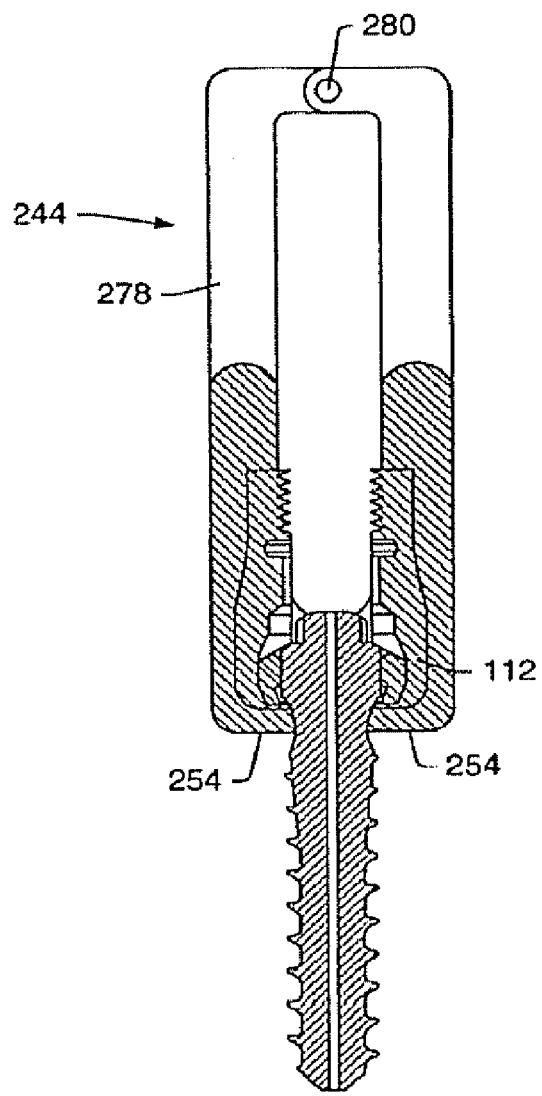
FIG. 44 depicts a cross-sectional representation of an embodiment of a hinged sleeve coupled to a collar of a bone fastener assembly.
Figure 45:
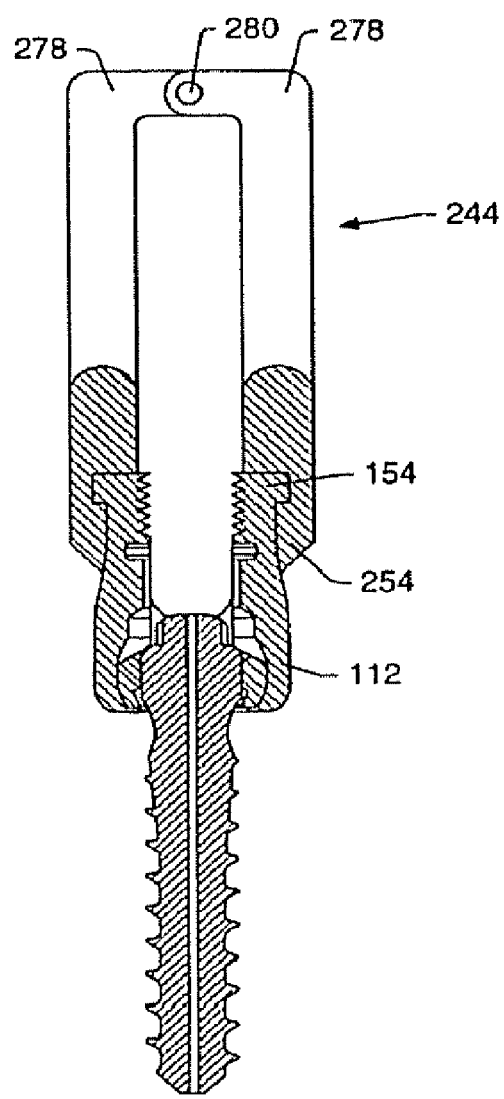
FIG. 45 depicts a cross-sectional representation of an embodiment of a hinged sleeve coupled to a collar of a bone fastener assembly.

In some embodiments, a detachable member may include a pair of hinged arms configured to couple to a collar. FIG. 44 and FIG. 45 depict embodiments of sleeves that include hinged portions. Sleeve 244 may include arms 278. Arms 278 may be pivotally coupled together by hinge 280. Hinge 280 may be located near a proximal end of sleeve 244. In some sleeve embodiments, sleeve 244 may include a locking element or a biasing element (e.g., a spring) near or at hinge 280. A locking element or biasing element may cause a clamping force to be exerted on collar 112 to maintain the collar in the sleeve and/or to inhibit rotation of collar 112 in sleeve 244. In some embodiments, such as in the embodiment depicted in FIG. 44, flange 254 of sleeve 244 may contact a bottom portion of collar 112. In some embodiments, such as in the embodiment depicted in FIG. 45, flange 254 of sleeve 244 may contact flange 154 of collar 112.

Figure 46:
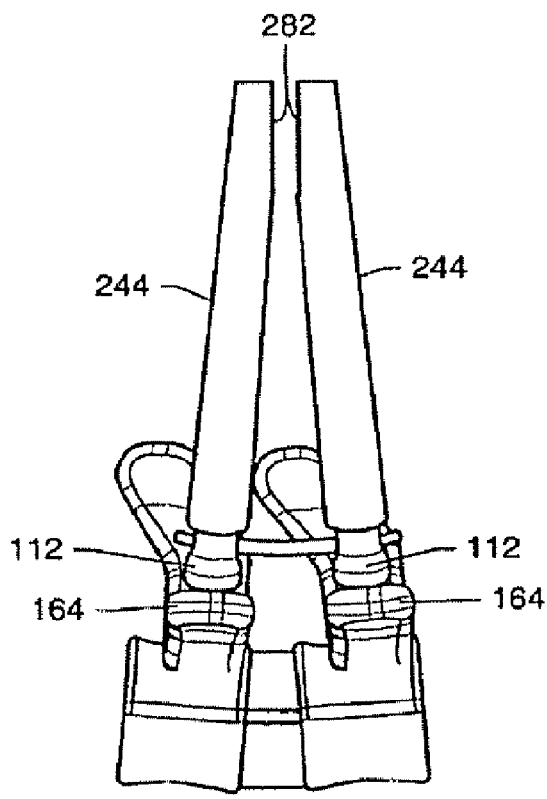
FIG. 46 depicts a schematic representation of sleeve embodiments coupled to collars of a spinal stabilization system.

In some detachable member embodiments, proximal portions of detachable members may be chamfered to allow ends of the detachable members to more closely approach each other than detachable members with a uniform cross section. FIG. 46 depicts sleeves 244 coupled to collars 112 engaged in adjacent pedicles 164. Sleeves 244 may include chamfered surfaces 282. Chamfered surfaces 282 may reduce space between proximal ends of sleeves 244. During some surgical procedures, only one of the sleeves may be chamfered. During some surgical procedures, the use of a sleeve with a chamfered surface may allow for a smaller incision than required when using non-chamfered sleeves. In some embodiments, other types of detachable members may be used to reduce space between proximal ends of detachable members. Other types of detachable members may include, but are not limited to, detachable members of different lengths, detachable members of different diameters, and detachable members with flexible end portions.

Detachable members may be of various lengths. Detachable members of different lengths may be used in the same surgical procedure. A detachable member length used in a spinal stabilization procedure may be determined by a patient's anatomy. Detachable members may be just short enough to allow manipulation by a medical practitioner above an incision in a patient. In some embodiments, detachable members may be about 3.5 to about 11.5 cm long. For example, a single-channel detachable member may be about 10 cm long. In some embodiments, detachable members may be about 11.5 cm to about 14 cm long. For example, a single-channel or a multi-channel detachable member may be about 12.5 cm long. A multi-channel detachable member may be longer than a single-channel detachable member. In some embodiments, a multi-channel detachable member may be at least about 15 cm long. For example, a multi-channel detachable member may be about 16 cm long. Detachable members that are too long may require a longer incision and/or a larger tissue plane for insertion of a spinal stabilization system. Insertion of an elongated member may be more difficult with detachable members that are longer than necessary. Detachable members with excess length may be bulky and hard to manipulate during a surgical procedure.

A detachable member may be flexible over its entire length or include a flexible portion near a proximal end of the detachable member. A flexible portion may allow positioning of a proximal portion of a detachable member in a desired location. A flexible portion may be produced from any of various materials including, but not limited to, a surgical grade plastic, rubber, or metal. A flexible portion may be formed of various elements, including, but not limited to, a tube, a channel, or a plurality of linked segments.

Figure 47:
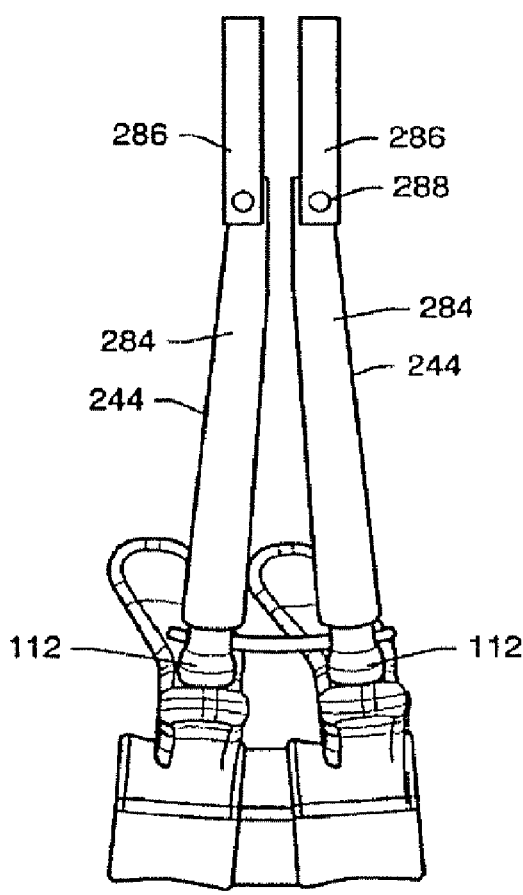
FIG. 47 depicts a schematic representation of sleeve embodiments with connections that allow relative movement of portions of a sleeve.

FIG. 47 depicts an embodiment of sleeve 244 with a connection that allows movement of first portion 284 relative to second portion 286. First portion 284 may be coupled to collar 112 of a bone fastener assembly. Second portion 286 may connect to first portion 284 at linkage 288. Linkage 288 may include, but is not limited to, a locking element, a pivot point, a hinge, or a pin. In some embodiments, the linkage may be a ball and socket type of connection that allows rotational motion of second portion 286 relative to first portion 284. During some spinal stabilization procedures, a detachable member without a second portion that is able to move relative to a first portion may be used at one vertebra, and a detachable member with a second portion that is able to move relative to a first portion may be used at one or more vertebrae that are to be stabilized.

Figure 48:
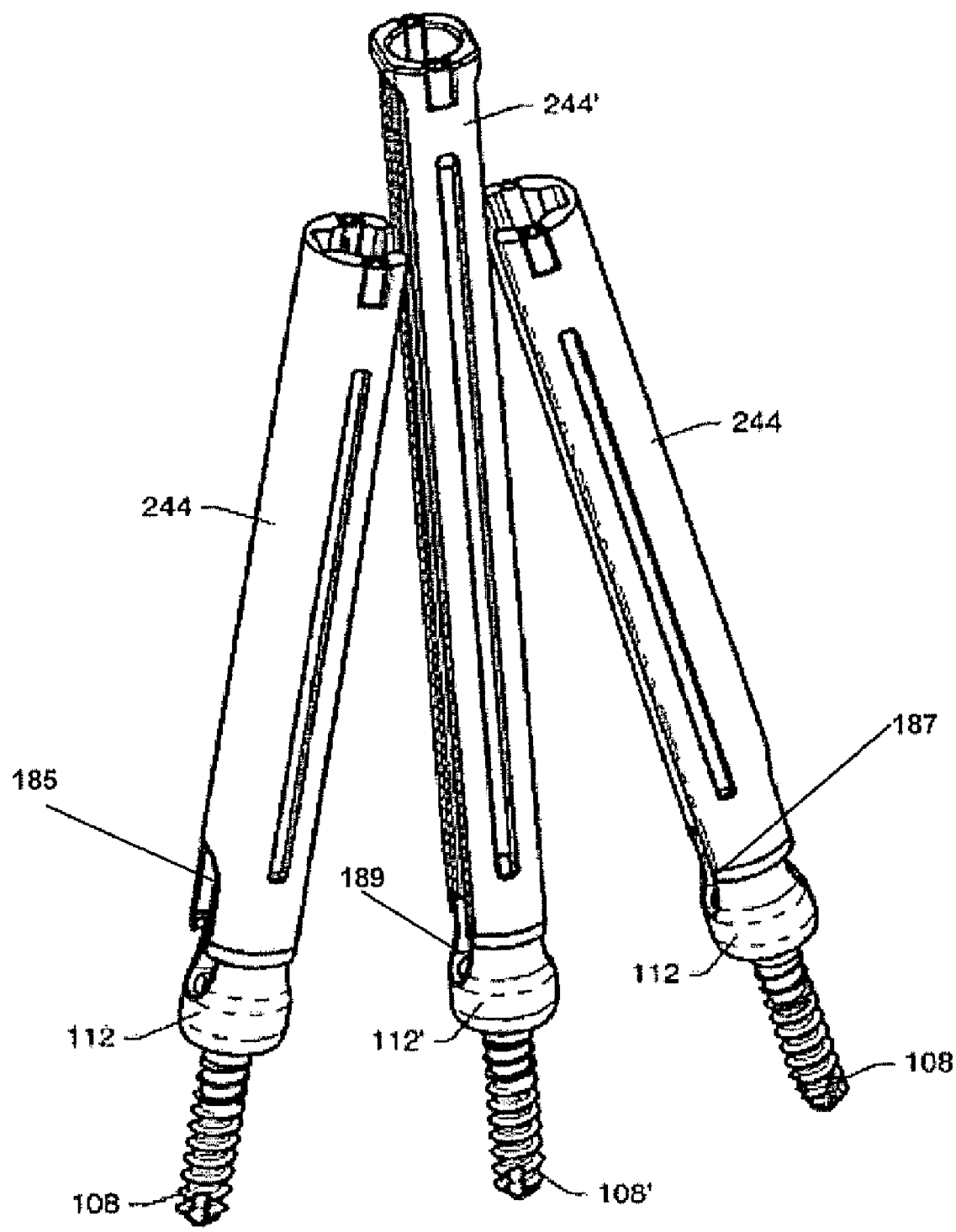
FIG. 48 depicts a perspective view of an embodiment of sleeves coupled to bone fastener assemblies.

When bone fasteners of polyaxial bone fastener assemblies are positioned in vertebral bone, detachable members coupled to collars of the bone fastener assemblies may be moved in desired positions. During surgery, a detachable member in a patient may be oriented towards an adjacent vertebra that is to be stabilized to reduce the required incision size. In some embodiments, channels of the detachable members may be aligned so that an elongated member may be positioned in collars of the bone fastener assemblies. FIG. 48 depicts an orientation of three sleeves. Sleeves 244, 244' may couple to collars 112, 112' to form sleeve-collar assemblies. Bone fasteners 108, 108' may be inserted into vertebrae. Single-channel sleeves 244 may be coupled to collars 112 before insertion of bone fasteners 108 into two outer pedicles to be stabilized. Multi-channel sleeve 244' may be coupled to collar 112' before insertion of bone fastener 108' into a central pedicle of the three adjacent pedicles. Single-channel sleeves 244 may be angled towards multi-channel sleeve 244'. In certain embodiments, multi-channel detachable members may be coupled to all three pedicles. In other embodiments, differently shaped detachable members (e.g., circular, oval) may be used in one or more of the pedicles. Channels of the detachable members may be aligned so that an elongated member may be moved down the detachable members and into collars of the bone fastener assemblies.

FIG. 48 shows opening 185 on the non-channel side of single channel sleeve 244, opening 187 on the channel side of single-channel sleeve 244 and opening 189 in multi-channel sleeve 244'. While only one opening is indicated on each sleeve, each single channel sleeve 244 can include an opening 185 aligned with an opening 187 and multi-channel sleeve 244' can include two openings 189 aligned with each other. For a single-channel sleeve 244, the opening 187 (the opening on the channel side) may be formed by channel 248 and slot 160 of collar 112 while the opening 185 (the opening on the non-channel side) may be created by a notch 189 in sleeve 144 and slot 150. Notch 189 may extend upward from slot 150 to create an opening having any suitable shape. For multi-channel sleeve 244', the opening 189 on each side of multi-channel sleeve 244' can be formed by slot 150 and the channels 248 on either side of sleeve 244'. The openings can have a variety of shapes including, but not limited to, an elongated opening of constant width, an elongated opening of variable width, a rectangular opening, a trapezoidal opening, a circular opening, a square opening, an ovoid opening, an egg-shaped opening, a tapered opening, and combinations and/or portions thereof. In some embodiments, a first portion of the opening may have different dimensions than another portion of the opening. While the openings 185, 187 and 189 are shown as being partially formed by a collar 112/112' and a respective sleeve 244/244', the openings can be formed entirely by a collar 112/112' or entirely by a sleeve 244/244'.

Figure 49:
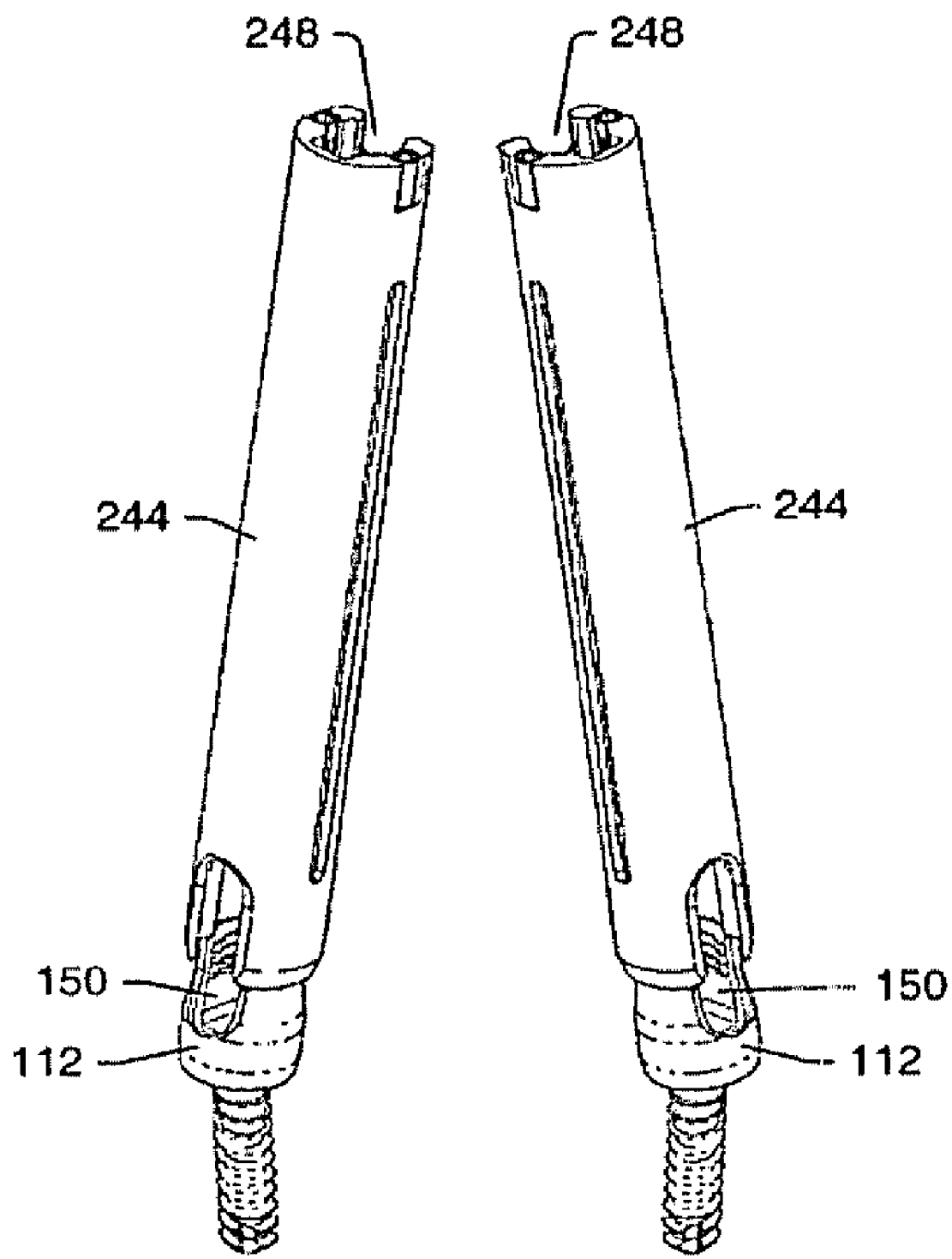
FIG. 49 depicts a perspective view of an embodiment of sleeves that are coupled to bone fastener assemblies.

In some embodiments, channels of detachable members may face a direction other than toward each other. FIG. 49 depicts sleeves 244 coupled to collars 112 oriented at an angle so that channels 248 of sleeves 244 face in different directions. An elongated member may be curved in an appropriate shape to engage slots 150 in collars 112 when channels 248 of sleeves 244 are angled. In some embodiments, channels in the detachable member may not be longitudinal channels down the length of the detachable member. In embodiments of detachable members with non-longitudinal channels, the channels of two adjacent detachable members may not face towards each other when the openings of collars coupled to the detachable members are aligned.

Figure 50:
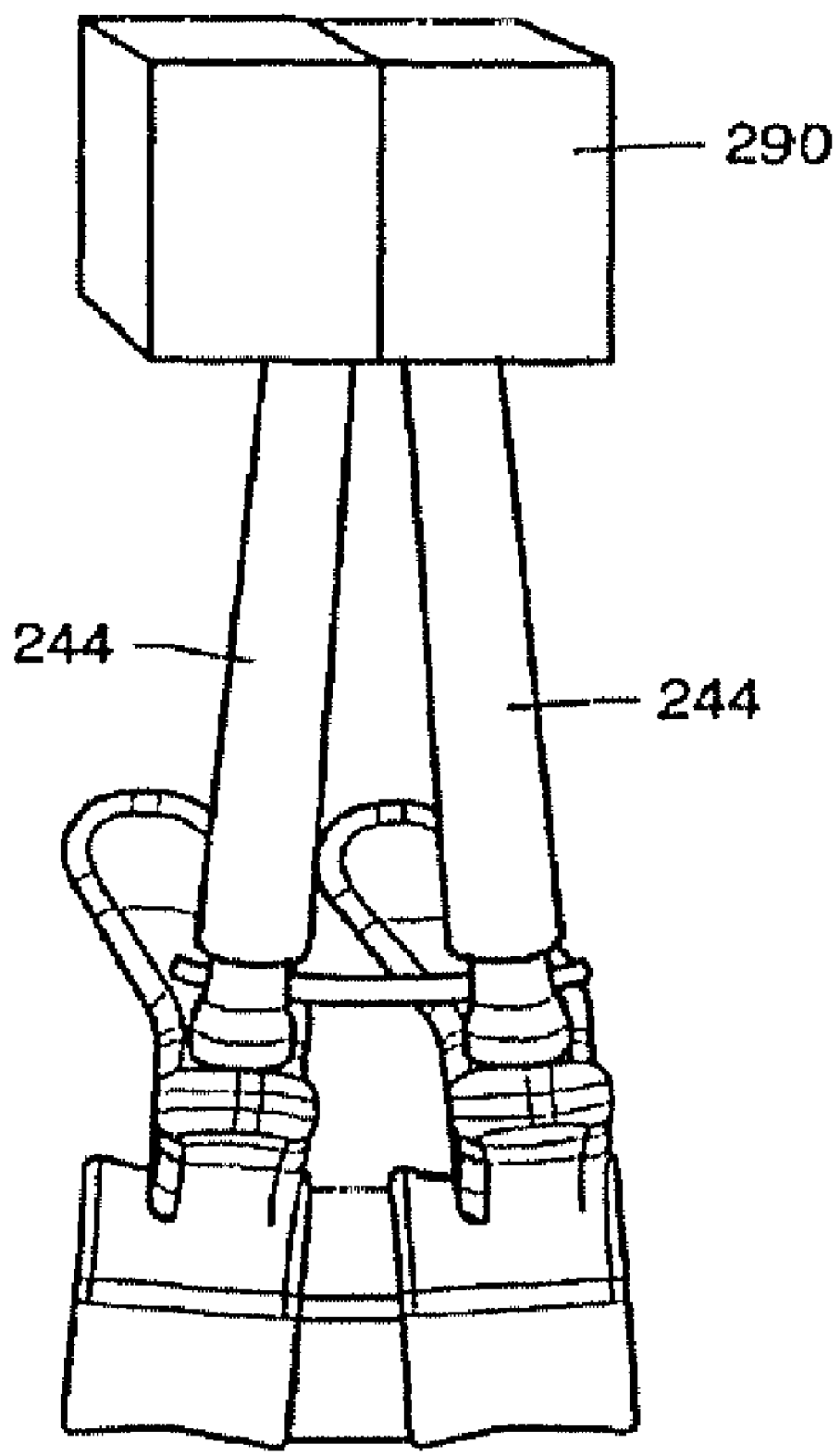
FIG. 50 depicts a schematic view of sleeve embodiments that are coupled to an embodiment of a frame.

In an embodiment, a frame may couple to two or more detachable members. FIG. 50 depicts a perspective view of sleeves 244 coupled to frame 290. As used herein, a "frame" includes any of a variety of structural elements including, but not limited, rods, bars, cages, or machined blocks. In some embodiments, frame 290 may provide a rigid coupling between sleeves 244. In other embodiments, frame 290 may allow for angular or translational movement between sleeves. For example, frame 290 may include slidable elements that allow sleeves to be translated toward each other or away from each other to facilitate compression or distraction of vertebrae. Alternatively, frame 290 may enable sleeves 244 to pivot toward each other or away from each other. In some embodiments, frame 290 may allow for movement of sleeves 244 to facilitate spinal reduction.

After a bone fastener assembly is coupled to a detachable member, a driver may be coupled to a bone fastener of the bone fastener assembly. The driver may be used to insert the bone fastener into vertebral bone.

Figure 51:
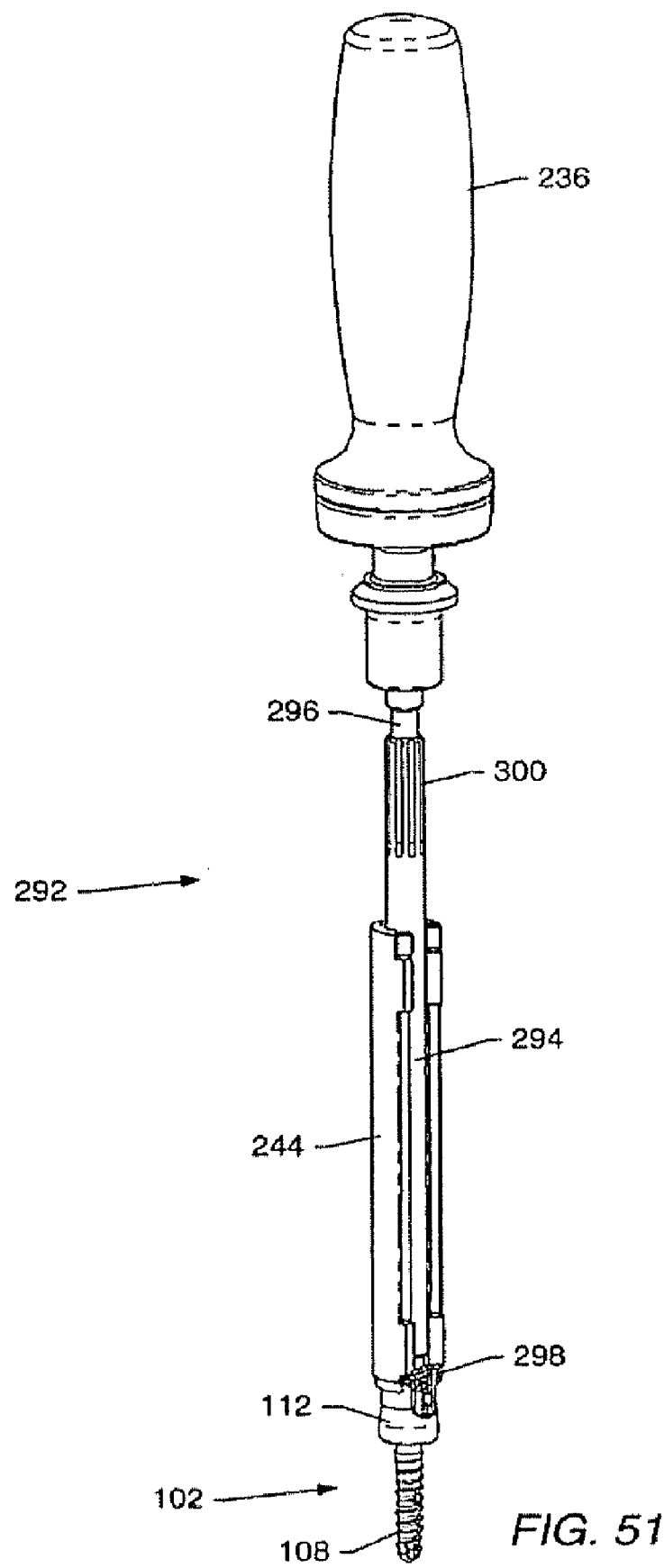
FIG. 51 depicts a perspective view of an embodiment of a driver coupled to a bone fastener and a sleeve.

FIG. 51 depicts an embodiment of driver 292 positioned in sleeve 244. Sleeve 244 is coupled to bone fastener assembly 102. Driver 292 may be coupled to collar 112 and to bone fastener 108 of bone fastener assembly 102. Coupling driver 292 to collar 112 and to bone fastener 108 may ensure proper alignment of the driver relative to the bone fastener. Coupling driver 292 to collar 112 and to bone fastener 108 may also inhibit movement of the collar relative to the bone fastener during insertion of the bone fastener.

Driver 292 may include outer shaft 294, inner shaft 296, and removable handle 236. Outer shaft 294 may include threading 298 and textured portion 300. A portion of outer shaft 294 may be positioned in a passage through sleeve 244 (passage 250 shown in FIG. 30). Threading 298 may couple to a modified thread of collar 112. Textured portion 300 may facilitate rotation of outer shaft 294 so that threading 298 engages the modified thread of collar 112. When threading 298 engages the modified thread of collar 112, driver 292 may be securely coupled to bone fastener assembly 102, which is securely fastened to sleeve 244.

A distal end of inner shaft 296 may be coupled to bone fastener 108 during use. Inner shaft 296 may be coupled at a proximal end to removable handle 236 during use. Inner shaft 296 may be rotatable relative to outer shaft 294 so that bone fastener 108 can be inserted into vertebral bone. A proximal portion of inner shaft 296 may include at least one flat portion that fits in a mating portion of removable handle 236. Removable handle 236 may be the same removable handle that is used with a bone tap that forms a threaded opening in vertebral bone for a bone fastener. Removable handle 236 may be removed from driver 292 during insertion of a guide wire through the driver so that the guide wire may be held in at least one place at all times. In some embodiments, a removable handle for the driver may be unnecessary given the length of the guide wire and/or the length of the driver (e.g., a long guide wire and/or a short driver).

Figure 52:
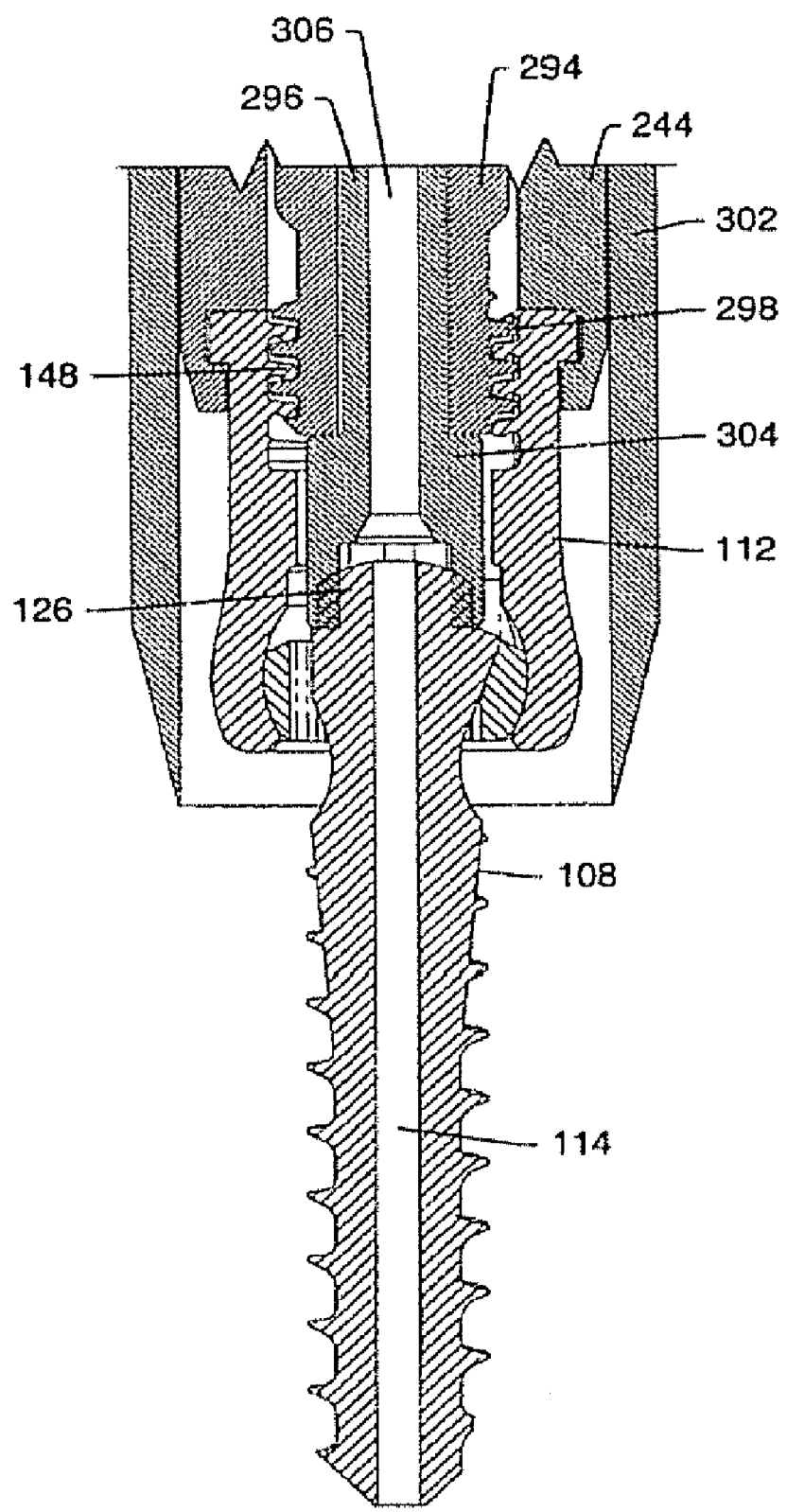
FIG. 52 depicts a partial cross-sectional view of an embodiment of a bone fastener and collar coupled to a driver positioned in a dilator.

FIG. 52 depicts a cross-sectional representation of a portion of an embodiment of a driver that is coupled to bone fastener 108 and collar 112 of a bone fastener assembly. Collar 112 is coupled to sleeve 244. Sleeve 244 is positioned in dilator 302. In some embodiments, clearance between outer shaft 294 and sleeve 244 may be relatively small. In some embodiments, the clearance between outer shaft 294 and sleeve 244 may range from about 0.1 mm to about 0.75 mm. For example, the clearance between outer shaft 294 and sleeve 244 may be about 0.25 mm (i.e., an inner diameter of the sleeve may be about 0.5 mm greater than an outer diameter of the outer shaft). Also, clearance between sleeve 244 and dilator 302 may be relatively small. The small clearances may inhibit undesired movement of the instruments relative to each other and/or reduce bulkiness at the surgical site.

Thread 298 of outer shaft 294 of the driver may couple to modified thread 148 of collar 112. Head 304 of inner shaft 296 of the driver may couple to tool portion 126 of bone fastener 108. Head 304 may have a complementary shape to tool portion 126 of bone fastener 108. A guide wire may be inserted into a distal end of passage 114 of bone fastener 108 and through passage 306 of the driver. When the guide wire is inserted into passage 114 and passage 306, a removable handle may not be coupled to inner shaft 296.

During a minimally invasive surgical procedure, a plane may be created in tissue from a first vertebra to a second vertebra. An elongated member may be positioned in the plane during the surgical procedure. In some embodiments, a tissue plane may be formed using a targeting needle. The targeting needle may be positioned at the first vertebra. The distal end of the needle may be moved toward the second vertebra to form the plane while maintaining a position of the needle at a surface of the skin. The needle may be moved back and forth a number of times to clearly establish the plane. Care may need to be taken to avoid bending the targeting needle during establishment of the plane.

Figure 53:
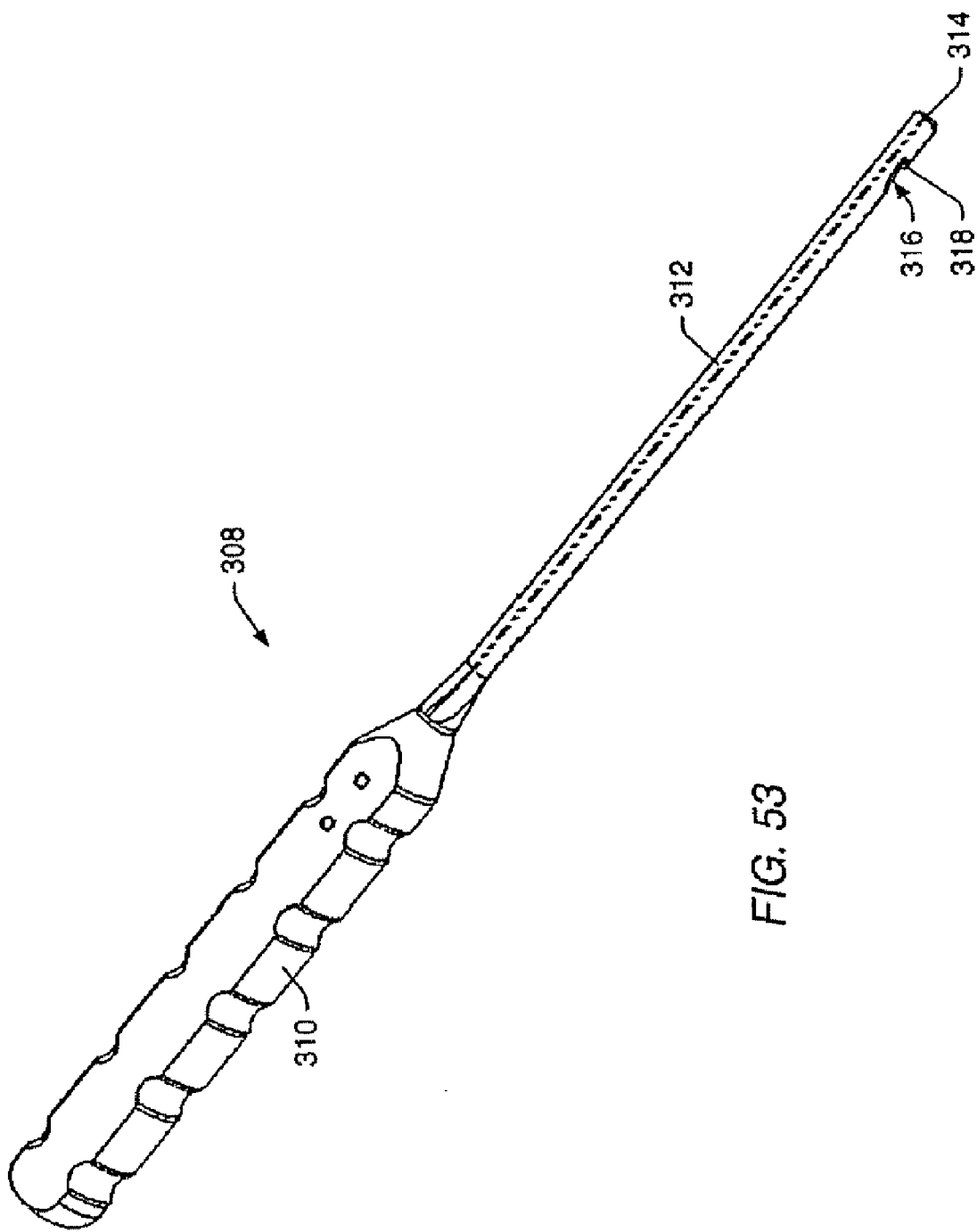
FIG. 53 depicts a perspective view of an embodiment of a tissue wedge.

In some embodiments, a tissue wedge may be used to form a plane in tissue between a first vertebra and a second vertebra. FIG. 53 depicts an embodiment of tissue wedge 308. Tissue wedge 308 may include handle 310 and blade 312. Handle 310 may allow blade 312 to be easily positioned at a desired location.

Blade 312 may be a double-wedged blade. Blade 312 may have a diamond-like shape. Edges of blade 312 may be blunt to avoid severing tissue during use of tissue wedge 308. Distal end 314 of blade 312 may be rounded. A shape of distal end 314 may inhibit damage to tissue and may facilitate movement of blade 312 towards a target location during formation of a plane in tissue between vertebrae. In some tissue wedge embodiments, tissue wedge 308 may include hook 316. Cutting edge 318 in hook 316 may be used to sever portions of tissue (e.g., fascia) through which blade 312 cannot form a plane. Cutting edge 318 may be oriented in blade 312 so that severing of tissue results when tissue wedge 308 is pulled away from the spine.

Figure 54:
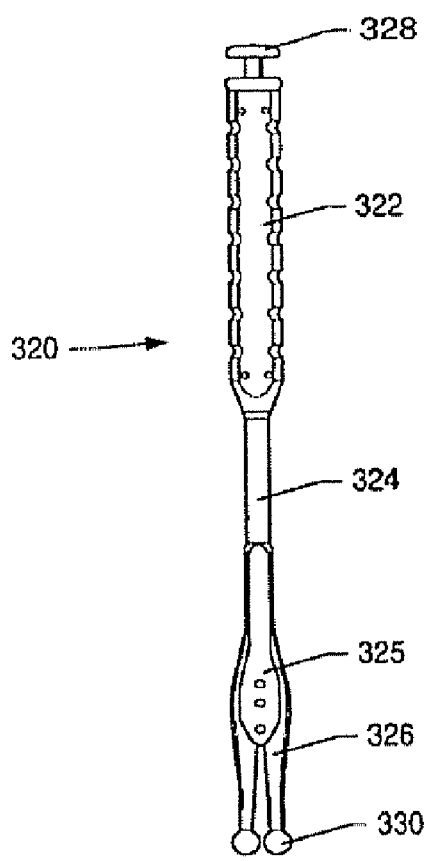
FIG. 54 depicts a perspective view of an embodiment of an estimating tool.

An estimating tool may be used to estimate a distance between bone fastener assemblies anchored in vertebrae. The bone fastener assemblies may be part of a single-level or multi-level spinal stabilization system. The distance estimated by an estimating tool may be used to determine a desired length of an elongated member to be positioned in collars of the anchored bone fastener assemblies. FIG. 54 depicts an embodiment of estimating tool 320 with handle 322 and shaft 324. Arms 326 may be pivotably coupled to coupling portion 325 of shaft 324. Distal ends of arms 326 may be rounded. In some embodiments, distal ends of arms 326 may include members 330. Members 330 may be rounded (e.g., spherical) or elongated (e.g., tubular). Members 330 may also have other shapes to meet specific needs or requirements. In embodiments, a shape and/or a size of members 330 may be designed to fit snugly into detachable members coupled to a spinal stabilization system.

Activator 328 may be located at a proximal end of handle 322. With activator 328 unengaged, a biasing element (e.g., a spring, springs, and/or elastic member) in coupling portion 325 may allow arms 326 to assume a fully extended position. With arms 326 in a fully extended position, members 330 may achieve a maximum separation distance. Estimating tool 320 may be designed such that a maximum separation distance of members 330 exceeds an expected distance between anchored bone fastener assemblies. Fully extended arms 326 may be manually compressed and inserted into passages of sleeves coupled to anchored bone fastener assemblies. For a multi-level system, arms 326 may be inserted in detachable members coupled to the outermost bone fastener assemblies while one or more detachable members coupled to one or more inner vertebrae are held out of the way. With activator 328 unengaged, the biasing element in coupling portion 325 may force members 330 against inner walls of the detachable members.

Estimating tool 320 may be advanced toward the anchored bone fastener assemblies. In some embodiments, estimating tool 320 may be advanced toward the anchored bone fastener assemblies until members 330 contact collars and/or bone fasteners of the bone fastener assemblies. With members 330 contacting collars and/or bone fasteners, activator 328 of estimating tool 320 may be engaged. Engaging activator 328 of estimating tool 320 may limit the biasing element such that the distance between outer surfaces of members 330 does not exceed the distance between the anchored bone fastener assemblies. With activator 328 engaged and the distance between outer surfaces of members 330 fixed to indicate the distance between the anchored bone fastener assemblies, estimating tool 320 may be moved upwards to remove the estimating tool from the patient. When estimating tool 320 is moved upwards, arms 326 may compress to facilitate removal of the estimating tool from the detachable members.

Once removed from the detachable members, the biasing element may restore the distance between outer surfaces of members 330 to indicate the separation between anchored bone fastener assemblies. The distance between members 330 (e.g., the distance between outer surfaces of the members) may be used to estimate a length of an elongated member needed to couple the anchored bone fastener assemblies. The distance between members 330 may be read using a scale provided in the instrumentation kit. In some embodiments, the scale may be indicia or etching on a surface of the instrumentation kit. In an embodiment, a length of an elongated member may be chosen to be greater than a distance between members 330 to allow for bending of the elongated member and/or to allow the elongated member to extend beyond the collars of the anchored bone fastener assemblies. For example, 15 mm may be added to the distance between members 330. In some embodiments, a length of an elongated member may be chosen such that the elongated member extends 2 mm or more beyond the collars. In certain embodiments, a length of an elongated member may be chosen such that ends of the elongated member do not extend from the collars.

Figure 55:
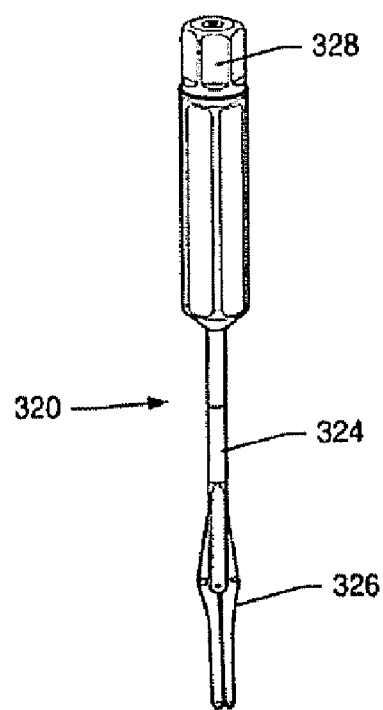
FIG. 55 depicts a perspective view of an embodiment of an estimating tool.

In the embodiment shown in FIG. 55, arms 326 of engaging tool 320 may be substantially parallel to each other and/or touching each other with activator 328 unengaged. Engaging activator 328 may cause separation of arms 326 at an angle, such that a distance between distal ends of the arms is greater than a distance between proximal portions of the arms. Estimating tool 320 may be inserted (e.g., with arms 326 together) in detachable members coupled to bone fastener assemblies anchored in vertebral bone. Activator 328 may be engaged and activated until arms 326 extend through channels of the detachable members and contact inner surfaces of the detachable members. Arms 326 may contact bone fasteners in the bone fastener assemblies. With arms 326 extended to meet resistance in the detachable members, estimating tool 320 may be withdrawn from the detachable members. During withdrawal of estimating tool 320 from the detachable members, arms 326 may be compressed toward each other as the estimating tool is moved up the detachable members and out of the body. After withdrawal of estimating tool 320 from the detachable members, arms 326 may extend back to the separation achieved when the arms were touching the bone fasteners. The distance between extended arms 326 may be used to estimate a length of an elongated member needed to couple the anchored bone fastener assemblies.

Figure 56:
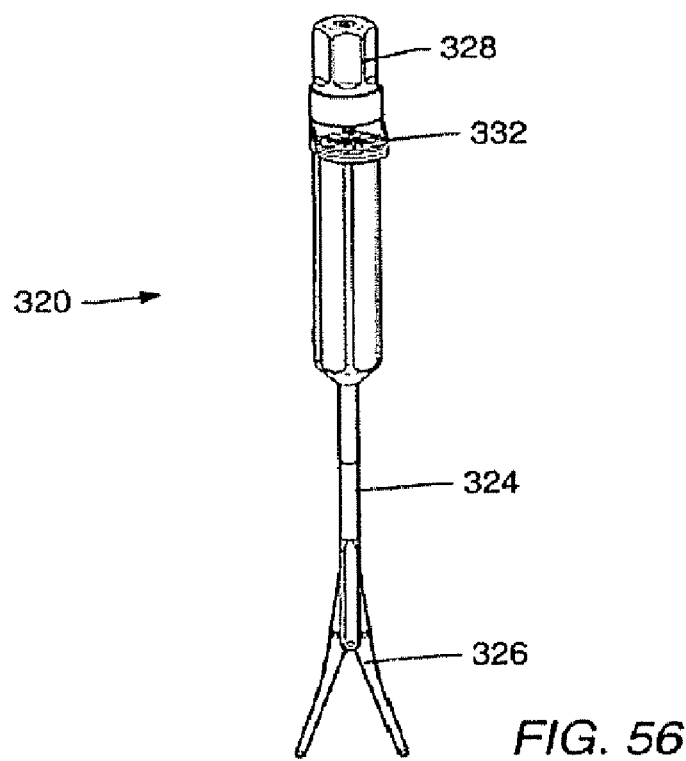
FIG. 56 depicts a perspective view of an embodiment of an estimating tool.

In some embodiments, an estimating tool may include a gage. FIG. 56 depicts an embodiment of estimating tool 320 with gage 332. With arms 326 of estimating tool 320 positioned together, gage 332 may have or may be set to a zero reading. With arms 326 extended to meet resistance in sleeves 244, gage 332 may provide an estimate of the distance between the sleeves. The distance between the sleeves may be used to estimate a length of an elongated member needed to couple the anchored bone fastener assemblies. In an embodiment, a length of an elongated member may be chosen to be greater than the distance measured by a gage to allow the elongated member to extend beyond slots of collars of anchored bone fastener assemblies.

Figure 57:
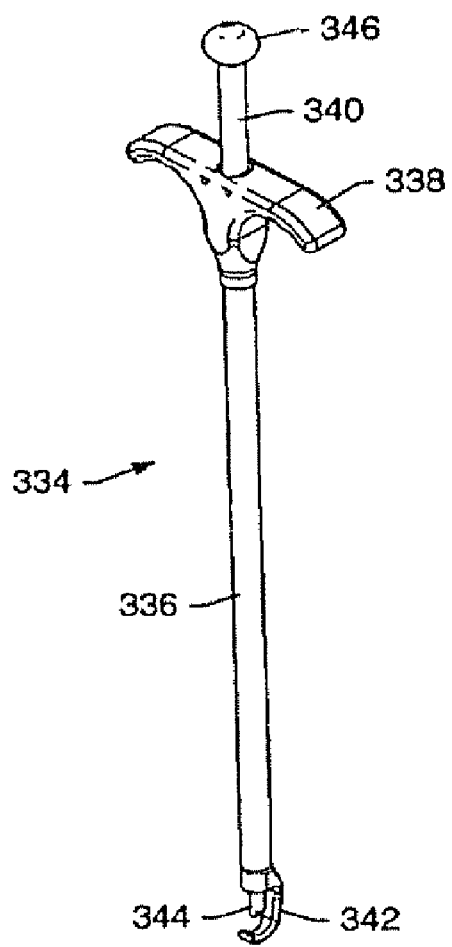
FIG. 57 depicts a perspective view of a tool designed to position an elongated member proximate vertebrae.

In some embodiments, an elongated member positioner may be used to guide an elongated member through detachable members and to position the elongated member in collars proximate pedicles of vertebrae. FIG. 57 depicts an embodiment of elongated member positioner 334. Elongated member positioner 334 may include outer shaft 336, handle 338, inner shaft 340, and grasping member 342. In some embodiments, grasping member 342 may be a hook. A first end (i.e., proximal end) of outer shaft 336 may be connected to handle 338. A second end (i.e., distal end) of outer shaft 336 may be coupled to grasping member 342. Inner shaft 340 may pass through handle 338 and outer shaft 336. A second end (i.e., distal end 344) of inner shaft 340 may contact an elongated member positioned in grasping member 342. A first end (proximal end 346) of inner shaft 340 may extend from handle 338. Proximal end 346 of inner shaft 340 may be a knob or a thumb plate. An amount of force applied to an elongated member positioned between grasping member 342 and distal end 344 of inner shaft 340 may be controlled by the amount of pressure applied to proximal end 346 of inner shaft 340. Pressure may be applied to proximal end 346 of inner shaft 340 manually or mechanically. Mechanical means of applying pressure to proximal end 346 of inner shaft 340 include, but are not limited to, forceps handles and an adjustable rotor.

Distal end 344 of inner shaft 340 may be positioned proximate grasping member 342. An elongated member may be positioned between grasping member 342 and distal end 344 of inner shaft 340 of positioning tool 334 before or after initial insertion of the elongated member into a sleeve. The elongated member may be held between grasping member 342 and distal end 344 of inner shaft 340 with pressure applied to proximal end 346 of the inner shaft. Distal end 344 of inner shaft 340 may be contoured (e.g., curved) to allow some motion (e.g., rocking motion) of the elongated member while the elongated member is coaxed into position with positioning tool 334. During some installation procedures, positioning tool 334 may remain coupled to an elongated member until the elongated member is secured in collars of anchored bone fastener assemblies with closure members.

In some cases, pressure supplied to an elongated member with an elongated member positioner may not be sufficient to seat the elongated member in a collar. A seater may be used in conjunction with an elongated member positioner to maneuver an elongated member into one or more collars. During some procedures, an elongated member positioner may be removed from the elongated member before using the seater. During some procedures, the elongated member positioner may remain attached to the elongated member until closure members are secured to bone fastener assemblies to form a spinal stabilization system.

Figure 58:
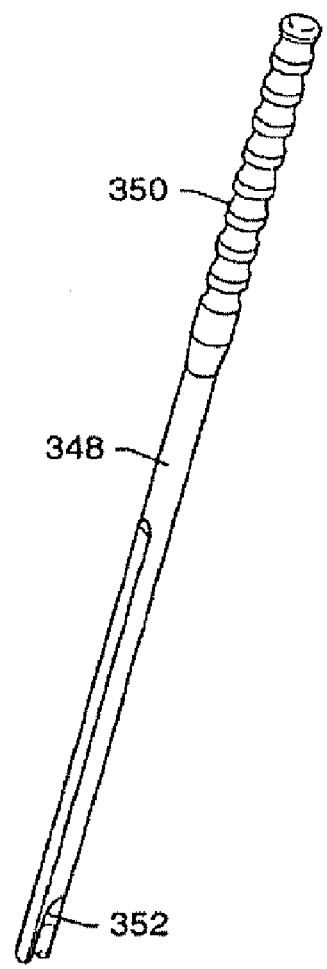
FIG. 58 depicts a perspective view of a seater for placing an elongated member proximate vertebrae.
Figures 59A, 59B:
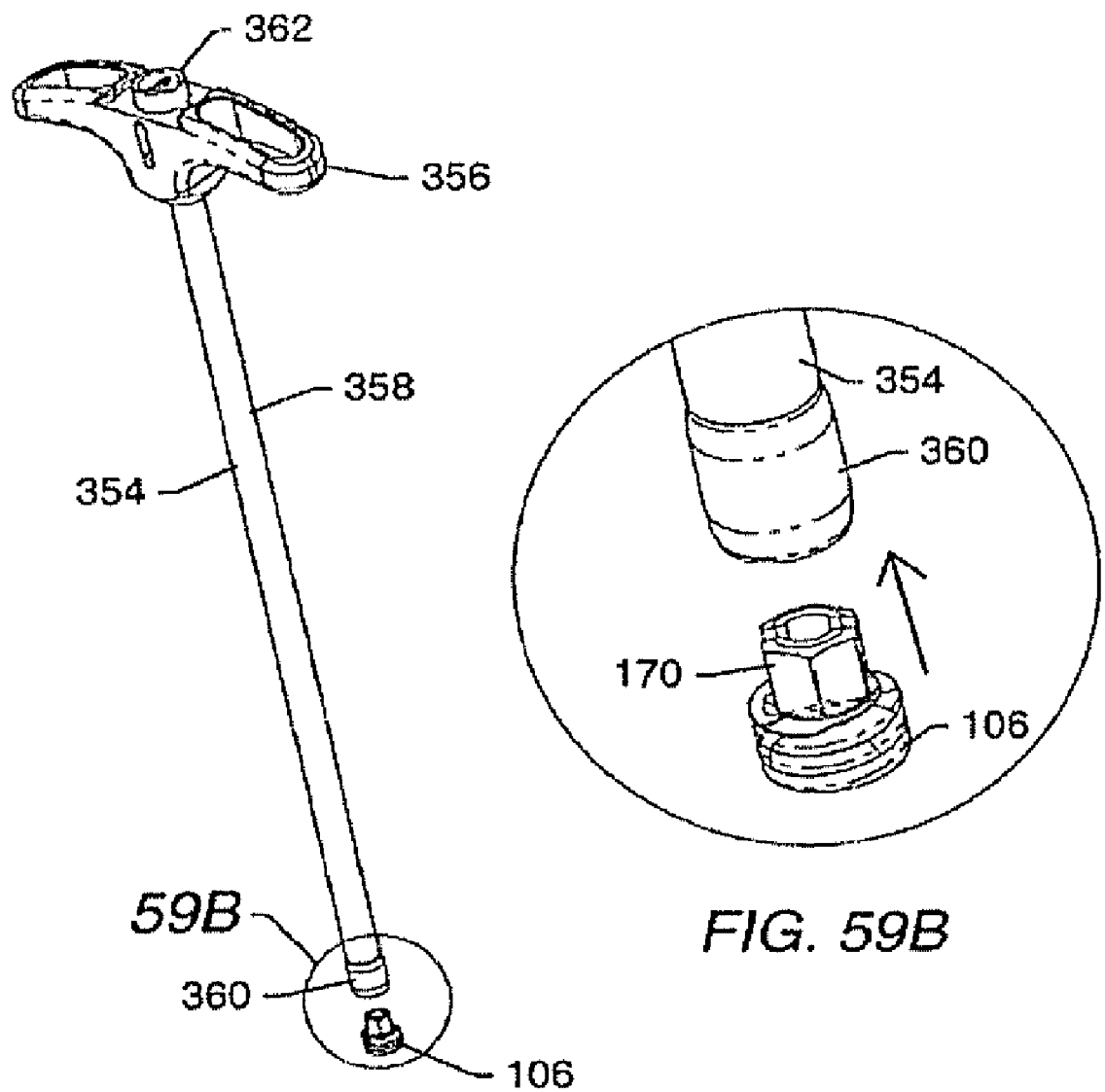
FIGS. 59A and 59B depict perspective views of a tool designed to position a closure member in a collar coupled to a bone fastener.

Seater 348, shown in FIG. 58, may include handle 350 and groove or grooves 352. A portion of an elongated member to be positioned in collars may fit in grooves 352. In an embodiment, an elongated member positioner may be used to align an elongated member proximate slots in one or more collars coupled to pedicles of vertebrae. Groove 352 of seater 348 may be positioned at a desired position along a length of the elongated member. A user may apply downward force with handle 350 to seat the elongated member in a collar as the elongated member positioner is used to guide the elongated member into position. After an elongated member has been positioned and seated in collars as desired, closure members may be used to secure the elongated member to the collars. FIGS. 59A and 59B depict perspective views of driver 354. Driver 354 may be used to position a closure member in a collar of a bone fastener assembly. As shown in FIG. 59A, driver 354 may include handle 356, elongated portion 358, and coupling portion 360. Coupling portion 360 may be used to engage closure member 106. Coupling portion 360 may engage tool portion 170 of closure member 106, shown in FIG. 59B. In some embodiments, driver 354 may include an inner shaft. The inner shaft may couple the closure member to driver 354. The inner shaft may couple to the tool portion of the closure member so that the tool portion is securely held after the tool portion is sheared from the closure member. In some embodiments, an end of inner shaft may be press fit into the tool portion. In some embodiments, the inner shaft may include a threaded end portion that engages a mating thread in the tool portion. Rotation of the inner shaft may allow closure member 106 to be locked in coupling portion 360 of driver 354. Knob 362 may be used to rotate the inner shaft.

FIG. 60A depicts driver 354 with coupled closure member 106 positioned for insertion in sleeve 244. After insertion of driver 354 in sleeve 244, closure member 106 may be positioned proximate collar 112. With driver 354 positioned in sleeve 244, as shown in FIG. 60B, the driver may be rotated to advance closure member 106 in collar 112 and secure elongated member 104 to the collar. When closure member 106 is snug and elongated member 104 is secured, driver 354 may be disengaged from the closure member and removed from sleeve 244. In an embodiment, driver 354 may be used to shear off the tool portion of secured closure member 106. In some embodiments, the coupling portion of the driver may capture the sheared tool portion of the closure member. In certain embodiments, driver 354 may include a mechanism to dislodge a closure member and/or a tool portion of a closure member from the distal end of the driver.

Figure 61:
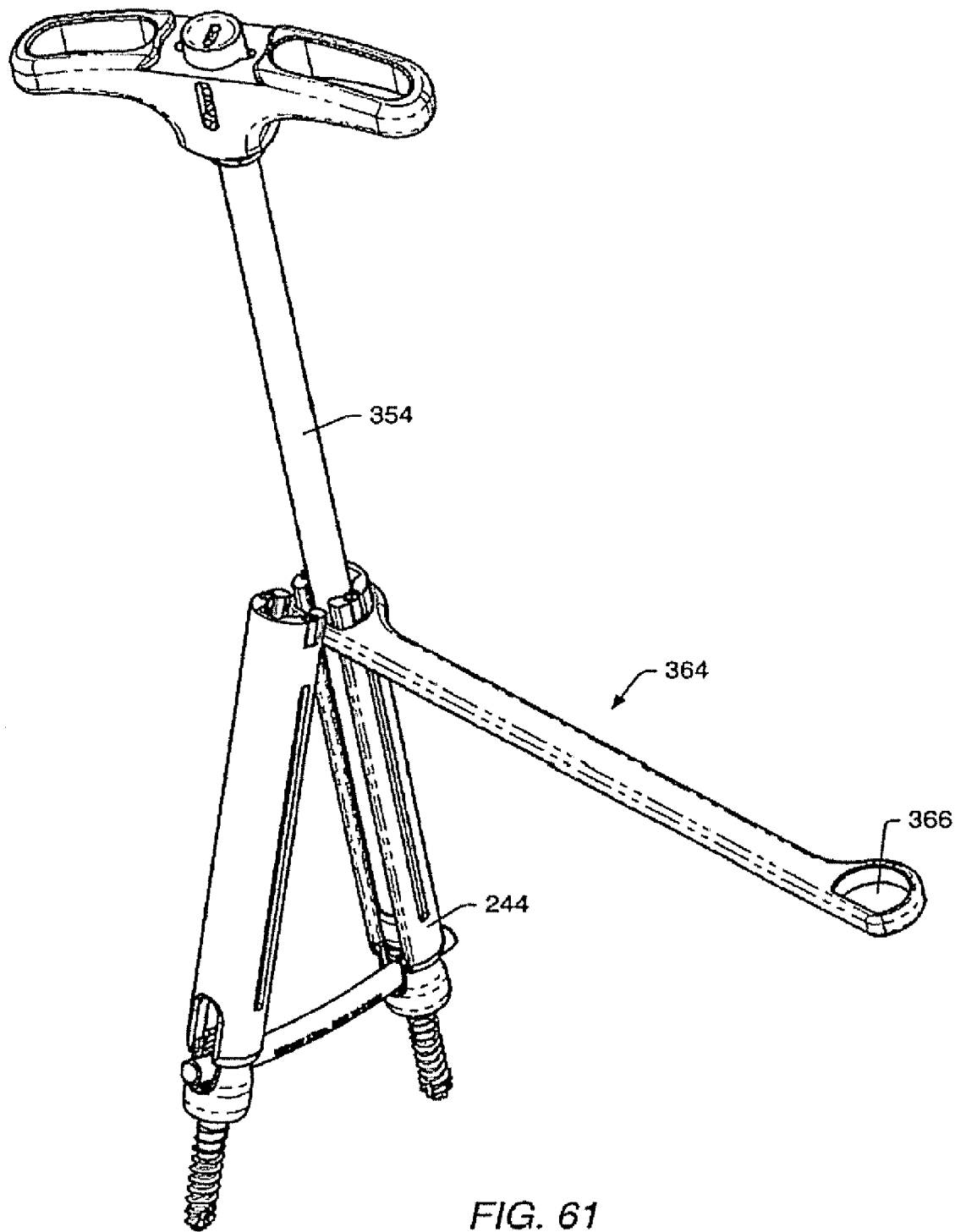
FIG. 61 depicts an embodiment of a counter torque wrench coupled to a sleeve.

In some embodiments, a detachable member may be held with a counter torque wrench as the tool portion of a closure member is sheared off. In an embodiment, about 90 in-lbs of torque may be required to shear off the tool portion of a closure member. A counter torque wrench may inhibit transfer of force to the patient when a closure member is being secured to a collar. FIG. 61 depicts an embodiment of counter torque wrench 364 used to inhibit application of torque to a patient's spine during shearing of a tool portion of a secured closure member. Sleeve 244 may fit in opening 366 of counter torque wrench 364. Counter torque wrench 364 may be positioned near a proximal end of sleeve 244 during use. Force may be applied to counter torque wrench 364 in a direction opposite to rotational force applied to driver 354 to shear off the tool portion of a secured closure member. Opening 366 in torque wrench 364 may be of any shape to accommodate a cross-sectional shape of sleeve 244 and inhibit rotation of the sleeve during use.

Figure 63:
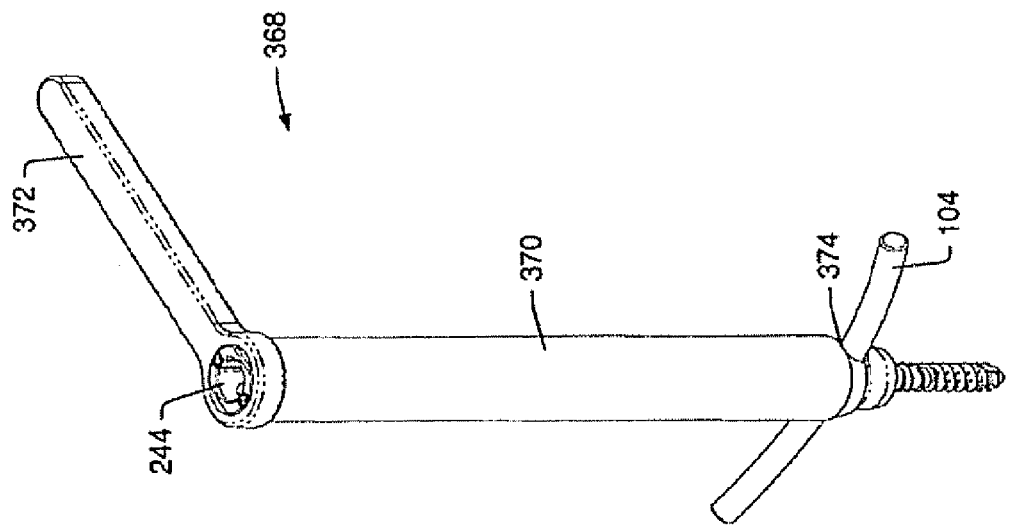
FIG. 63 depicts a schematic view of the counter torque wrench shown in FIG. 62 coupled to an elongated member.
Figure 62:
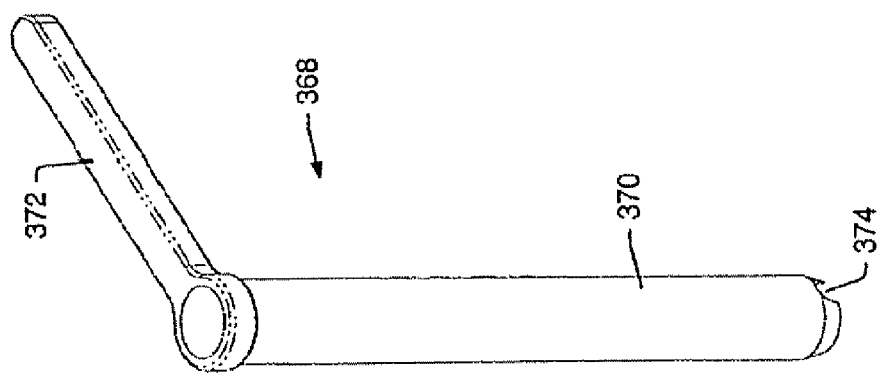
FIG. 62 depicts an embodiment of a counter torque wrench.

FIG. 62 depicts an embodiment of counter torque wrench 368 designed to accommodate sleeves. Counter torque wrench 368 may include hollow shaft 370 and handle 372. Groove 374 may be located at a distal end of hollow shaft 370. FIG. 63 depicts counter torque wrench 368 fitted over multi-channel sleeve 244. In an embodiment, hollow shaft 370 may be inserted through an opening in the body over sleeve 244 and advanced toward the spine until elongated member 104 is seated in groove 374. Counter torque wrench 368 may engage the spinal stabilization system. Force may be applied to counter torque wrench 368 in a direction opposite to rotational force applied to a driver used to shear off a tool portion of a secured closure member. During a minimally invasive spinal stabilization procedure, counter torque wrench 368 may be used with various types of detachable members, including single-channel sleeves and multi-channel sleeves.

Minimally invasive procedures may involve locating a surgical site and a position for a single skin incision to access the surgical site. The incision may be located above and between (e.g., centrally between) vertebrae to be stabilized. An opening under the skin may be enlarged to exceed the size of the skin incision. Movement and/or stretching of the incision, bending of an elongated member, and angulation of collars of bone fastener assemblies may allow the length of the incision and/or the area of a tissue plane to be minimized. In some embodiments, minimally invasive insertion of a spinal stabilization system may not be visualized. In certain embodiments, insertion of a spinal stabilization system may be a top-loading, mini-opening, muscle-splitting, screw fixation technique.

Insertion of a spinal stabilization system may include gradually increasing the diameter of an opening formed in a pedicle and/or vertebral body to accept a bone fastener assembly. For example, a targeting needle may have outer diameter of about D. A bone awl inserted after the targeting needle may have an outer diameter incrementally larger than the outer diameter of the targeting needle. As used herein, an incrementally larger diameter may be large enough to allow a snug but adjustable fit. For example, the bone awl may have outer diameter of about (D+x). A tap portion of a bone tap inserted after the bone awl may have a minor diameter of about (D+2x). A bone fastener may have a minor diameter of about (D+3x). In some embodiments, x may be between about 0.1 mm and about 1.0 mm. For example, x may be about 0.5 mm. Incremental sizing of the targeting needle, bone awl, tap, and bone fastener may promote a proper fit of the bone fastener in the vertebra to be stabilized.

In an embodiment of a spinal stabilization system insertion method, the patient may be placed in a prone position on a radiolucent table with clearance available for a C-arm of a fluoroscope. For example, a Jackson table with a radiolucent Wilson frame attachment may be used. The ability to obtain high quality images is very important. Bolsters, frames, and pads may be inspected for radiolucency prior to the operation. Placing the patient in a knee-chest position (e.g., using an Andrews table) should be avoided. Care should be taken to avoid placing the patient's spine in kyphosis during positioning of the patient.

The C-arm of the fluoroscope should be able to freely rotate between the anteroposterior, lateral, and oblique positions for optimal visualization of pedicle anatomy during the procedure. The arm should be rotated through a full range of motion prior to beginning the procedure to ensure that there is no obstruction or radio-opaque object in the way. The fluoroscope may be positioned so that Ferguson views and "bullseye" views are obtainable. Once the patient is positioned and the ability to obtain fluoroscopic images of the target levels for instrumentation has been confirmed, the patient may be prepared and draped sterilely.

For most of the lumbar region, the vertebral pedicle is an obliquely oriented cylindrical corridor. The angulation varies by approximately 5 degrees per level (e.g. L1: 5 degrees; L5: 25 degrees). A pre-operative fine-cut computed tomography image may be examined to determine any unique anatomy of the patient. Acquiring the pedicle in the most lateral and superior quadrant of the pedicle may be desirable to avoid the overriding facet during a minimally invasive procedure. A lateral entry point may allow for better screw convergence as well as less interference with the superior adjacent level facet joint. A targeting needle may be passed in a medial and inferior trajectory, thus following the natural pathway of the pedicle. Frequent fluoroscopic inspection in both an anteroposterior and lateral plane may ensure proper passage of the needle as the needle is inserted into vertebral bone.

Various techniques may be used to plan the skin incisions and entry points. In one embodiment, the planning sequence for a single-level stabilization may include the following four steps. First, an anteroposterior image may be obtained with the spinous processes centered at the target vertebral bodies. Vertical lines passing through midpoints of pedicles that are to receive bone fasteners may be marked on the patient. The lines do not represent skin entry points. The lines are markers of pedicle entry points used to estimate angles at which targeting needles to be inserted to contact the pedicles. In some embodiments, sets of vertical lines may be drawn corresponding to the lateral edges of the pedicles instead of lines corresponding to the midpoints of the pedicles.

Second, horizontal lines may be marked approximately through the centers of the pedicles (mid-pedicle lines) on the patient. In some embodiments, the lines may be drawn on the superior side of the center axes (superior to the mid-pedicle).

Third, an oblique or "bullseye" view (i.e., down a longitudinal axis of a pedicle) may be obtained on each side of the patient for each pedicle that is to be stabilized. Vertical oblique view lines may be marked on the skin at the midpoints of each of the pedicles that are to receive a bone fastener. The oblique view lines may be drawn in a different color than the vertical lines drawn during the first step. In some embodiments, vertical lines may be drawn corresponding to the lateral edges of the pedicles instead of lines corresponding to the midpoints of the pedicles.

The oblique view lines may be about 2 cm to about 3 cm away from the lateral pedicle border lines marked in the first step. For larger patients, the oblique view line may be greater than about 3 cm away from the midline marked in the first step. For smaller patients, the oblique view line may be closer than about 2 cm away from the midline marked in the first step. The intersection of the oblique view lines with the horizontal lines drawn in the second step may represent skin entry points for a targeting needle as the targeting needle passes through soft tissue at an angle towards the bony pedicle entry point. A side fluoroscopic image, the horizontal lines, and the vertical lines may help the surgeon triangulate between the skin entry points and bony entry points.

Fourth, an incision may be made in the skin between mid-pedicle lines along the vertical oblique view lines. The skin incision may be from about 2 cm to about 4 cm long. In some embodiments, the incision may be from about 2.5 cm to about 3 cm long. Limiting the length of the incision may enhance patient satisfaction with the procedure. The incisions may be pre-anesthetized with, for example, 1% lidocaine with 1:200,000 epinephrine. To blunt the pain response, a long spinal needle may be used to dock on the bone entry point and inject the planned muscle path in a retrograde fashion as well. Once the incision has been made, tissue surrounding the incision may be pulled and/or stretched to allow access to a target location in a vertebra.

After sterile preparation and draping, the pedicle entry points may be fluoroscopically rechecked to ensure that the previously marked lines correspond to the intersection of the midline of the transverse process and the lateral joint and pars interarticularis. The intersection of the facet and the transverse process provides a starting point that may help avoid the canal and follow the natural inclination of lumbar pedicles. For the spinal stabilization system described, in which sleeves coupled to bone fastener assemblies are substantially unconstrained by insertion angles of the bone fasteners, patient anatomy may determine the most advantageous insertion angles of the bone fasteners.

A scalpel may be used to make a stab wound at the junction of an oblique view line and a mid-pedicle line. In an embodiment, the scalpel may be a #11 scalpel. A targeting needle may be passed through the incision in an oblique lateral to medial trajectory towards the bony entry point defined by a lateral pedicle border line. The C-arm of the fluoroscope may be placed in an anteroposterior position for this maneuver.

As the targeting needle encounters the bony anatomy, anteroposterior fluoroscopic images may be used to place the tip of the needle at the upper outer quadrant of the pedicle. In some embodiments, the needle may be walked medially along the transverse process to the pedicle entry point. In some embodiments, the needle tip may be docked by lightly tapping the tip into the bone with a mallet or other impact device to drive the tip into the bone. In some embodiments, the needle tip may be docked by applying downward pressure to the targeting needle to force the tip into the bone.

The fluoroscope may then be moved to a lateral position. The surgeon may correct the sagittal trajectory of the needle by moving the needle in an anterior or posterior direction to match the vector of the pedicle corridor. In some embodiments, a mallet or other impact device may be used to gently advance the targeting needle into the pedicle halfway to the pedicle-vertebral body junction. In other embodiments, force may be applied to the targeting needle to drive the targeting needle into the pedicle halfway to the pedicle-vertebral body junction. An anteroposterior image may then be obtained to confirm that the needle is approximately halfway across the pedicle in the anteroposterior view. If the tip is more than halfway across the pedicle in a lateral to medial projection, the trajectory may be too medial. Further advancement of the needle may risk passing the needle through the spinal canal. The needle may be repositioned. A new starting point or new trajectory may be obtained. If the anteroposterior image demonstrates that the needle is significantly lateral in the pedicle, then the needle may have passed along the lateral portion of the pedicle. A needle that has passed along the lateral portion of the pedicle may be withdrawn and repositioned.

Once a good trajectory has been obtained, the targeting needle may be advanced using a mallet. In some embodiments, the needle may be pushed in without a mallet. The targeting needle may be advanced to the junction of the pedicle and vertebral body under lateral fluoroscopic guidance. FIG. 64A depicts targeting needle 198 advanced to the junction of pedicle 164. At this point, confirmation of position and trajectory should be repeated under anteroposterior fluoroscopy. Targeting needle 198 may be further advanced to a desired depth within vertebral body 166 using a mallet or applied force. FIG. 64B depicts targeting needle 198 advanced to the desired depth.

A scale on targeting needle 198 may be used to approximate a length of a bone fastener to be used. A first depth of targeting needle 198 may be measured relative to body surface 376 when pedicle 164 is first encountered. A second depth of targeting needle 198 may be measured relative to body surface 376 after the targeting needle has been advanced to the desired depth in vertebral body 166. An approximate length of the pedicle screw to be used may be determined by taking a difference between the depth measurements.

After targeting needle 198 has been advanced into the bone, member 202 of the targeting needle (shown in FIG. 64B) may be removed from the targeting needle. FIG. 64C depicts outer housing 200 with the member removed. After removal of the member, a guide wire may be placed through a passage in targeting needle 198 into vertebral body 166. FIG. 64D depicts targeting needle 198 with guide wire 218 positioned through the passage in the targeting needle. Lateral fluoroscopic images may be obtained to indicate the position of guide wire 218. In some embodiments, guide wire 218 may be pushed into vertebral body 166. In certain embodiments, guide wire 218 may be advanced about 1 cm beyond an end of outer housing 200 to secure the guide wire in vertebral body 166. In some embodiments, a small diameter tissue dilator may be placed over the guide wire and positioned on an upper surface of the targeting needle. The tissue dilator may provide stability to the guide wire. Added stability from the dilator may allow the guide wire to be successfully tapped into the vertebral body with a small mallet. Care should be taken to avoid kinking guide wire 218. After guide wire 218 is secured in vertebral body 166, outer housing 200 may be removed from the patient. FIG. 64E depicts guide wire 218 after removal of the targeting needle.

Once the guide wire has been passed through the targeting needle and the targeting needle has been removed, the guide wire may be used as a guide to position one or more successively sized dilators around a target location in a pedicle. A dilator may be a conduit with a regular shape (e.g., cylindrical) or an irregular shape (e.g., C-shaped). A dilator may form an opening through soft tissue to the pedicle. For patients with a thick fascia, it may be advantageous to make a nick in the fascia with a scalpel blade to facilitate passage of the dilators. The dilators may be passed sequentially over the guide wire.

The dilators may be rotated during insertion to facilitate dilation of surrounding tissue. The dilators may be inserted until the leading edges contact the pedicle. A distal end of a dilator may be tapered to facilitate positioning of the dilator proximate the pedicle. An instrumentation set for a spinal stabilization system may include two, three, four, or more successively sized dilators.

FIG. 65A depicts first dilator 302A positioned around guide wire 218. First dilator 302A may have an inner diameter just slightly larger than an outer diameter of guide wire 218. As used herein, "an inner diameter just slightly larger than an outer diameter" may mean that the inner diameter is between about 0.03 mm and about 10 mm greater than the outer diameter. For example, an inner diameter of first dilator 302A may be about 0.5 mm greater than the outer diameter of guide wire 218. FIG. 65B depicts second dilator 302B positioned around first dilator 302A. Second dilator 302B may have an inner diameter just slightly larger than an outer diameter of first dilator 302A. FIG. 65C depicts third dilator 302C and fourth dilator 302D and positioned around second dilator 302B. Third dilator 302C may have an inner diameter just slightly larger than an outer diameter of second dilator 302B. Fourth dilator 302D may have an inner diameter slightly larger than an outer diameter of third dilator 302C. Once fourth dilator 302D is in position, dilators 302A, 302B, 302C may be removed, starting with dilator 302A. Lengths of dilators in a successively sized set may decrease with increasing diameter to facilitate removal of the smaller dilators. Care should be taken to avoid dislodging guide wire 218 during insertion and removal of the dilators. FIG. 65D depicts fourth dilator 302D positioned around guide wire 218 following removal of dilators 302A, 302B, 302C.

After tissue dilation has been achieved, a large diameter dilator (e.g., third dilator 302C or fourth dilator 302D shown in FIG. 65C) may be used to guide a bone fastener assembly and/or insertion instruments toward a target location in a pedicle. FIGS. 66A-66F depict portions of a procedure for preparation of pedicle 164 and vertebral body 166 for receiving a bone fastener assembly. FIG. 66A depicts bone awl 222 positioned over guide wire 218 in dilator 302 such that a tip of the bone awl is on or near a surface of pedicle 164. Bone awl 222 may be driven downwards into pedicle 164 to breach cortical bone of the pedicle. FIG. 66B depicts a position of bone awl 222 after pedicle 164 has been breached. After pedicle 164 is breached, bone awl 222 may be removed from dilator 302. FIG. 66C depicts guide wire 218 and dilator 302 after removal of bone awl 222. In some embodiments, an initial passage may be formed in the pedicle and the vertebral body using a drill or a drill and tap combination.

Figure 66D:
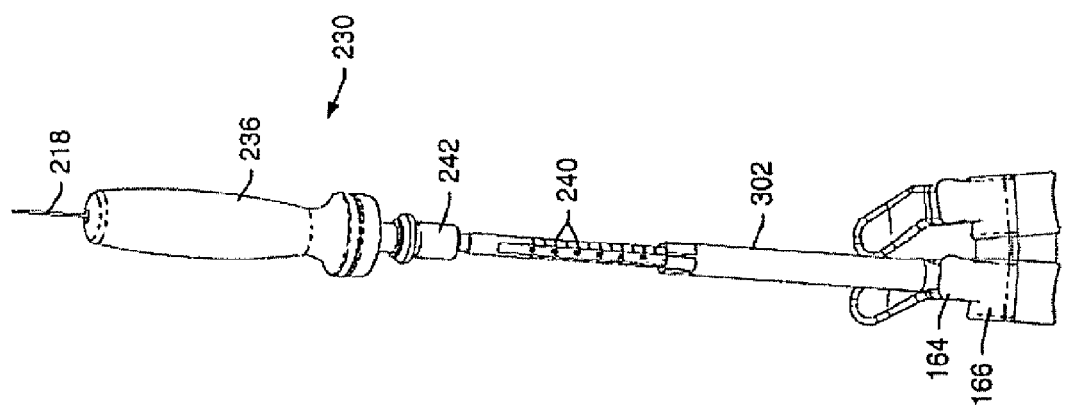
FIGS. 66A-66F depict schematic views of vertebra preparation for receiving a bone fastener assembly during a minimally invasive spinal stabilization procedure.
Figure 66C:
Figure 66B:
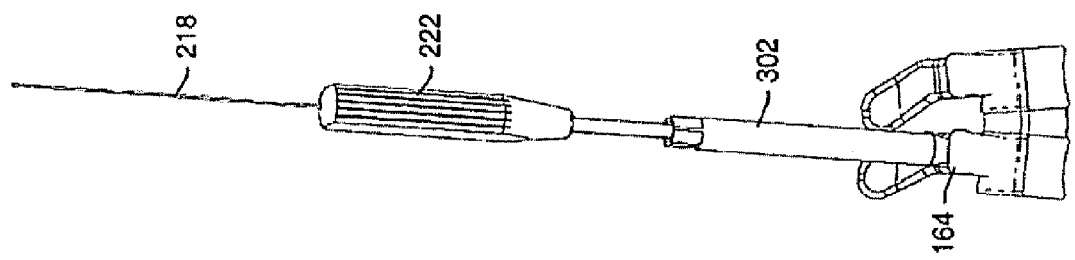
Figure 66A:
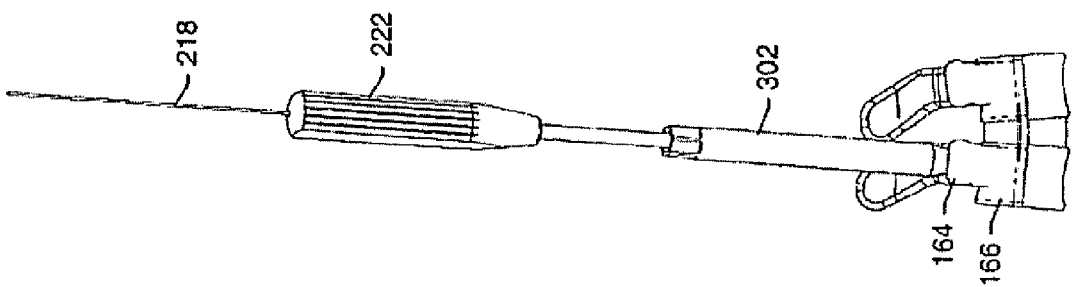

FIG. 66D depicts tap 230 positioned in dilator 302. After pedicle 164 is breached, tap 230 may be inserted over guide wire 218 into dilator 302. In an embodiment, dilator 302 may be third dilator 302C. Tap 230 may be sized to fit snugly inside third dilator 302C. In some embodiments, dilator 302 may be fourth dilator 302D. In certain embodiments, fourth dilator 302D may be inserted over third dilator 302C after bone has been tapped through the third dilator. Tapping through third dilator 302C rather than fourth dilator 302D may introduce less bulk at the target site of a pedicle during the tapping procedure. In some embodiments, an outer diameter of a sleeve coupled to a bone fastener assembly to be inserted in the pedicle may be substantially the same as an outer diameter of third dilator 302C.

Tap 230 may include removable handle 236 and indicia 240. Indicia 240 may be a scale. When tap 230 is positioned such that a first thread flight contacts pedicle 164, a first measurement of the position of the tap relative to a top of dilator 302 using indicia 240 may be noted. Tap 230 may be rotated to form a threaded passage through pedicle 164 and into vertebral body 166 to a desired depth. In some embodiments, a length of the threaded portion of tap 230 may be used to determine a depth of a threaded passage formed in a bone. For a threaded portion of a known length (e.g., 30 mm, 45 mm, 60 mm), a scaled image (e.g., X-ray image) of a depth of the threaded portion in a bone monitored during tapping may allow a medical practitioner to determine the depth of the threaded passage. In some embodiments, tap 230 may form threads of major diameter about 0.5 mm smaller than a major diameter of threads of a bone fastener to be inserted into the threaded passage.

Figure 66E:
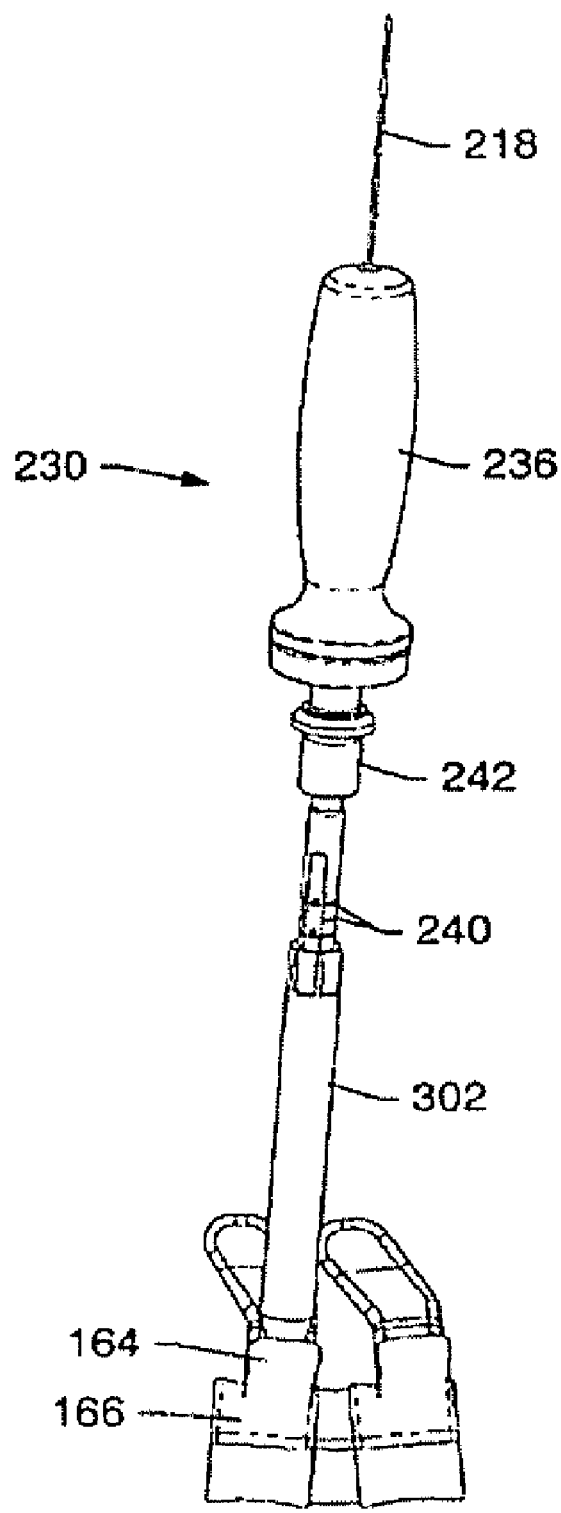

FIG. 66E depicts a position of tap 230 after a threaded passage of a desired length has been formed in pedicle 164 and vertebral body 166. Care should be exercised to ensure that guide wire 218 is not bent or kinked during the tapping process. The position of tap 230 relative to the end of guide wire 218 may be monitored to ensure that guide wire 218 is not dislodged or removed from the vertebra. In some embodiments, a position of tap 230 may be monitored using fluoroscopic imaging.

Figure 66F:
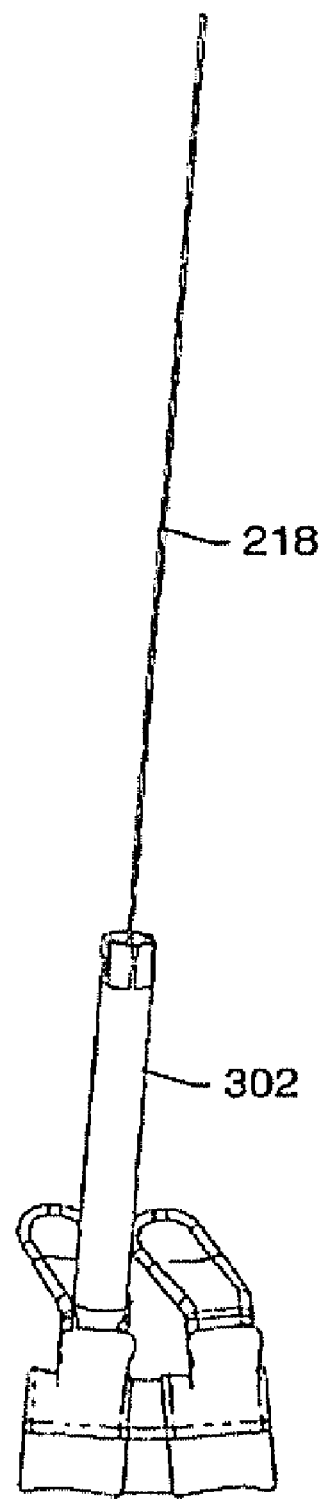

After a threaded passage of a desired length has been formed in pedicle 164 and vertebral body 166, a second measurement of the position of tap 230 relative to a top of dilator 302 using indicia 240 may be noted. A length of a threaded member may be determined by taking a difference between the first and second measurements. In some embodiments, an estimate of length may be derived based upon fluoroscopic images and a known length of the tap that is visibly recognizable in the fluoroscopic images. Tap 230 may be removed from vertebral body 166 and pedicle 164 by rotating the tap out of the vertebral body and the pedicle. Handle 236 may be removed from a blade portion of tap 230. The blade portion of tap 230 may be removed from guide wire 218 with control of the guide wire initially maintained from above the tap and then from below the tap. Care may be taken when tap 230 is removed to maintain guide wire 218 in position and to avoid damage of the guide wire. FIG. 66F depicts dilator 302 and guide wire 218 after removal of the tap.

A bone fastener assembly with a bone fastener of an appropriate length may be selected for insertion in a patient. The size of the bone fastener may be verified with measurement indicia in an instrumentation set. In some embodiments, measurement indicia may be etched or printed on a portion of an instrumentation set. For example, the chosen bone fastener embodiment may be placed over the outline of a bone fastener embodiment printed on a tray of the instrumentation set.

The chosen bone fastener assembly may be attached to a detachable member. In an embodiment, a bone fastener assembly may be rotated on a flange of a detachable member. Movable members of the detachable member may be extended into indentations in a collar of the bone fastener assembly. A driver may be used to extend the movable members to couple with the collar. When the bone fastener assembly is coupled to the detachable member, a drive portion of a fastener driver may be coupled to a tool portion of the bone fastener. A shaft of the fastener driver may be positioned in the passage of the detachable member. A removable handle may be attached to the shaft of the fastener driver. The detachable member, collar, and bone fastener may be substantially coaxial when the fastener driver is positioned in the detachable member. In some embodiments, the removable handle may be attached to the shaft of the fastener driver after the bone fastener, collar, detachable member, and fastener driver combination is positioned down a guide wire through a dilator and against a pedicle.

FIGS. 67A-67D depict portions of a procedure for inserting a bone fastener assembly into a patient. Driver 292 (coupled to the bone fastener), and sleeve 244 (coupled to the collar of the bone fastener assembly) may be inserted along guide wire 218 into dilator 302. For spinal stabilization procedures using four successively sized dilators, dilator 302 may be fourth dilator 302D. Guide wire 218 represents the trajectory that a bone fastener or bone fastener assembly may follow toward pedicle 164 during insertion of a spinal stabilization system. In some embodiments, tissue surrounding the incision may be pulled and/or stretched to allow a desired angular orientation of the bone fastener assembly relative to pedicle 164. FIG. 67A depicts driver 292 and sleeve 244 positioned in dilator 302. After insertion of the bone fastener assembly, sleeve 244, and driver 292 in dilator 302, the driver may be rotated to thread the bone fastener into pedicle 164 and vertebral body 166. The bone fastener may be advanced into the pedicle under fluoroscopic guidance to inhibit breaching of the pedicle walls. When the tip of the bone fastener advances beyond the posterior margin of vertebral body 166, guide wire 218 may be removed to inhibit inadvertent bending of the guide wire or unwanted advancement of the guide wire.

The bone fastener may be advanced to bring the collar down snug to the facet joint. The bone fastener may then be backed off about a quarter of a turn. Backing the fastener off about a quarter of a turn may allow for full motion of the collar relative to the bone fastener. FIG. 67B depicts driver 292 after the bone fastener has been advanced to the desired depth. After the bone fastener has been advanced to the desired depth, driver 292 may be removed from the head of the bone fastener and from dilator 302. FIG. 67C depicts dilator 302 and sleeve 244 after removal of the driver. After removal of the driver, dilator 302 may be removed from the patient. FIG. 67D depicts collar 112 of bone fastener assembly and sleeve 244 after removal of the dilator.

After the bone fastener has been secured to the vertebra and the driver has been removed from the sleeve, the polyaxial nature of the collar may allow angulation of the sleeve relative to the bone fastener. Tissue surrounding the incision may be released such that the sleeve is angled toward a central location between vertebrae to be stabilized. The sleeve may be moved to facilitate positioning of instruments and/or to facilitate access to the adjacent vertebra that is to be stabilized. For example, the sleeve may be tilted towards the adjacent pedicle so that additional length of an opening in the patient is not needed. The channel in the sleeve may be turned toward the adjacent pedicle that is to be stabilized with the spinal stabilization system being formed.

A plane of dilated tissue may be created between a first pedicle and a second pedicle to be stabilized with a spinal stabilization system. A bone fastener assembly and a sleeve may be coupled to the first pedicle. The second pedicle may be adjacent to the first pedicle. In an embodiment, a tissue wedge may be placed in the sleeve coupled to the first pedicle such that the distal end of the tissue wedge contacts the head of the bone fastener. The proximal end of the sleeve coupled to the first pedicle may be held such that tissue around the incision is not pulled or stretched. The tissue wedge may be wanded through the channel in the sleeve and the slot in the collar toward the target location at the second pedicle, thereby creating a plane in muscle and other tissue between the head of the installed bone fastener and the target location of a second bone fastener in some embodiments, a tissue wedge may be pivoted about an inside proximal edge of the sleeve such that the distal end of the tissue wedge bluntly splits the muscle and fascia along fibers and create a tissue plane between the two pedicles. The wanding action may be repeated more than once (e.g., two or three times) to create a good working plane and displace unwanted tissue from the plane. The wanding may create a tissue plane. In some embodiments, the tissue plane may be substantially trapezoidal. In certain embodiments, a tissue plane may be created before a bone fastener assembly is inserted into a vertebra.

Figure 68D:
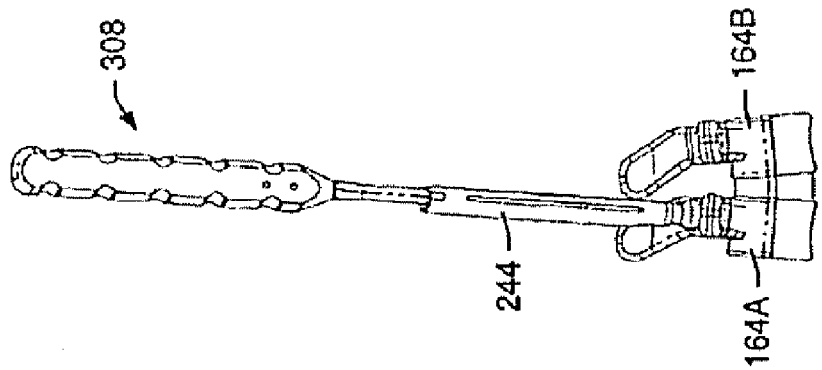
FIGS. 68A-68D depict schematic views of tissue plane creation during a minimally invasive spinal stabilization procedure.
Figure 68C:
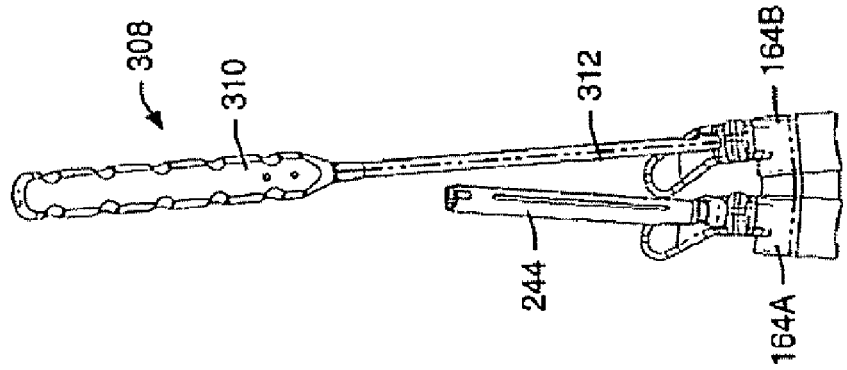
Figure 68B:
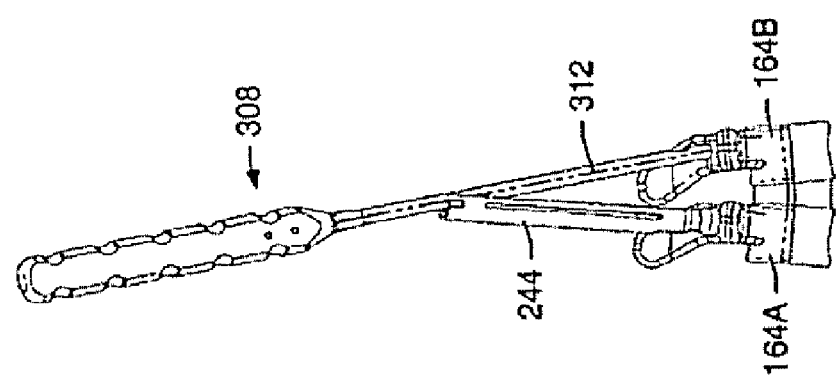
Figure 68A:
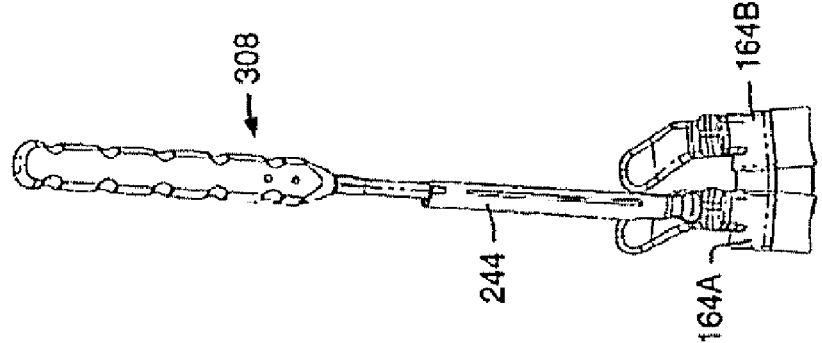

FIGS. 68A-D depict some stages during use of a tissue wedge to form a tissue plane between a sleeve in a first pedicle and a target location at a second pedicle. FIG. 68A depicts tissue wedge 308 aligned above pedicle 164A in sleeve 244. With a portion of tissue wedge 308 held proximate to the proximal end of sleeve 244 or resting on the proximal end of the sleeve, blade 312 of tissue wedge 308 may be moved through soft tissue from pedicle 164A toward pedicle 164B. FIG. 68B depicts distal end of tissue wedge 308 positioned at pedicle 164B. After tissue wedge 308 contacts pedicle 164B, handle 310 may be moved toward pedicle 164B (i.e., away from sleeve 244) to further separate soft tissue in a plane between the pedicles. FIG. 68C depicts tissue wedge 308 after handle 310 has been angled away from sleeve 244. An initial plane may be created by wanding tissue wedge from pedicle 164A to pedicle 164B. Tissue wedge 308 may be similarly wanded back to pedicle 164A to further establish the plane. FIG. 68D depicts tissue wedge 308 realigned in sleeve 244 after the plane has been established with a back-and-forth motion. In some embodiments, handle 310 may be maintained proximate sleeve 244 to minimize the area of the tissue plane.

A tissue plane may be made in a variety of shapes including, but not limited to, substantially trapezoidal, substantially rhomboidal, and substantially triangular. A tissue plane with a substantially geometric shape may have the basic geometric shape with, for example, slightly curved edges and/or slightly rounded corners or apices. In some embodiments, a sleeve length may be chosen to reduce a size of a tissue plane that needs to be formed between pedicles. In certain embodiments, creating a trapezoidal tissue plane may reduce the invasiveness of a procedure. Limiting the area of the plane may promote a faster recovery time and/or may reduce an amount of post-operative pain experienced by the patient.

Figure 69:
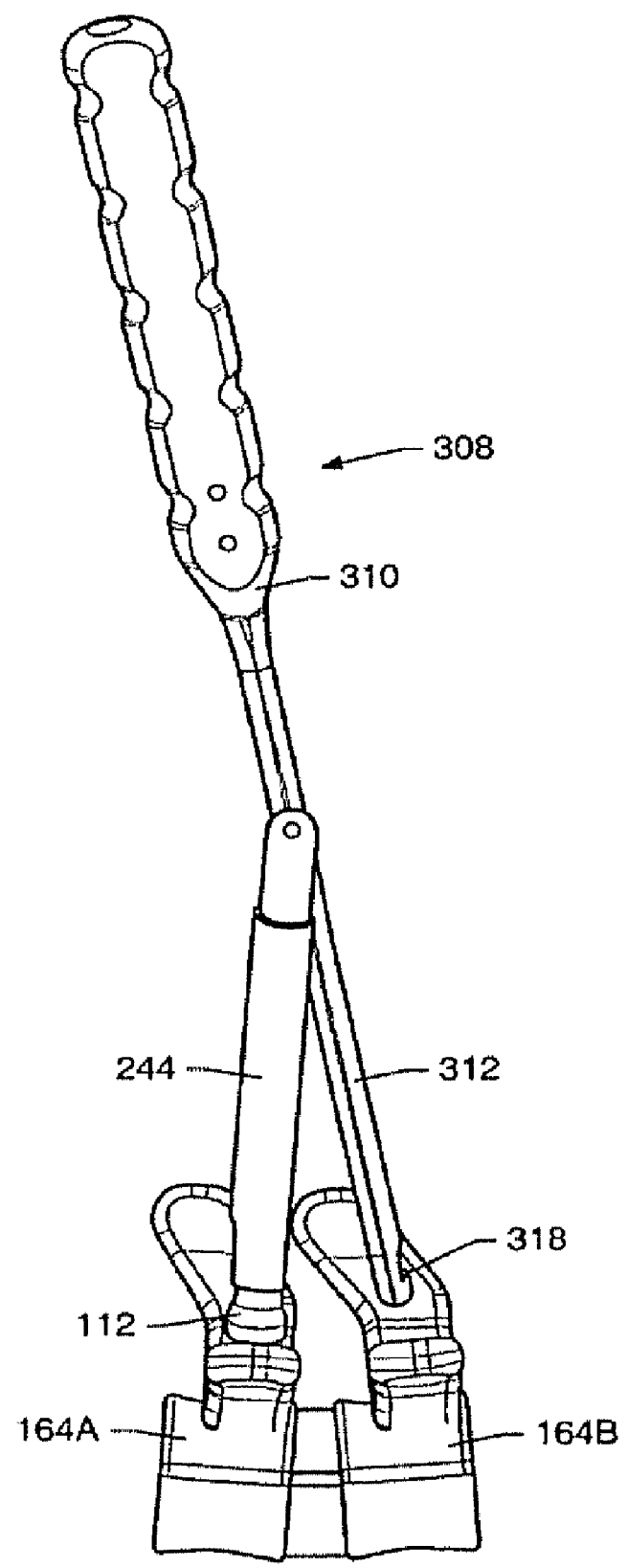
FIG. 69 depicts an embodiment of a tissue wedge.

In an embodiment, a tissue wedge may be coupled to a portion of a sleeve to facilitate creation of a tissue plane. FIG. 69 depicts tissue wedge 308 with blade 312 pivotally coupled to a proximal extension of sleeve 244. Tissue wedge 308 may be initially positioned in sleeve 244 with a distal end of blade 312 proximate pedicle 164A. Handle 310 may be pivoted toward pedicle 164A to allow wanding of blade 312 towards adjacent pedicle 164B. If needed, cutting edge 318 may be used to sever fascia that inhibits passage of blade 312. Sleeve 244 may be pivoted in conjunction with rotation of collar 112. In another embodiment, sleeve 244 may be extendable (e.g., telescopic) such that a pivot point may be advanced in the direction of pedicle 164B during wanding. The extendable portion of the sleeve may be selectively lockable using a variety of locking mechanisms including, but not limited to, a setscrew, a clip, a detent, or a pin.

In an embodiment, two pedicles may be targeted and bone fastener assemblies anchored in both pedicles before creation of a tissue plane. A tissue wedge may be inserted at either of the pedicles. In some embodiments, the sleeves may be coupled to each other at proximal ends of the sleeves. The tissue wedge may be coupled to a sleeve and the sleeve may be used as an anchor during wanding. Insertion of an elongated member into collars of bone fastener assemblies, however, may require cutting of some tissue between the two sleeves.

Other procedures may be used to create a tissue plane. For example, before targeting pedicle locations (i.e., before bone fastener insertion), a tissue wedge may be worked downward from an incision to create a tissue plane. Alternatively, a scalpel may be used to cut from the surface of the body to vertebral bone. Extensive use of a scalpel, however, may remove benefits of a minimally invasive procedure.

Figure 70:
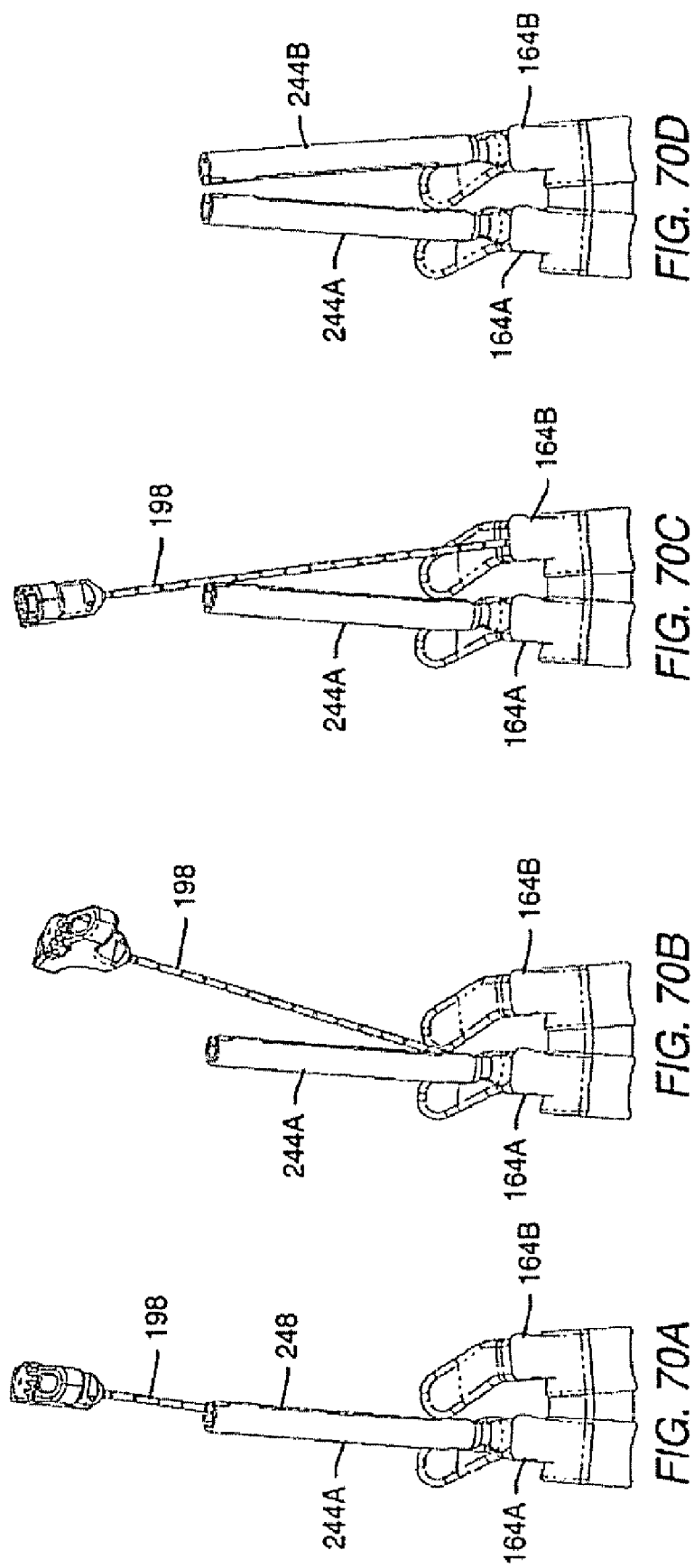
FIGS. 70A-70D depict schematic views of placement of a sleeve and a bone fastener assembly in second vertebra during a minimally invasive spinal stabilization procedure.

In an embodiment, a targeting needle may be passed through the tissue to create a tissue plane for insertion of an elongated member. As depicted in FIG. 70A, targeting needle 198 may be placed in sleeve 244A coupled to pedicle 164A. Sleeve 244A may be rotated such that channel 248 is directed toward pedicle 164B. In some embodiments, a handle portion of targeting needle 198 may be positioned over pedicle 164B, as depicted in FIG. 70B. The shaft of targeting needle 198 may be wanded from sleeve 244A (e.g., from a center of sleeve 244A) in pedicle 164A to a target location in pedicle 164B to separate the soft tissue in a plane between the pedicles. FIG. 70C depicts a distal end of targeting needle 198 positioned proximate pedicle 164B. Targeting needle 198 may be moved back and forth to establish the plane. After targeting needle 198 contacts pedicle 164B and the plane is established, a bone fastener assembly may be inserted in pedicle 164B using a procedure similar to the procedure used to place a bone fastener assembly in an adjacent pedicle. FIG. 70D depicts sleeves 244A and 2448 located proximate pedicles 164A and 164B, respectively.

Figure 71:
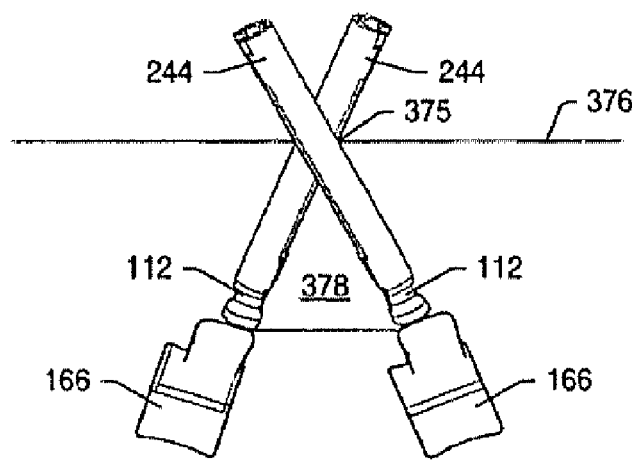
FIG. 71 depicts a tissue plane between adjacent vertebrae with anchored sleeves crossing at the surface of the skin.

Once a well-defined tissue plane has been formed, a targeting needle may be passed down a first sleeve coupled to a first vertebra and then wanded along the formed plane over to a target location at a second pedicle. The target location at the second pedicle may be fluoroscopically confirmed. A bone fastener assembly coupled to a sleeve may be secured in the second pedicle using a procedure similar to the procedure used to insert a bone fastener assembly in a first pedicle. FIG. 71 depicts substantially trapezoidal tissue plane 378 between sleeves 244 coupled to adjacent vertebral bodies 166. Sleeves 244 touch at incision 375 and cross above body surface 376, such that a length of the incision and/or an area of tissue plane 378 may be advantageously small. Substantially trapezoidal tissue plane 378 may have a dimension at body surface 376 equal to a length of the incision. Sides of substantially trapezoidal tissue plane 378 may define by surfaces of sleeves 244. Opposite the body surface 376, substantially trapezoidal tissue plane 378 may extend between collars 112. In some embodiments, the edge of substantially trapezoidal tissue plane 378 closest vertebral bodies 166 may be substantially straight. In some embodiments, the edge of substantially trapezoidal tissue plane 378 closest vertebral bodies 166 may be curved to match a contour of bone between the vertebral bodies.

With bone fastener assemblies secured in the vertebral bodies, sleeves coupled to the bone fastener assemblies may be oriented to facilitate insertion of an elongated member in the sleeves. In some embodiments, sleeves may serve as tissue retractors during a spinal stabilization procedure. Angular motion of a collar may be limited by a range of motion allowed between the collar and the bone fastener that the collar is anchored to. Angular motion of a collar may be limited by patient anatomy. Angular motion or orientation of one collar (i.e., sleeve), however, may not depend upon a position of another collar (i.e., sleeve). In some embodiments, channel openings in the sleeves may face each other. In other embodiments, channel openings in the sleeves may be angled relative to each other in various arrangements. A distance between the sleeves may be estimated using an estimating tool. The distance between the sleeves may be used to select a length of an elongated member needed to couple the collars.

In an embodiment, flexible arms of estimating tool 320 depicted in FIG. 54 may be positioned in sleeves. With the activator disengaged, the estimating tool may be advanced toward the pedicles until the arms or members rest on the collars or bone fasteners of the bone fastener assemblies. The activator may be engaged. When the arms are withdrawn from the sleeves, a biasing element may allow the arms to extend to the length indicative of the distance between bone fastener assemblies. An elongated member length may be selected by measuring a distance between the members of the estimating tool. The measured distance may be increased by an amount to allow the elongated member to extend beyond the collars after curvature and/or insertion. In an embodiment, about 5 mm to about 30 mm (e.g., about 15 mm) may be added to the measured distance. In some embodiments, a desired length of an elongated member may be a length that allows the elongated member to extend from each collar by about 2 mm or about 3 mm. In certain embodiments, ends of an elongated member may be flush with the outer surface of one or more collars.

In an embodiment, an elongated member of desired length may be chosen by estimating a distance between the sleeves without the use of an estimating tool. The sleeves may be positioned as desired (e.g., substantially parallel to each other). A distance between the most distant outer edges of the sleeves may be estimated. The estimated distance may be increased by an amount to allow the elongated member to extend beyond the collars after insertion. In some embodiments, from about 1 mm to about 20 mm may be added to the estimated distance. In some embodiments, a desired length of elongated member may be a length that allows the elongated member to extend from each collar by about 2 mm.

An elongated member may be cut to length and contoured as desired. For example, a medical practitioner may use experience and judgment to determine curvature of an elongated member for a patient. A desired curvature for the elongated member may be determined using fluoroscopic imaging. In some embodiments, a curvature of the elongated member may be chosen such that, when the elongated member is secured to the collars of the bone fastener assemblies, sleeves coupled to the bone fastener assemblies cross at a surface of the skin. Crossing of the sleeves at a surface of the skin allows the medical practitioner to minimize trauma to a patient by minimizing incision length and tissue plane area. The elongated member may be bent or shaped with a tool (e.g., a rod bender) to allow insertion of the elongated member through channels of sleeves with various spatial locations and/or various angular orientations.

Figure 72:
FIG. 72 depicts an embodiment of an elongated member.
Figure 73:
FIG. 73 depicts an embodiment of an elongated member.
Figure 74:
FIG. 74 depicts an embodiment of an elongated member.
Figure 75:
FIG. 75 depicts an embodiment of an elongated member.

Elongated members may have shapes including, but not limited to, straight, bent, curved, s-shaped, and z-shaped. FIG. 72 depicts an embodiment of S-shaped elongated member 104. FIG. 73 depicts an embodiment of angled elongated member 104. FIG. 74 depicts an embodiment of bent elongated member 104. FIG. 75 depicts an embodiment of straight elongated member 104. In some embodiments, elongated members 104 may have a substantially circular longitudinal cross section. In certain embodiments, elongated members 104 may have other cross-sectional shapes including, but not limited to, regular shapes (oval, rectangular, rhomboidal, square) and irregular shapes. An instrumentation kit for a spinal stabilization system may include straight rods and/or pre-shaped rods. Straight rods and/or pre-shaped rods may be contoured to accommodate patient anatomy if needed during the surgical procedure.

Channels of the sleeves and slots of the collars may be oriented by rotating the sleeves to accommodate insertion and seating of the elongated member. In certain embodiments, a channel opening in a sleeve may be non-linear (e.g., bent, curved, or angled) to allow portions of the spine to be selectively stabilized. Sleeve orientation and/or design may be chosen to allow compression, distraction, and/or reduction of vertebrae. In some embodiments, there may be no constraints governing relative location and/or orientation of the sleeves. Sleeves may be forced apart or angled toward each other or away from each other to accommodate insertion of the elongated member.

Prior to insertion of the elongated member, the tissue wedge or targeting needle may be used to wand between the bone fasteners to ensure a clean plane between the bone fasteners. An end of the elongated member may be inserted at an angle or substantially longitudinally in a passage and/or channel of a sleeve coupled to a bone fastener assembly. Inserting the elongated member at an angle or substantially longitudinally allows the length of the incision and/or the area of the tissue plane to remain advantageously small. In some embodiments, sleeves coupled to anchored bone fastener assemblies may remain essentially unconstrained relative to each other during insertion of the elongated member. In certain embodiments, angular orientation of the collars may determine a trajectory of the elongated member down the sleeves and into collars of the bone fastener assemblies. Inserting the elongated member down two or more sleeves and through an open path (i.e., the tissue plane) may allow a medical practitioner to avoid surgical difficulties associated with anatomical abnormalities and/or misalignment of system components (e.g., in multi-level stabilization procedures).

Insertion of the elongated member may not be visualized subcutaneously. Therefore, a positioning tool may be used to guide the elongated member down the sleeves into slots in the collars. A distal portion of the positioning tool may be contoured. The contour may allow for some rotation of the elongated member. With slight pressure, the elongated member may be rotated subcutaneously into a substantially horizontal position and seated in the collars. The positioning tool may be held firmly while still allowing a rocking movement between the elongated member and the distal end of the positioning tool. Movement of the elongated member may allow the elongated member to be maneuvered down the sleeves and into the collars.

Figure 76A:
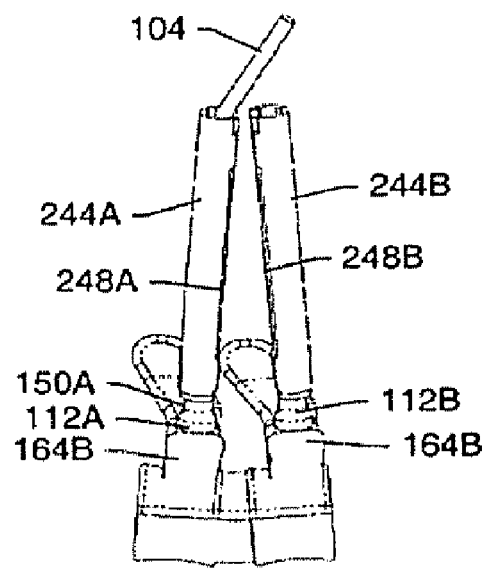
FIGS. 76A-76D depict schematic views of elongated member placement during a minimally invasive spinal stabilization.
Figure 76C:
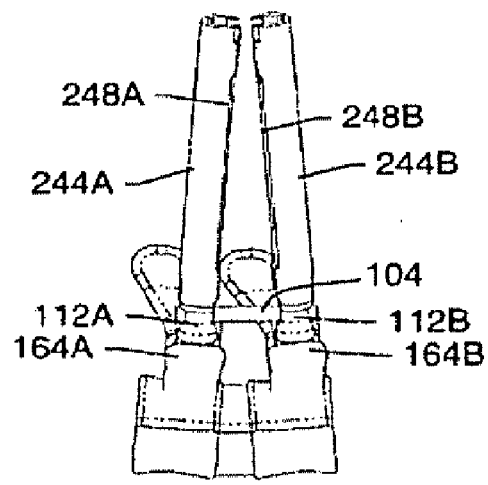
Figure 76B:
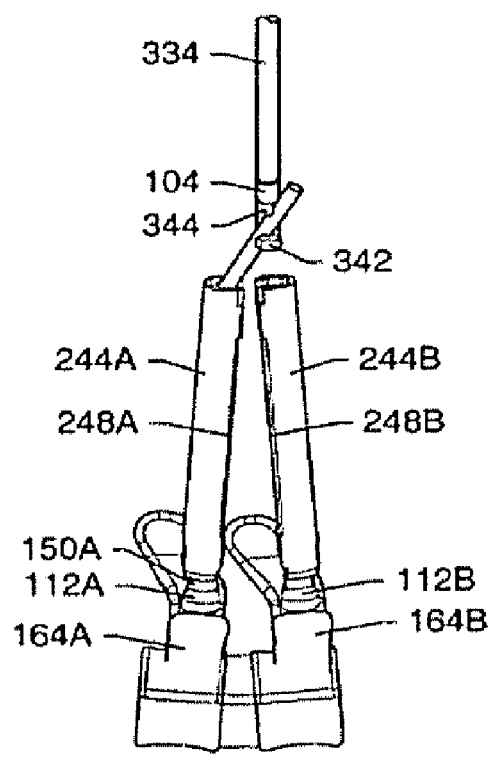

FIG. 76A depicts insertion of a first end of elongated member 104 in an opening of channel 248A of sleeve 244A. In an embodiment, elongated member 104 may be positioned between grasping member 342 and distal end 344 of the inner shaft of positioning tool 334, as shown in FIG. 76B. The elongated member may be held between grasping member 342 and distal end 344 of the inner shaft of positioning tool 334 with pressure applied to a proximal end of the inner shaft. As the first end of elongated member 104 is moved along the length of sleeve 244A toward collar 112A, a second end of the elongated member may be inserted in channel 248B of sleeve 244B. Channels in sleeves 244A and 244B may include grooves opposite channel openings to engage ends of elongated member 104 and/or to guide the elongated member along the lengths of the sleeves. Positioning tool 334 may be used to guide the elongated member along the length of the sleeves through the plane in the soft tissue.

Slots in collars 112A, 12B may be aligned with channels 248A, 248B of sleeves 244A, 244B, respectively, to allow elongated member 104 to be positioned in the collars. Positioning tool 334 may be used to angle the elongated member through slot 150A such that an end of the elongated member protrudes through collar 112A away from collar 112B. With one end of elongated member 104 extending through slot 150A in collar 112A, positioning tool 334 may be used to guide the other end of the elongated member the remaining distance down second sleeve 244B. Positioning tool 334 may then be used to seat the second end of elongated member 104 in collar 112B and translate the elongated member to a desired location relative to the collars. The distal end of the positioning tool inner shaft may be contoured (e.g., curved and/or grooved) to allow some motion (e.g., rocking) of elongated member 104 while the elongated member is coaxed into position and/or rotated subcutaneously with the positioning tool. Pressure may be applied to inner shaft 340 to seat elongated member 104 in the slots of the collars. FIG. 76C depicts elongated member 104 seated in collars 112A, 112B.

Figure 76D:
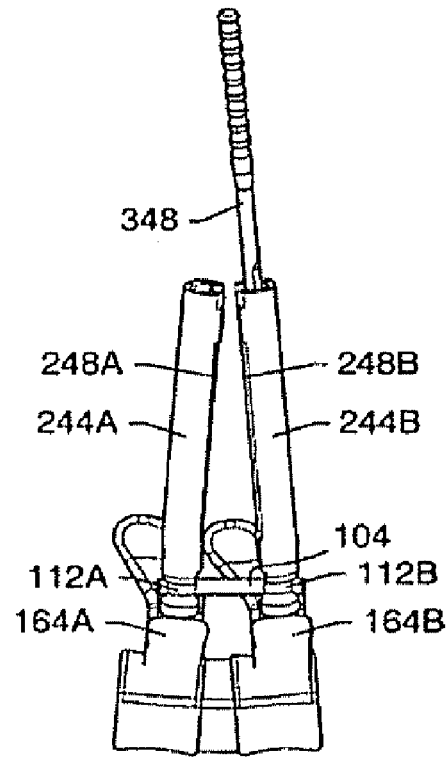

In some embodiments, a seater may be used to seat the elongated member in the collars. FIG. 76D depicts seater 348 positioned in sleeve 244B. In certain embodiments, seater 348 may be used to push elongated member 104 into slots in collar 112A and/or 112B while the positioning toot is used to maneuver the elongated member into place. Once the elongated member is positioned in the collars, fluoroscopic confirmation may ensure that the elongated member is inserted fully into each collar. Prior to securing the elongated member to bone fastener assemblies with closure members, the elongated member may be gripped firmly with the positioning tool and persuaded cephalad or caudad as needed. With the elongated member seated in the collars, orientation of the sleeves may be constrained relative to each other.

After the elongated member is seated in the collars, additional fluoroscopic confirmation of elongated member positioning may be obtained. With the elongated member satisfactorily positioned, the elongated member may be secured in place with closure members. FIG. 60A depicts closure member 106 coupled to driver 354. Driver 354 is positioned for insertion into sleeve 244. A counter torque wrench may be coupled to the sleeve or to the elongated member. After insertion of driver 354 in sleeve 244, closure member 106 may be positioned proximate collar 112. With driver 354 positioned in sleeve 244, as shown in FIG. 60B, the driver may be rotated to advance the closure member in collar 112. To ensure alignment of thread of closure member with thread of collar, the driver may initially be rotated in a direction that would result in removal of the closure member from the collar. When the user of the driver feels engagement of threading of the closure member with threading of the collar, the user may reverse the direction of rotation of the driver to secure the closure member to the driver. The closure member may secure the elongated member to the collar. Sleeve 244A may serve as a coaxial guide to inhibit cross-threading during insertion of closure members 106. When the closure members are snug and elongated member 104 is secured, collars 112 are angled such that slots in the collars are substantially perpendicular to the elongated member. Driver 354 may be disengaged from the closure member and removed from sleeve 244. In some embodiments, driver 354 may be used to shear off a tool portion of a secured closure member. In certain embodiments, a coupling portion of driver 354 may capture a sheared tool portion from a closure member.

Torque required to shear off the tool portion of a closure member may be a source of pain and/or injury to a patient. In some embodiments, sleeve 244 may be held with a counter torque wrench as the tool portion of a secured closure member is sheared off. In an embodiment, about 90 in-lbs of torque may be required to shear off the tool portion of a closure member. A counter torque wrench may inhibit or reduce transfer of torque to the patient's spine. FIG. 61 depicts an embodiment of counter torque wrench 364 used above the skin to inhibit application of torque to a patient's spine during shearing of a tool portion of a secured closure member. Sleeve 244 may fit in opening 366 of counter torque wrench 364. Counter torque wrench 364 may be positioned near a proximal end of sleeve 244 during use.

Force may be applied to counter torque wrench 364 in a direction opposite to rotational force applied to driver 354 to shear off a tool portion of closure member 106. Thus, the tool portion of closure member 106 may be sheared off with force exerted above the incision of a patient. In some embodiments, a collar of a bone fastener assembly may be designed such that a proximal portion of the collar may be sheared off with force exerted above the incision of a patient. In some embodiments, closure member 106 may be designed (e.g., with a solid central core) such that the torque required to shear off the tool portion does not adversely affect the body of the closure member or the coupling between the closure member and the collar. Opening 366 in torque wrench 364 may be of any shape to accommodate a cross-sectional shape of sleeve 244.

In some embodiments, counter torque wrench 368 shown in FIG. 63 may be used to inhibit application of torque to a patient's spine. Counter torque wrench sleeve 370 may be inserted through the opening in the body over sleeve 244. Counter torque wrench sleeve 370 may be advanced toward the spine until elongated member 104 is seated in groove 374 of the counter torque wrench sleeve. Force may be applied to counter torque wrench 368 in a direction opposite to rotational force applied to a driver used to shear off a tool portion of a secured closure member.

Coupling failure between a collar and a closure member of a bone fastener assembly may be a concern during surgery. If failure occurs while locking down an elongated member to a bone fastener assembly in a single- or multi-level system, the failure may require removal of one or more locked closure members and the elongated member to extract a failed bone fastener assembly. Coupling failure may occur during application of other loads, such as loads used to achieve reduction with a spinal stabilization system.

Figure 77:
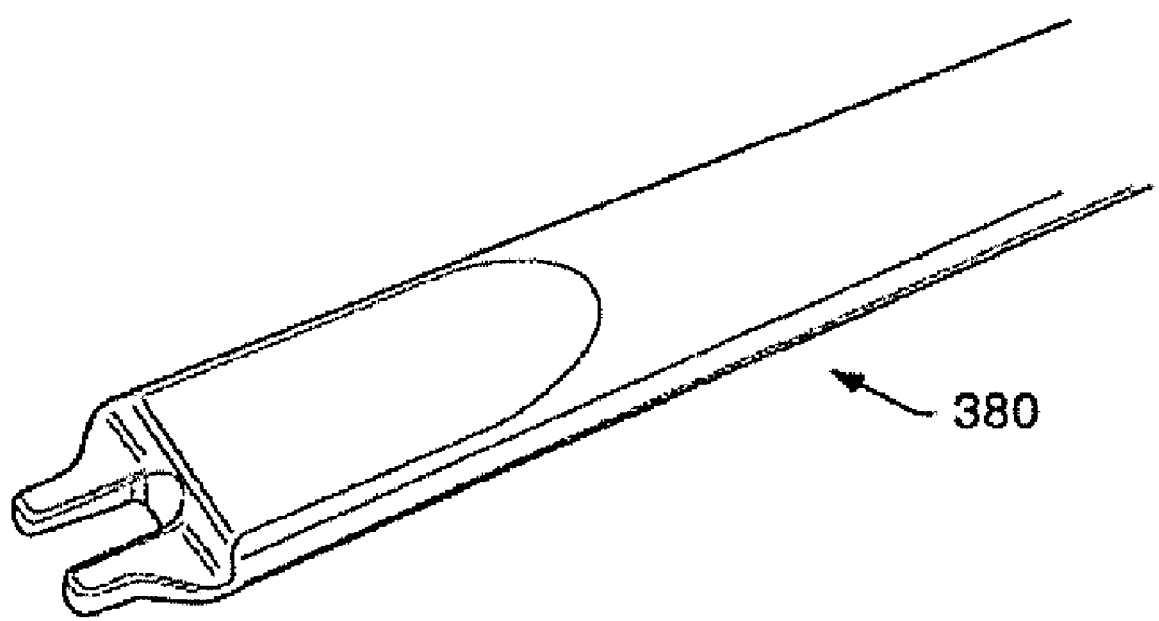
FIG. 77 depicts a perspective view of a distal portion of a two-pronged driver.

FIG. 77 depicts a distal portion of driver 380 that may be used to remove closure member 106 depicted in FIGS. 14 and 15. A distal end of driver 380 may include two prongs designed to fit in removal openings 174 of closure member 106. Driver 380 may be inserted in a sleeve to engage a closure member. A handle of driver 380 may allow a medical practitioner to apply force in a rotational direction necessary to remove the closure member. In some embodiments, a counter torque wrench may be used to inhibit application of torque to the patient's spine during removal of a closure member. The closure member may be removed and replaced as necessary.

After a closure member is successfully secured to a collar and a tool portion of the closure member has been sheared off, the driver may be removed from the sleeve coupled to the anchored bone fastener assembly. FIG. 78A depicts an assembled spinal stabilization system following removal of driver 354. Key 262, shown in FIG. 78B, may be used to rotate movable members in sleeves 244A, 244B. Rotation of movable members in sleeves 244A, 244B may release the movable members from the collars. Thus, sleeves 244A, 244B may be uncoupled from the collars above the incision. FIG. 78C depicts assembled spinal stabilization system 100 following removal of sleeve 244A. FIG. 78D depicts assembled spinal stabilization system 100 coupled to adjacent pedicles following removal of sleeve 244B.

A spinal stabilization system may be used to stabilize two or more vertebral levels (i.e., at least three adjacent vertebrae). In an embodiment, an incision may be made in the skin between the outermost vertebrae to be stabilized. A first bone fastener assembly may be coupled to a first sleeve. The first bone fastener may be threaded into a first pedicle at a target location such that the first sleeve extends above the body surface. The first sleeve may rotate about the head of the first bone fastener. A tissue plane may be created between a channel opening in the first sleeve and a target location at a second pedicle. In an embodiment, the second pedicle may be adjacent to the first pedicle. A second bone fastener assembly may be coupled to a second sleeve and threaded into the second pedicle through the incision. Another tissue plane may be created between the first sleeve or the second sleeve and a target location in a third pedicle. The third pedicle may be adjacent to the first pedicle and/or the second pedicle. A third bone fastener assembly may be coupled to a third sleeve and threaded into the third pedicle through the incision.

In an embodiment of a method for a two-level spinal stabilization procedure, an incision may be made above a target location in a middle pedicle. A first bone fastener may be anchored to the middle pedicle. After the first bone fastener is secured, second and third bone fasteners may be coupled to outer pedicles as desired by pulling and/or stretching tissue surrounding the incision to allow access to the outer pedicles.

Figure 79D:
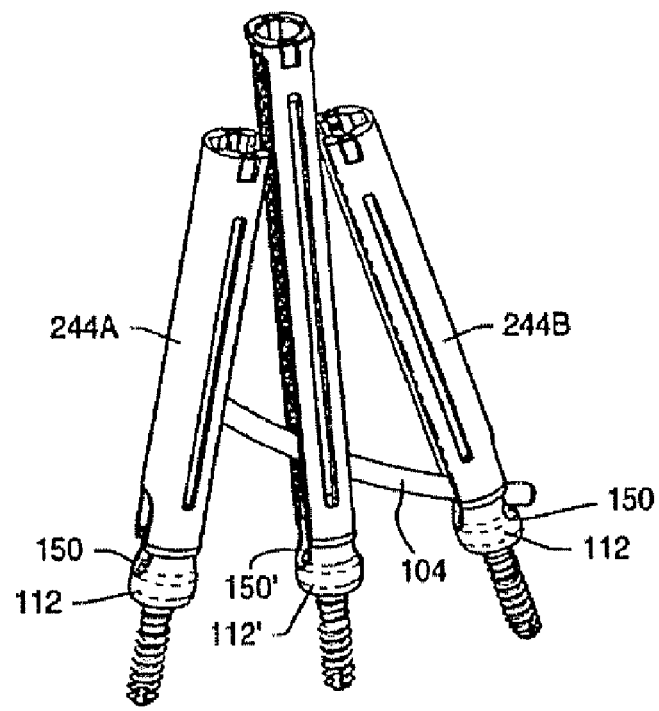

Channel openings in sleeves coupled to three bone fastener assemblies may be oriented to allow insertion of an elongated member to achieve two-level spinal stabilization. FIGS. 79A-79E depict insertion and seating of an elongated member in a two-level spinal stabilization system. Use of a rod positioner and/or seater is implied but not shown in FIGS. 79A-79E. FIG. 79A depicts insertion of a first portion of elongated member 104 through channel 248' of multi-channel sleeve 244 and into channel 248 of sleeve 244B. As the first portion of elongated member 104 is moved down the length of channels 248, 248' toward collars 112, 112', a second portion of the elongated member may be inserted in channel 248 of sleeve 244A. In some embodiments, elongated member 104 may be moved down channels 248, 248' using a positioning tool. As elongated member 104 is advanced toward collars 112, 112', the elongated member may pass through an opening in the skin and into the tissue plane. FIG. 79B depicts elongated member 104 in channels 248, 248' Channels 248 in sleeves 244A, 244B may include grooves to engage ends of elongated member 104 and/or to guide the elongated member down the lengths of the sleeves. In certain embodiments, channel openings may be curved or angled to accommodate various elongated member configurations.

Figure 79E:
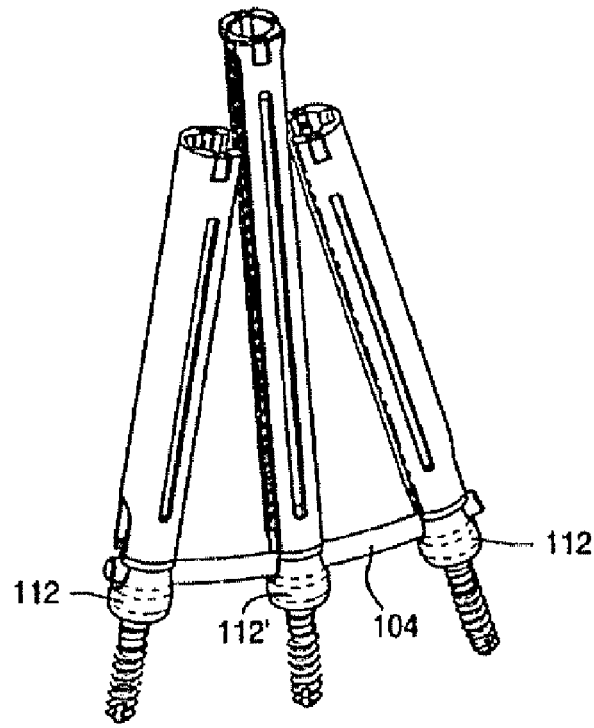

FIG. 79C depicts elongated member 104 engaged in channels 248, 248'. As elongated member 104 is advanced toward collars 112, 112', a first end of the elongated member may emerge through slot 150 in collar 112 coupled to sleeve 244B. FIG. 79D depicts elongated member 104 after the elongated member has emerged through slot 150 in collar 112 coupled to sleeve 244B. In some embodiments, a seater may be used to position elongated member 104 in collars 112, 112'. FIG. 79E depicts elongated member 104 seated in collars 112, 112'.

Figure 80B:
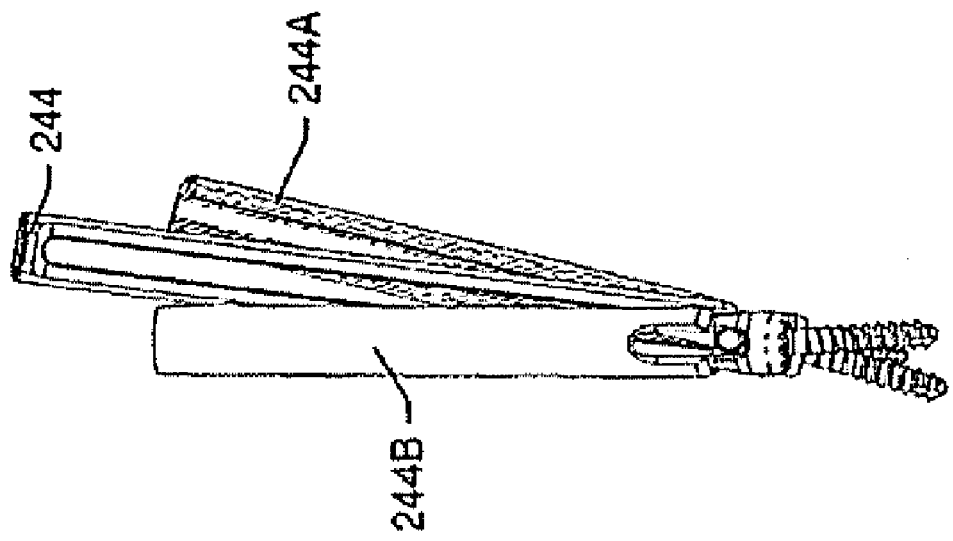
FIGS. 80A-80C depict schematic views of bone fastener assemblies coupled to sleeves.
Figure 80A:
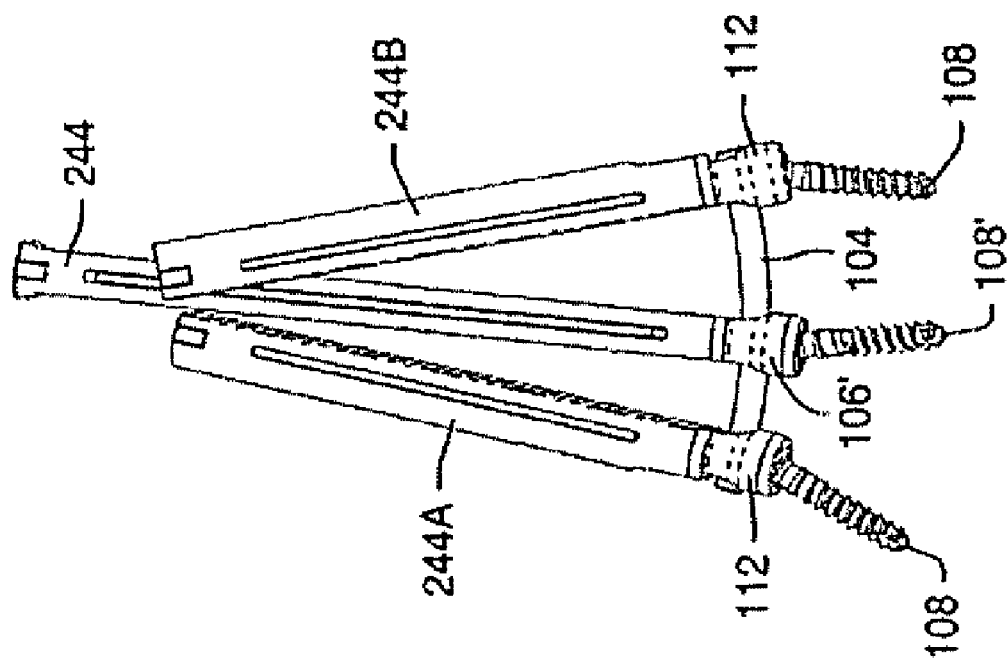
Figure 80C:
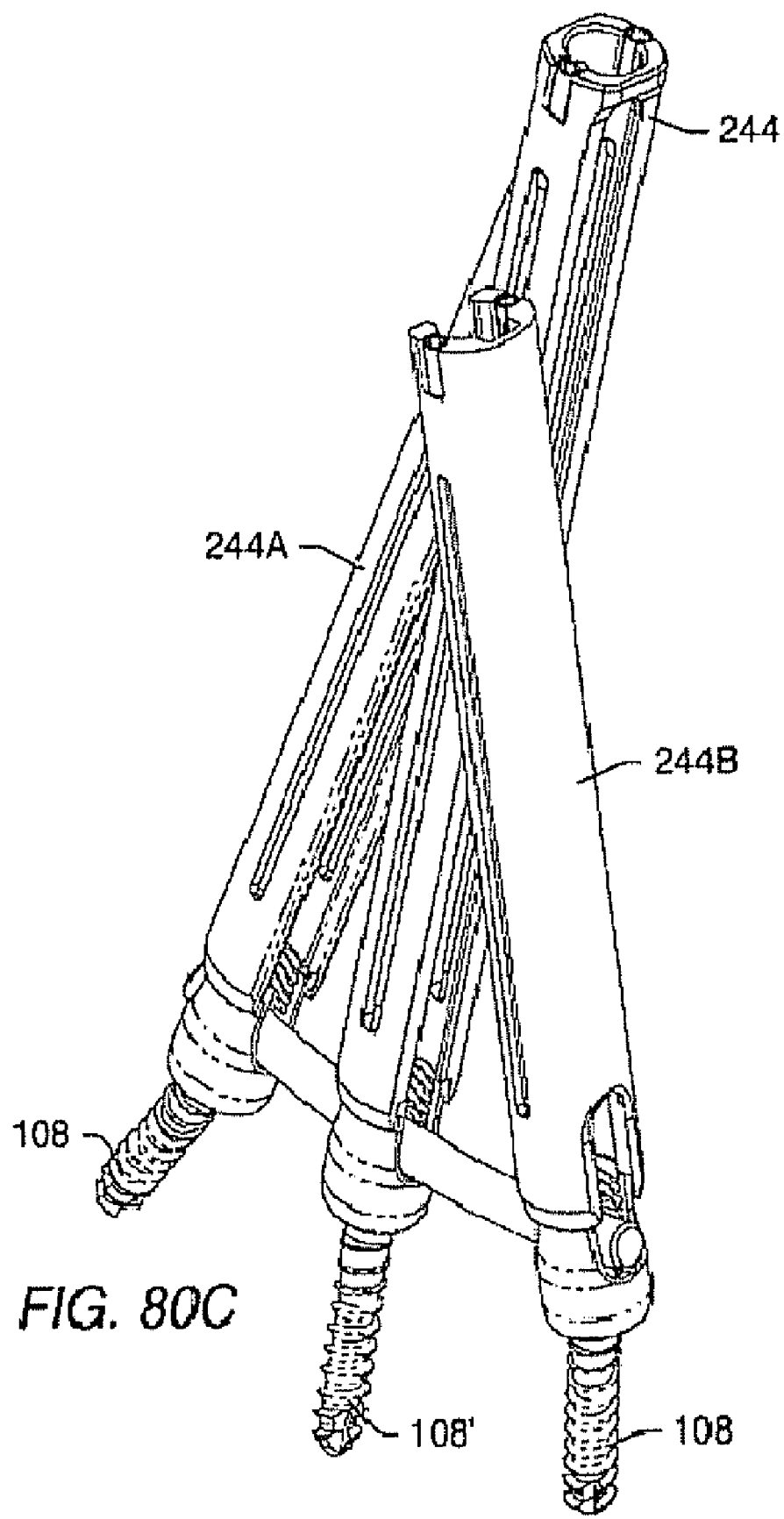

FIGS. 80A-80C depict perspective views of various orientations sleeves 244 may assume relative to bone fasteners 108, 108'. In two-level and multi-level spinal stabilization systems, an orientation of a sleeve coupled to an anchored bone fastener assembly is not constrained by an orientation of one or more other collars coupled to adjacent bone fastener assemblies. FIGS. 80A-80C also depict various orientations that bone fasteners 108, 108' may assume relative to each other. Bone fasteners 108, 108' may be offset from each other (i.e., non-planar) and/or be inserted in pedicles at opposing angles. The range of possible orientations of bone fasteners in pedicles may allow a spinal stabilization system to securely conform to a patient's spine.

After an elongated member has been positioned and seated in collars as desired, closure members may be used to secure the elongated member to the collars. One or more counter torque wrenches may be used during shearing of the tool portions of the closure members. In an embodiment, counter torque wrench 364, depicted in FIG. 61, may be used with sleeves 244A, 244B. Counter torque wrench 368, depicted in FIG. 62, may be used with multi-channel sleeves and/or single-channel sleeves.

In certain embodiments, an external frame may be used to impose a desired constraint on one or more sleeves. For example, an external frame may hold one or more sleeves in a particular location and/or orientation such that a desired relative positioning of vertebrae may be achieved. An external frame may be used to impose a distance and/or angle between sleeves to achieve distraction or compression of vertebrae. Reduction of vertebrae may be achieved when an external frame is used to adjust a relative height of the sleeves.

Figure 81:
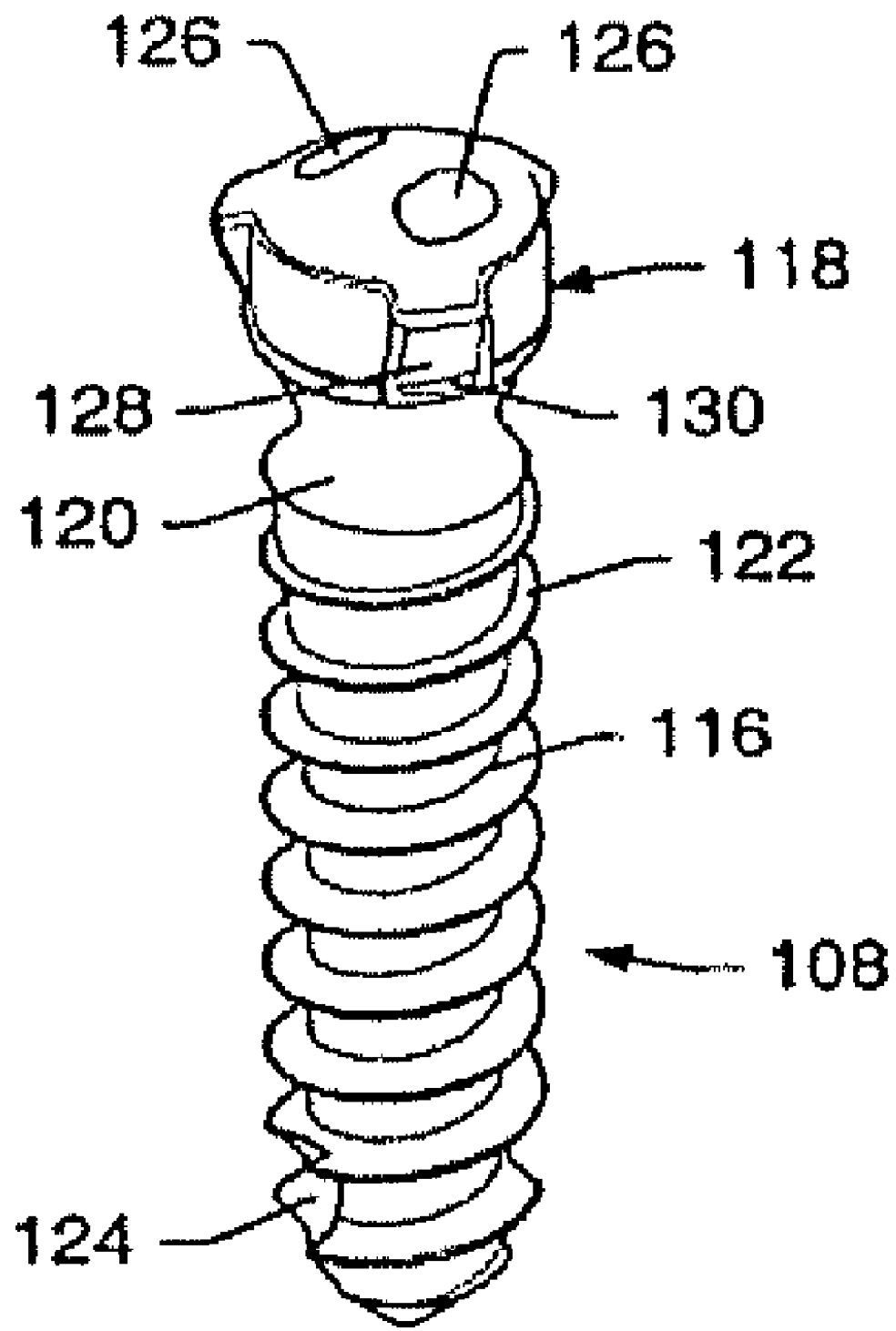
FIG. 81 depicts a perspective view of a bone fastener used in an invasive procedure.

In some embodiments, a spinal stabilization system may be inserted using an invasive procedure. Since insertion of a spinal stabilization system in an invasive procedure may be visualized, cannulated components (e.g., bone fasteners) and/or instruments (e.g., detachable members) may not be needed for the invasive (i.e., open) procedure. Thus, a bone fastener used in an invasive procedure may differ from a bone fastener used in a minimally invasive procedure. FIG. 81 depicts a perspective view of an embodiment of bone fastener 108 that may be used in an invasive procedure.

Bone fastener 108 may include shank 116, head 118, and neck 120. Shank 116 may include threading 122. In some embodiments, threading 122 may include self-tapping start 124. Self-tapping start 124 may facilitate insertion of bone fastener 108 into vertebral bone. Head 118 of bone fastener 108 may include various configurations to engage a driver that inserts the bone fastener into a vertebra. In certain embodiments, the driver may also be used to remove an installed bone fastener from a vertebra.

In some embodiments, head 118 may include one or more tool portions 126. Tool portions 126 may be recesses and/or protrusions designed to engage a portion of the driver. Driver 380 depicted in FIG. 77 may be used to engage bone fastener 108 with tool portions 126 as depicted in FIG. 81. Head 118 of bone fastener 108 may include one or more splines. In some embodiments, bone fastener 108 may be used with a collar, a ring, and/or a closure member described for use with a cannulated bone fastener. In certain embodiments, bone fasteners with closed collars may be used in an invasive spinal stabilization procedure. In certain embodiments, fixed bone fasteners (e.g., open fixed bone fasteners) may be used in an invasive spinal stabilization procedure.

In some embodiments, tools used in an invasive procedure may be similar to tools used in a minimally invasive procedure. In certain embodiments, methods of installing a spinal stabilization system in an invasive procedure may be similar to methods of installing a spinal stabilization system in a minimally invasive procedure.

Recently, it has become increasingly popular to insert spinal fixation rods percutaneously. One existing system is a sextant or tripod that delivers a fixation rod via a fixed trajectory along a fixed arc (i.e., such systems have a fixed pivot point). One problem with such systems is that they require an additional incision be made in the patient for insertion of the rod. Furthermore, for multi-level procedures or longer rods, the additional incision must be relatively far away from the surgical site. This requires the rod to be pushed a relatively long distance through tissue until reaching the fixation site. Another problem is that such systems do not easily accommodate procedures in which the spinal curvature does not easily align along an arc achievable by the sextant.

Figure 82:
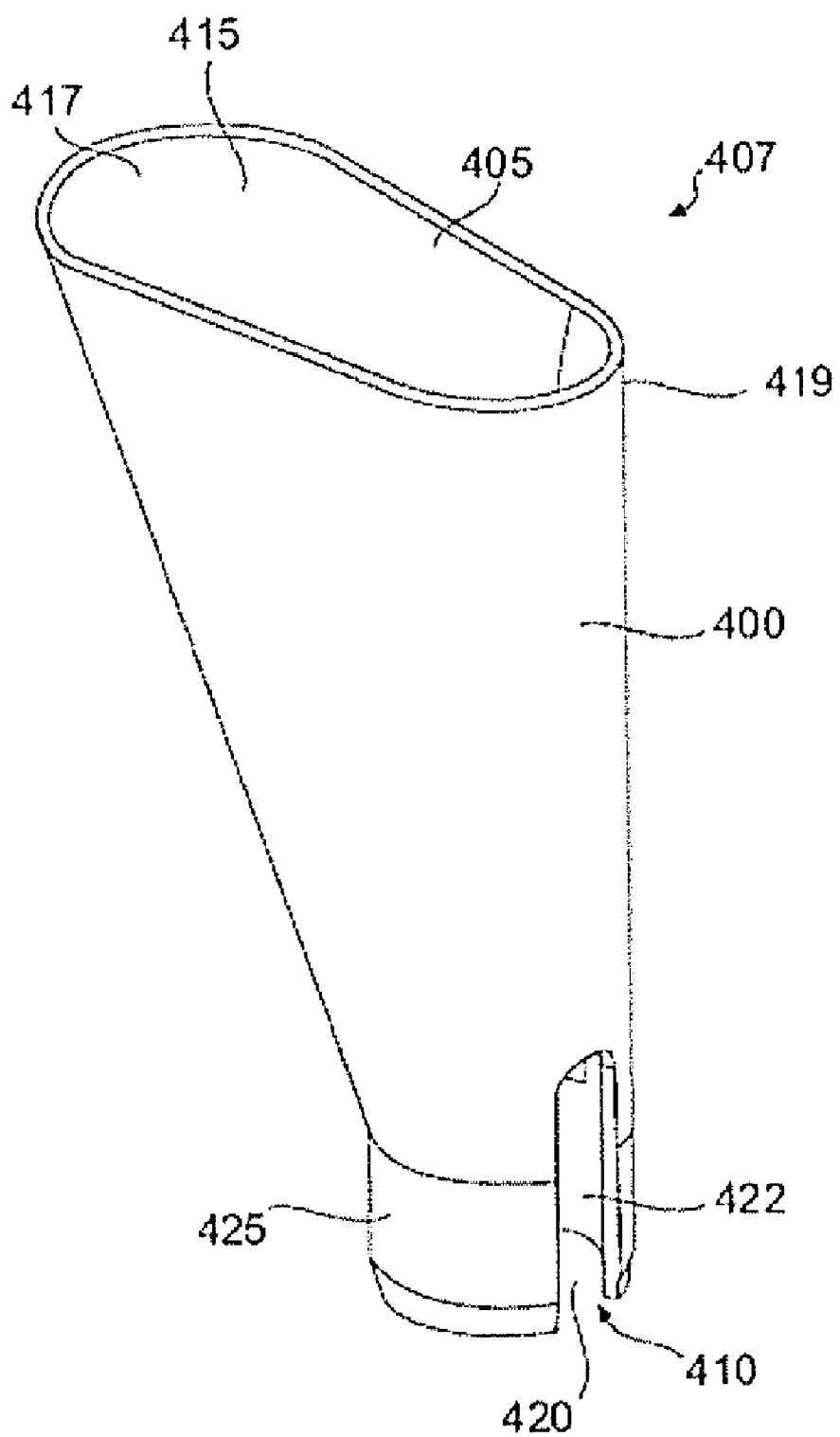
FIG. 82 is a diagrammatic representation of a view of one embodiment of a dilator.

FIG. 82 illustrates an embodiment of a dilator 400 to aid in percutaneous delivery of components for a spinal stabilization system without requiring a sextant. Dilator 400 can be formed of titanium, titanium alloys, stainless steel, ceramics, polyethersulfone, PEEK, polymers or other biocompatible material and can be formed as a single piece of material or as multiple pieces that are coupled together.

Dilator 400 can define a first opening 405 in a first end 407, a second opening 410 and a working channel 415 connecting first opening 405 and second opening 410. Working channel 415 can be at least partially defined by walls 417 and 419. According to an embodiment, dilator 400 can be shaped so that wall 419 is generally parallel with the sleeve during use, while wall 417 is angled relative to wall 419 or the sleeve. Dilator 400 can further be shaped such that first opening 405 opens at the surface or exterior to the surface of a patient during use and second opening 410 is positioned so that component of the spinal stabilization system, such as an elongated member, can pass through a sleeve (e.g., sleeve 244 of FIG. 48) and second opening 410. As will be discussed below, however, this orientation can be inverted and/or both opening 405 and 410 can be below the surface of the patient during use.

According to one embodiment, opening 410 can include a section 420 that at least partially overlaps an opening defined in a sleeve and collar assembly (such as openings 185, 187 or 189 shown in FIG. 48). Although shown as relatively short in FIG. 82, section 420 can extend a majority or all of the length of wall 419. Opening 410 can further include a section 422 with a size and shape such that a sleeve (such as sleeve 244 of FIG. 48) can fit through opening 410. When in use, the sleeve can pass through both opening 410 and opening 405. Sleeve receiving section 425 of dilator 400 can have a relatively constant cross section and size such that an inner surface of section 425 forms a frictional fit with the sleeve. The size of sleeve receiving section 425 can be selected so that a threshold amount of force is required to move dilator 400 relative to the sleeve. The inner surface of section 425 can be textured to increase friction. According to another embodiment, dilator 400 may be relatively loose even when the sleeve passes through dilator 400. While shown as having a constant shape, section 425 can have a variable size or shape.

While, in FIG. 82, opening 405 is shown has having curved ends with different radiuses of curvature and straight sides, opening 405 can have a variety of shapes including, but not limited to, an elongated opening of constant width, an elongated opening of variable width, a rectangular opening, a trapezoidal opening, a circular opening, a square opening, an ovoid opening, an egg-shaped opening, a tapered opening, and combinations and/or portions thereof. Similarly, opening 410 or the various sections of opening 410 can have a variety of shapes.

Figure 83:
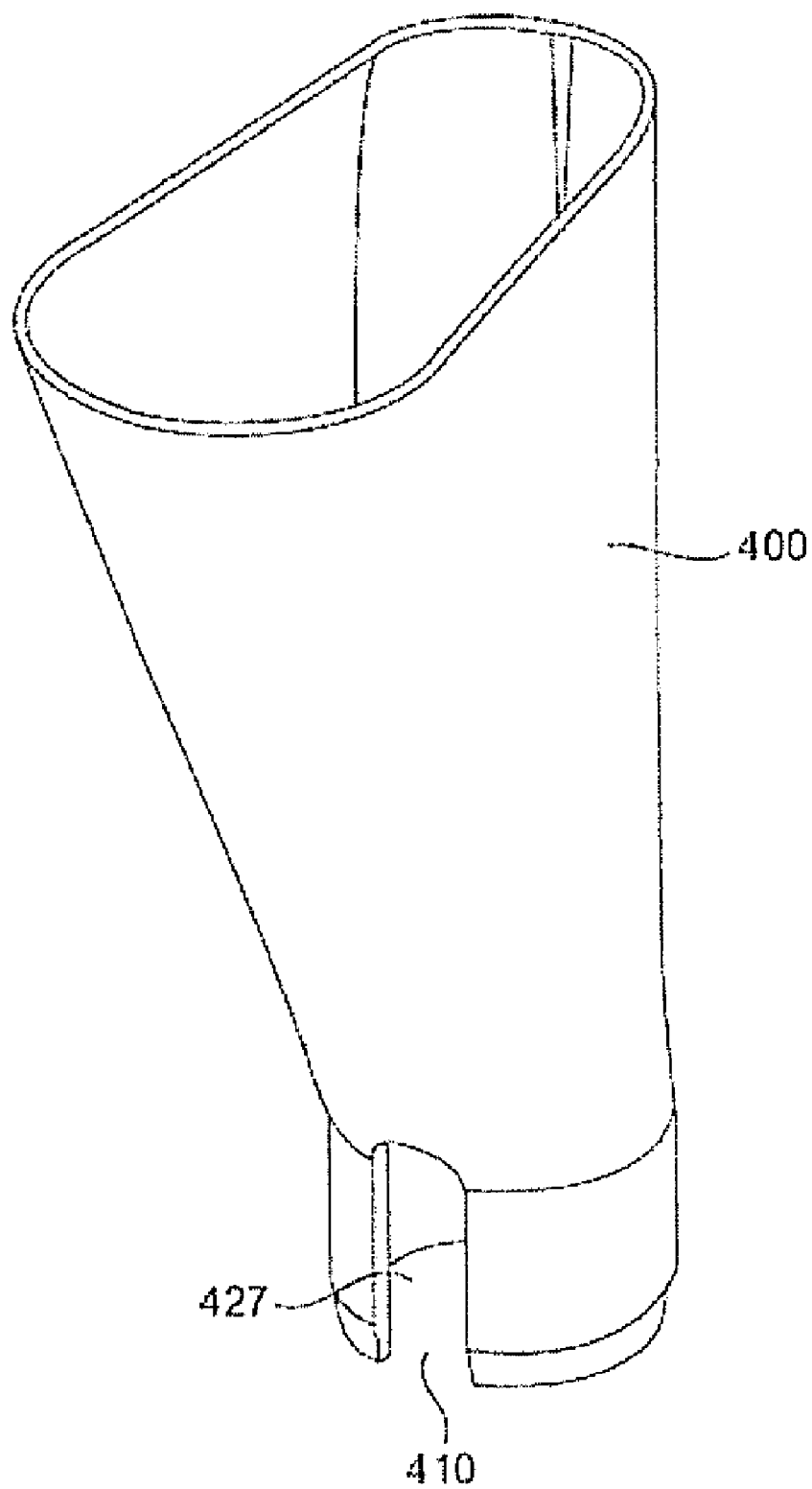
FIG. 83 is a diagrammatic representation of another view of an embodiment of a dilator.

FIG. 83 illustrates another isometric view of dilator 400 showing that opening 410 can include another section 427. Section 427 can be aligned with section 420 (shown in FIG. 82). While shown as part of the same opening, section 427 can be a separate opening from sections 420 and 422 (shown in FIG. 82). Section 427 can provide space so that an elongated member to overhang a collar as discussed below.

Figure 84:
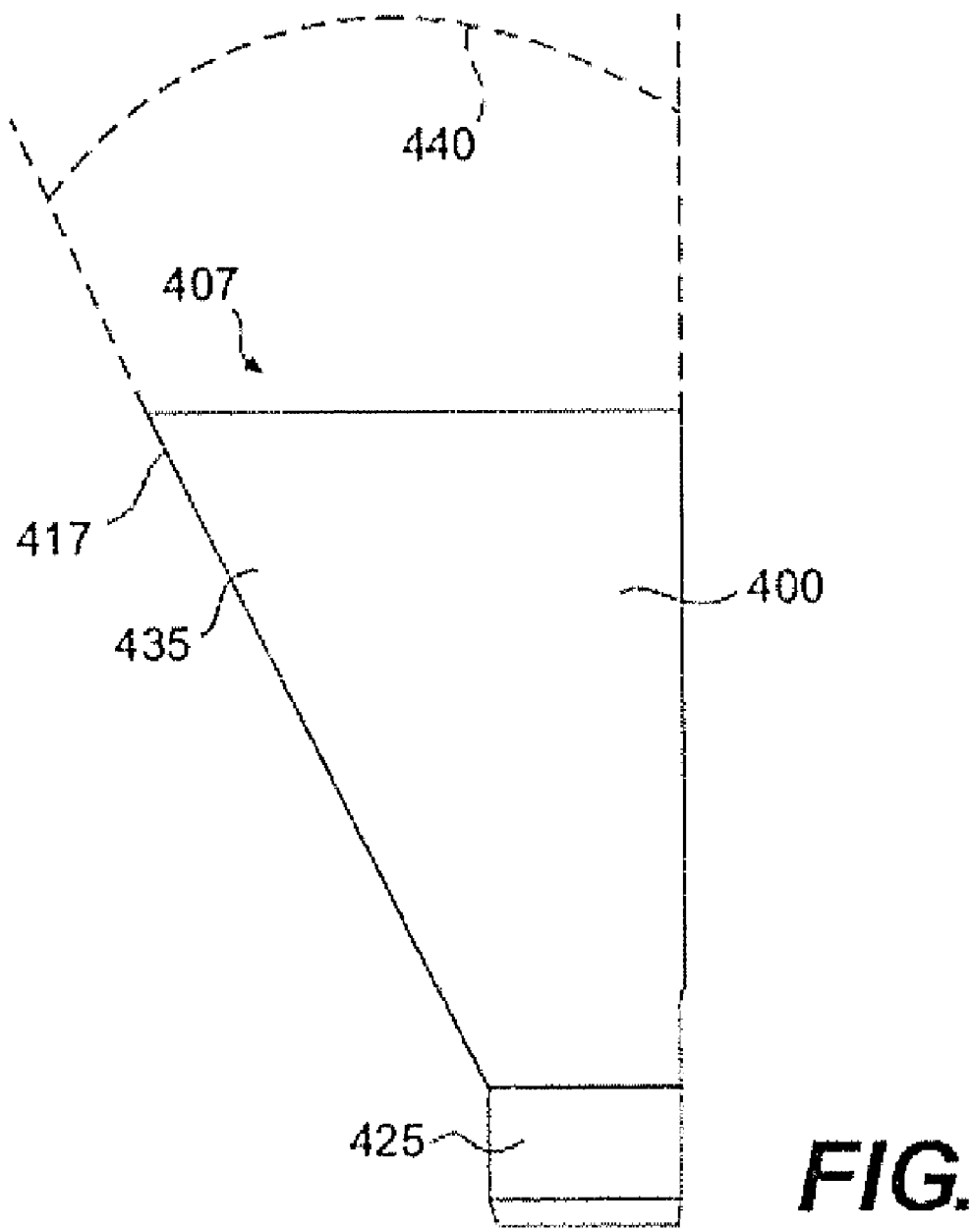
FIG. 84 is a diagrammatic representation of another view of an embodiment of a dilator.

FIG. 84 illustrates a side view of an embodiment of dilator 400. As shown in FIG. 84, dilator 400 can include a tapered section 435 with a wall 417 that slopes from end 407 to section 425. The angle of the taper, represented at 440, is preferably between 30 to 45 degrees, though larger or smaller angles may be used. Angle 440 determines, in part, the maximum amount tissue displaced by dilator 440. Additionally, angle 440 determines how far components being inserted through dilator 400 can be angled relative to a sleeve. In general, for a rigid component, angle 440 will be larger to accommodate angling of larger components. In other embodiments, section 435 may have a curved shape, a stair-stepped shape or other shape.

Figure 85:
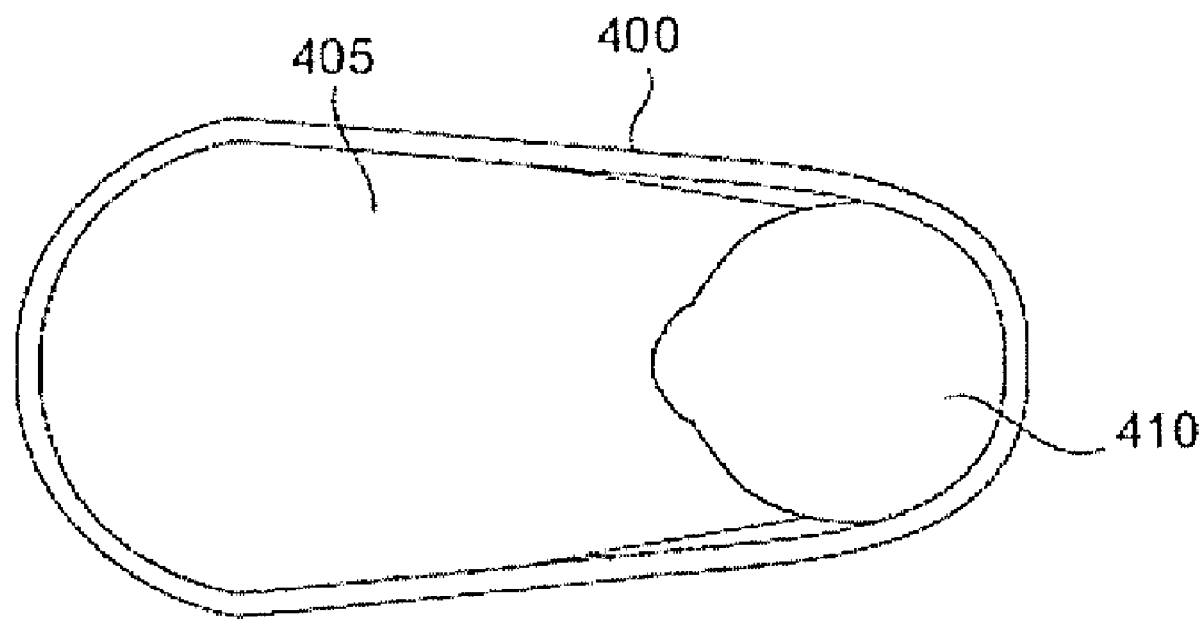
FIG. 85 is a diagrammatic representation of yet another view of an embodiment of a dilator.

FIG. 85 illustrates a top view dilator 400 showing opening 405 and opening 410. In the embodiment shown, opening 405 has a larger radius at one end than the other. The larger radius can provide more working area for inserting components. The opposite end can have a smaller radius to be closer in size to the sleeve. Opening 405 can have a variety of shapes including, but not limited to, an elongated opening of constant width, an elongated opening of variable width, a rectangular opening, a trapezoidal opening, a circular opening, a square opening, an ovoid opening, an egg-shaped opening, a tapered opening, and combinations and/or portions thereof.

Figure 86:
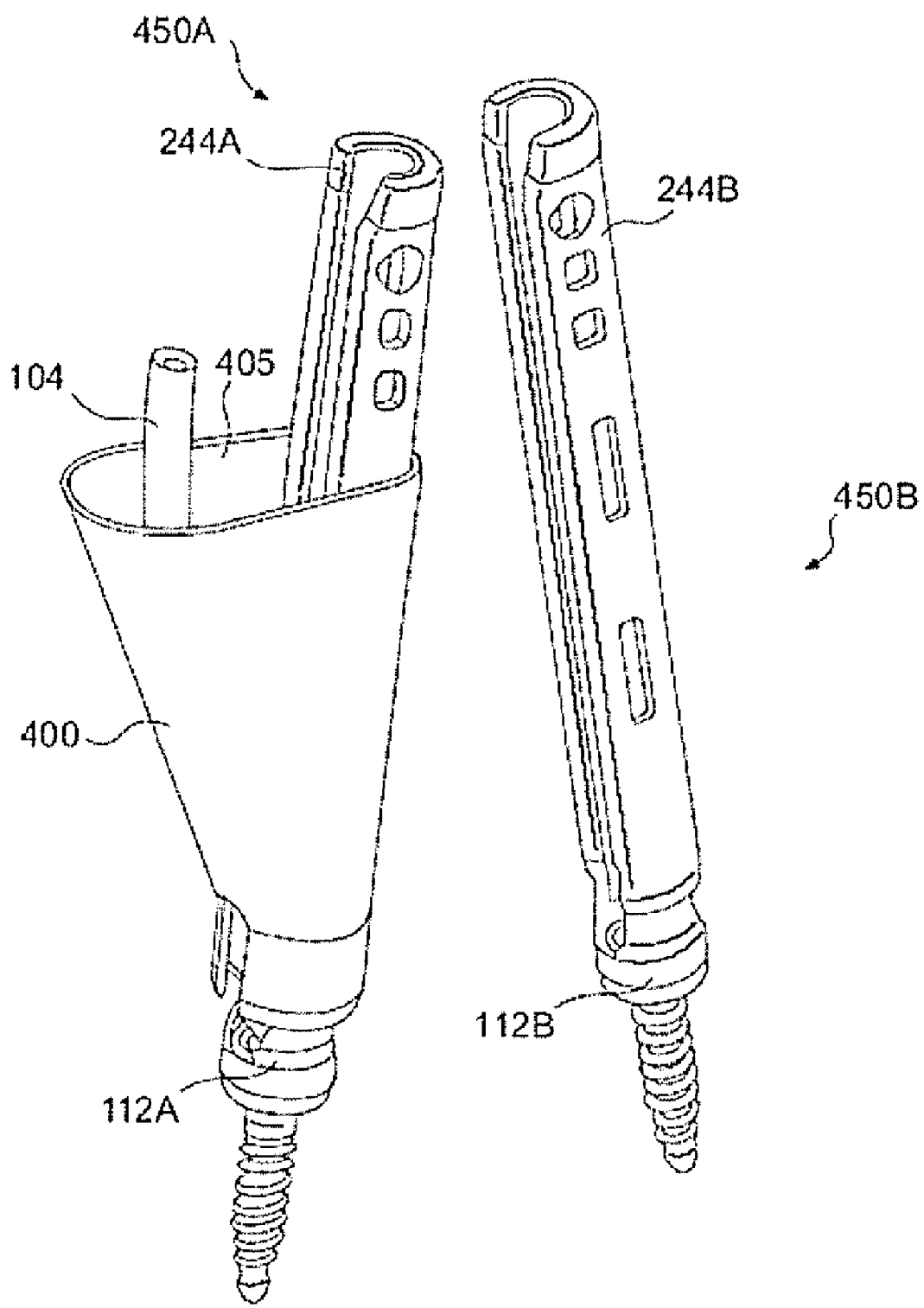
FIGS. 86-88 depict views of elongated member placement.
Figure 87:
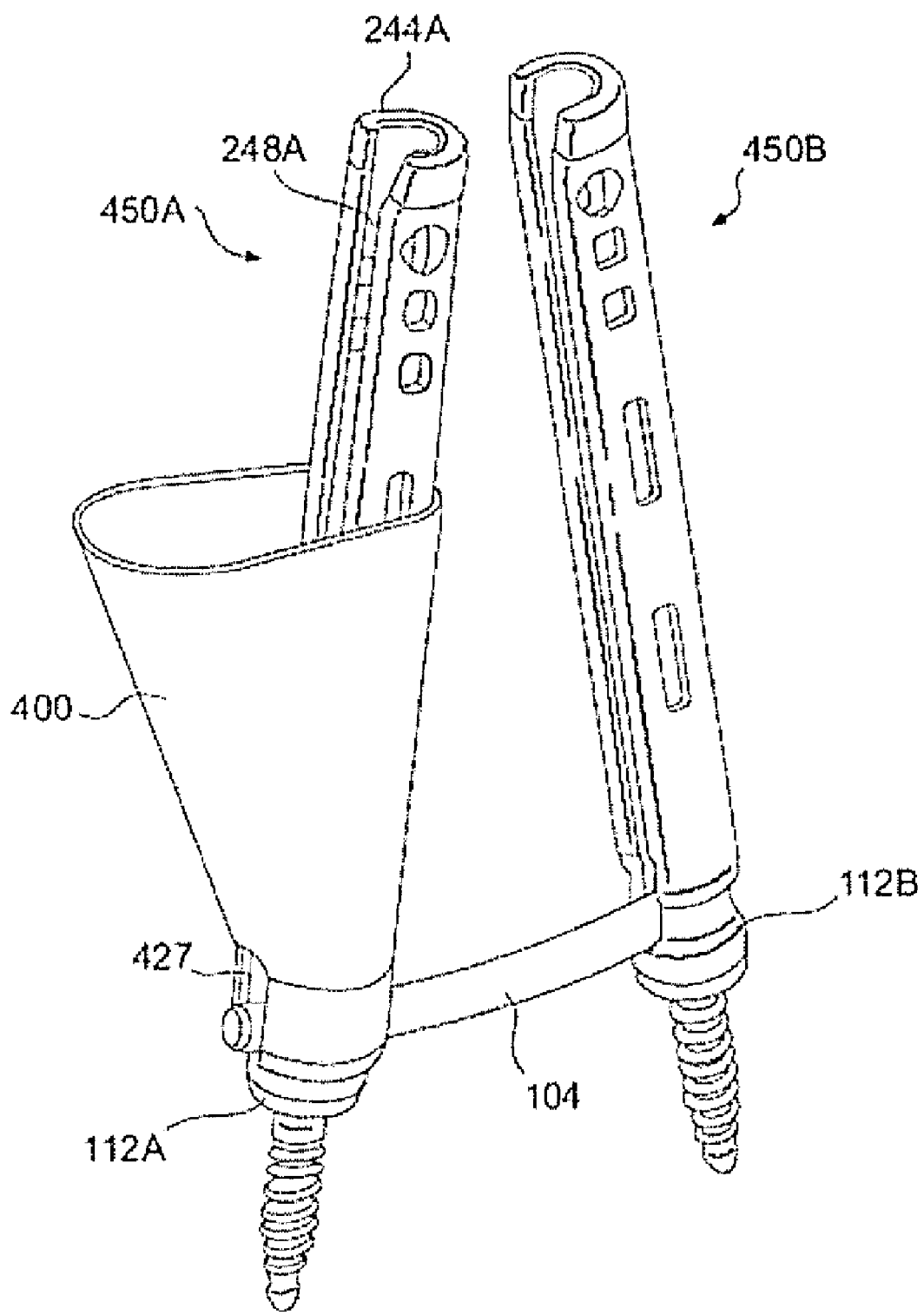
Figure 88:
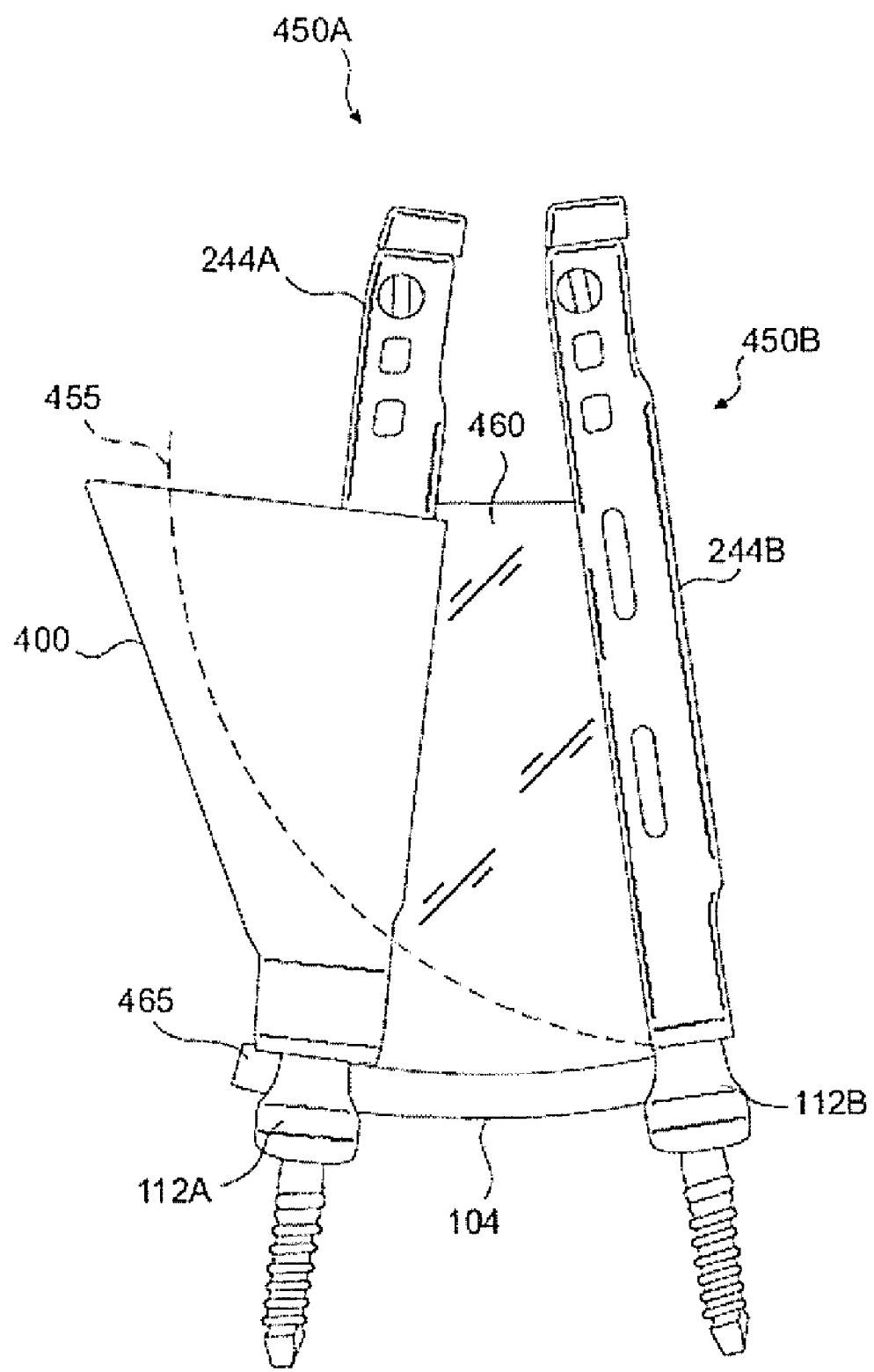

In operation, dilator 400 can be used to guide components from the exterior of the patient to a sleeve/collar assembly such that the component can be guided under tissue and muscle to another sleeve/collar assembly. FIGS. 86-88, for example, illustrate placement of an elongated member 104. Various surgical tools such as positioners can be used to position and move the elongated member 104. Referring to FIG. 86, sleeve 244A can be coupled to collar 112A to form assembly 450A and sleeve 244B can be coupled to collar 112B to form assembly 450B. When sleeve 244A is in place, dilator 400 can be placed over the top of sleeve 244A and moved down sleeve 244A into the patient. As dilator 400 moves, it can expand the incision through which sleeve 244A was inserted to displace tissue and muscle proximate to sleeve 244A. Embodiments of sleeve 244A and/or dilator 400 can include a shoulder, stop, taper, complementary features or other features that aid in placement of dilator 400 (i.e., to prevent dilator 400 from being inserted too deeply). Thus, dilator 400 can be positioned in the same incision as one of the sleeves, obviating the need for additional incisions.

Elongated member 104 can be manipulated so that a first portion of elongated member 104 enters dilator 400 through opening 405, passes through a first side of assembly 450A, out the obverse side of assembly 450A and out opening 410 (illustrated in FIG. 82) of dilator 400. For example, the first portion of elongated member 104 can enter sleeve 244A at opening 187 (shown in FIG. 48), exit sleeve 244A at opening 185 (shown in FIG. 48) and exit dilator 400 through section 420 of opening 410 (shown in FIG. 82). Elongated member 104 can be moved such that the first portion of the elongated member enters assembly 450B (e.g., such as through opening 185 of assembly shown in FIG. 48). Preferably, elongated member 104 moves along a path beneath the tissue and muscle disposed between sleeves 244A and 244B until in position Referring to FIG. 87, elongated member 104 is shown seated in collar 112A and 112B. The first portion of elongated member 104 can rest in collar 112B and the second portion in collar 112A as previously described. Dilator 400 can be removed before or after securing elongated member 104. Section 427 allows elongated member 104 to overhang collar 12A.

in the embodiment of FIG. 87, sleeve 244A is positioned so that channel 248A faces into dilator 400. Thus, the end of elongated member 104 can enter assembly 450A at any point along the length of sleeve 244A. Orienting channel 248A as shown may be advantageous as it may make it easier to align the end of elongated member 104 with the opening to assembly 450A. Furthermore, it is advantageous from a manufacturability and ease of use standpoint to use the same type of sleeves for percutaneous placement of elongated members as are used in other procedures. However, any type of sleeve that couples to a collar of a bone fastener assembly may be used. Furthermore, the orientation of sleeve 244A can be reversed so that the opening through which the end of elongated member 104 enters assembly 450A is relatively short. Additionally, a sleeve can be used in which channel 248A does not extend a majority of the length of sleeve 244A, but is relatively short such the opening through which elongated member 104 enters assembly 450A is smaller and may, in some embodiments, only include a portion of the slot of collar 112A.

FIG. 88 illustrates a side view of elongated member 104 in place in collar 112A and 112B of assemblies 450A and 450B respectively. FIG. 88 further illustrates an insertion path (represented by dashed line 455) for elongated member 104. According to the embodiment of FIG. 88, elongated member 104 is enters dilator 400 through opening 405 (shown in FIG. 82). One end of elongated member 104 passes through assembly 450A and exits dilator 400 through section 422 of opening 410 (shown in FIG. 82). That end is guided or otherwise moved through or under tissue 460 to collar 112B of assembly 450B. The other end 465 of elongated member 104 can exit dilator 400 through opening 410 and be moved slightly backwards through section 427 (shown in FIG. 83) to overhang collar 112A. Because elongated member 104 passes under tissue 460, tissue 460 is saved retraction or other movement or trauma.

The shape of dilator 400 can be selected so that an elongated member of a selected size and curvature can be inserted percutaneously for a single or multi-level stabilization. Dilator 400, sleeve 244A and/or elongated member 104 can be radiolucent or contain markers that allow placement of dilator 400 and elongated member 104 to be viewed under medical imaging such fluoroscopy.

Because elongated member 104 passes through or under tissue 460 it may be desirable to shape one or both ends of elongated member 104 to ease passage of elongated member 104. For example, elongated member 104 can include rounded, beveled, tapered or otherwise shaped ends. Furthermore, elongated member 104 may pass through additional components of a spinal stabilization system, such as a multi-channel sleeve located between sleeve 244A and 244B for a multi-level stabilization procedure.

Elongated member 104 can be cannulated such that elongated member 104 can be led along a guide wire. In such an embodiment, a guide wire can first be run along insertion path 455 to assembly 450B. Elongated member 104 can then be placed by guiding elongated member 104 using the guide wire. In other embodiments, an end of elongated member 104 can be attached to a guide wire, such that elongated member 104 can be pulled to assembly 450B via the guide wire.

The use of dilator 400 presents several advantages over other percutaneous delivery systems. First, some percutaneous delivery systems require an additional incision to be made so that a spinal rod can be guided at a shallow angle to fasteners. Dilator 400, conversely, can dilate the existing incision used to insert a sleeve, thereby decreasing the need for extra incisions. Additionally, some percutaneous delivery systems use a tripod or sextant like structure that have a fixed pivot point. For larger or multi-level stabilizations, this requires that the incision through which the rod enters the body be further away from the portion of the spine being stabilized. Consequently, the rod must be pushed a relatively long distance through the body. With dilator 400, on the other hand, there is no fixed pivot point for elongated member 104. Consequently, the pivot angle of elongated member 104 can change as elongated member 104 is inserted into the body. For example, the pivot angle can be greater when elongated member 104 initially enters the body from the dilator. This provides the advantage that an elongated member can be inserted closer to the area requiring stabilization.

Figure 89:
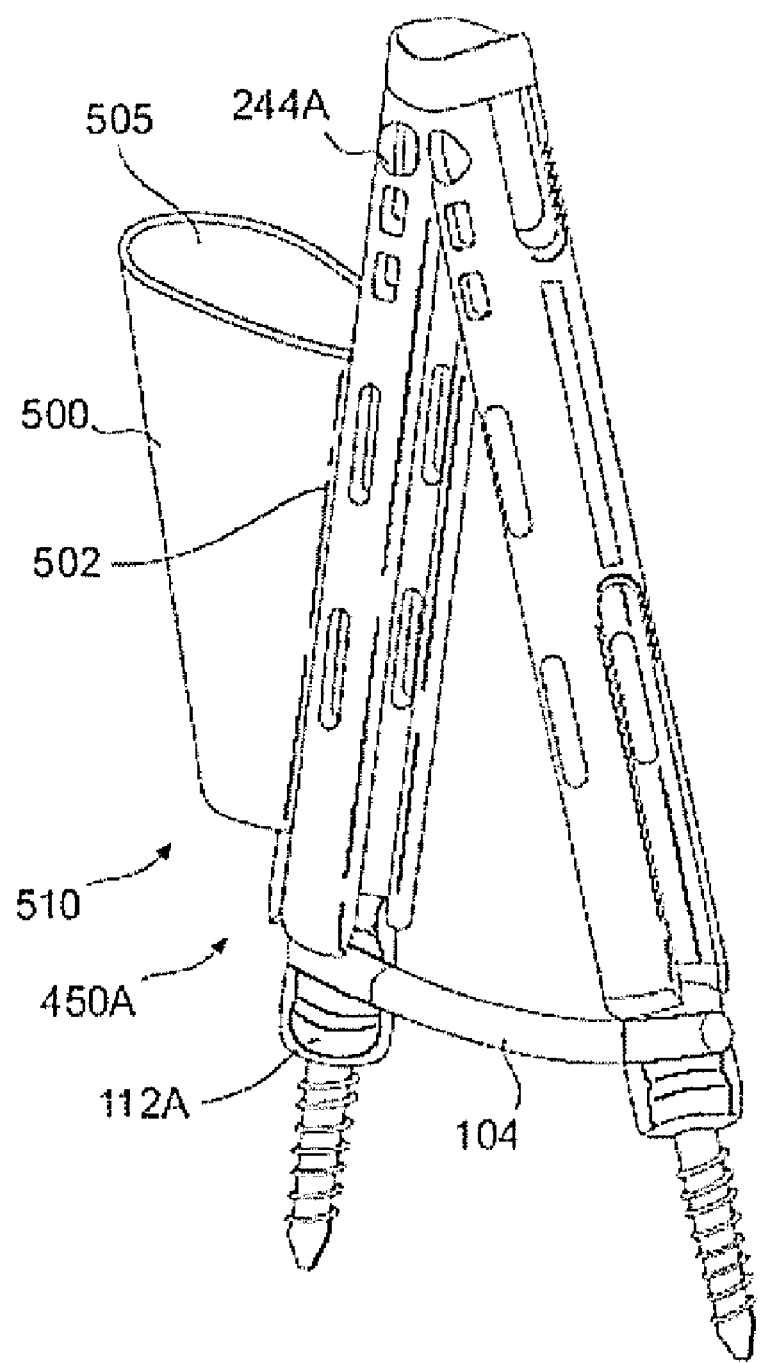
FIG. 89 is a diagrammatic representation of another embodiment of a dilator.

In the previous embodiments, dilator 400 is shaped such that sleeve 244A (or other sleeve) passes through dilator 400. FIG. 89, on the other hand, illustrates an embodiment of a dilator 500 in which dilator 500 does not attach to sleeve 244A, but instead rests against the sleeve 244A. According to an embodiment, dilator 500 can include a concave wall 502 to abut sleeve 244A. The tension of skin and tissue around dilator 500 may be sufficient to hold dilator 500 in place against sleeve 244A.

Dilator 500 can include an opening 505 through which an elongated member 104 enter dilator 500 and an opening 510 through which elongated member 104 exits dilator 500. Opening 510 can be defined in the bottom and/or side of dilator 500. Dilator 600 can be positioned and shaped such that elongated member is guided to an entrance in sleeve 244A (or an assembly of sleeve 244A and a collar 112A such as shown in FIG. 48) proximate to opening 510. In this example, the end of elongated member 104 exits dilator 500 prior to entering assembly 450A.

As described above, dilator 500 can be held in place by the force of skin and tissue surrounding dilator 500. In another embodiment, dilator 500 can include features to mate with sleeve 244A to inhibit movement. For example, dilator 500 can include a "T", "L" or otherwise shaped extension extending from a portion of wall 502 that fits in a complementary portion of the sleeve, such as a channel (e.g., channel 248 shown in FIG. 49), to form a tongue and groove connection between dilator 500 and sleeve 244A. Dilator 500 can include other suitable coupling mechanisms.

Figure 90:
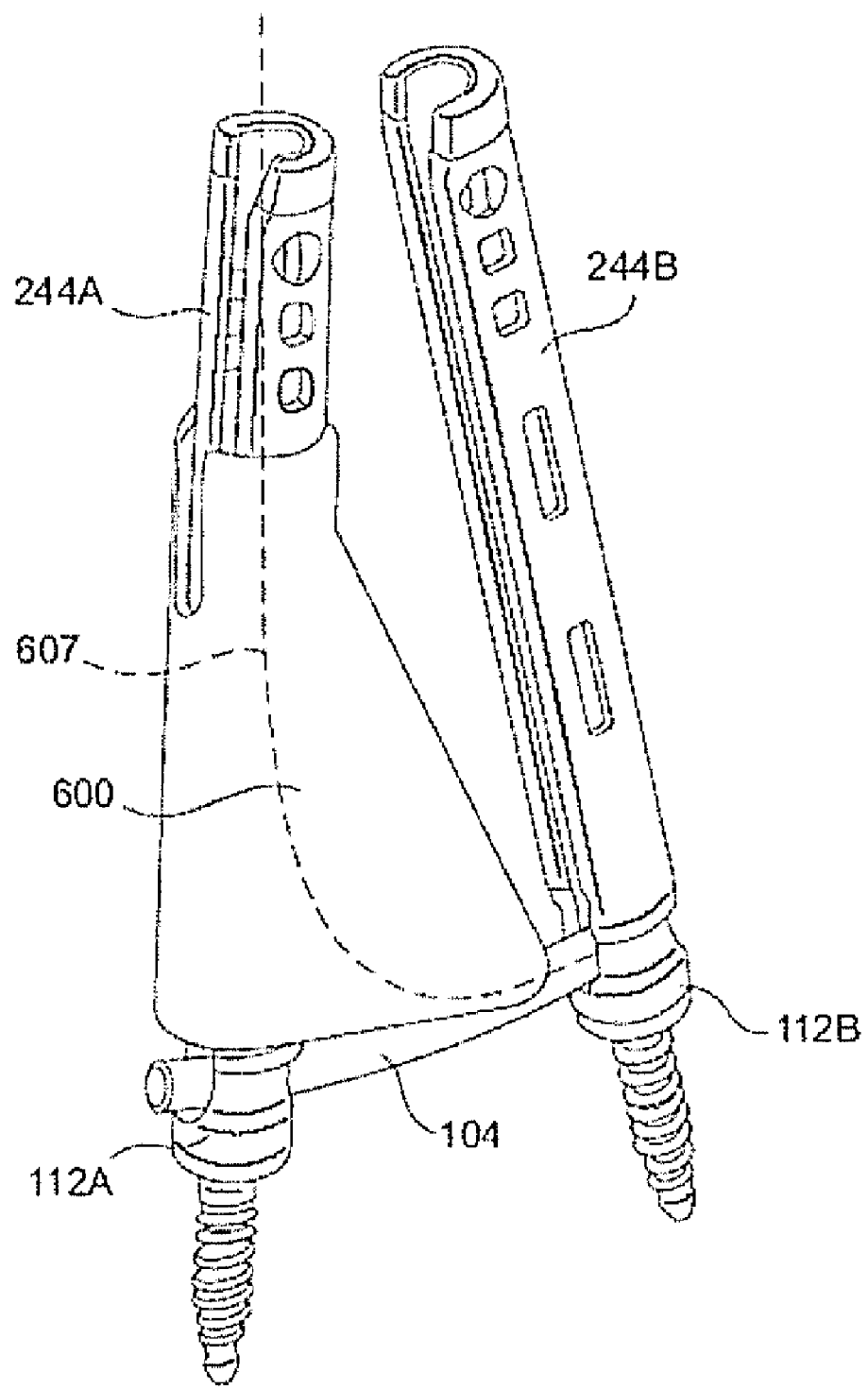
FIG. 90 is a diagrammatic representation of an embodiment of a dilator in another orientation.

FIG. 90 depicts an embodiment in which a dilator 600 is inverted on a sleeve 244A such that dilator 600 displaces material between sleeve 244A and sleeve 244B. An example path for inserting elongated member 104 is represented by dashed line 607. In this example, elongated member 104 can initially be inserted into sleeve 244A. At least a portion of elongated member 104 exits sleeve 244A into the working channel created by dilator 400. Elongated member 104 can then be guided to collars 112A and 112B. Thus, in this example, elongated member enters the body through sleeve 244A.

One advantage of displacing tissue between sleeves 244A and 244B is that elongated member 104 potentially does not have to displace any tissue. Additionally, this allows for more working room around the collars 112A and 112B where elongated member 104 is being positioned.

While, in the embodiment shown, dilator 600 is shown as being similar to dilator 400 of FIG. 82, dilator 600, in other embodiments, can be collapsible. According to an embodiment, dilator 600 can be deployed in one or more steps. For example, in the first step, dilator 600 can be placed over sleeve 244A in a collapsed, tube-like configuration. In the second step, a tool can be inserted into sleeve 244A to actuate dilator 600 and expand dilator 600 to move muscle and tissue. Dilator 600 can include any suitable expansion mechanism. For example, dilator 600 can include multiple rigid spokes that can pivot outwards and a resilient material disposed between the spokes. In this embodiment, dilator 600 acts in an umbrella or fan like manner to open. In another embodiment, dilator 600 can include a set of interlocking plates that slide relative to each other to open. Dilator 600 can include any other suitable collapsing mechanism.

Figure 91:
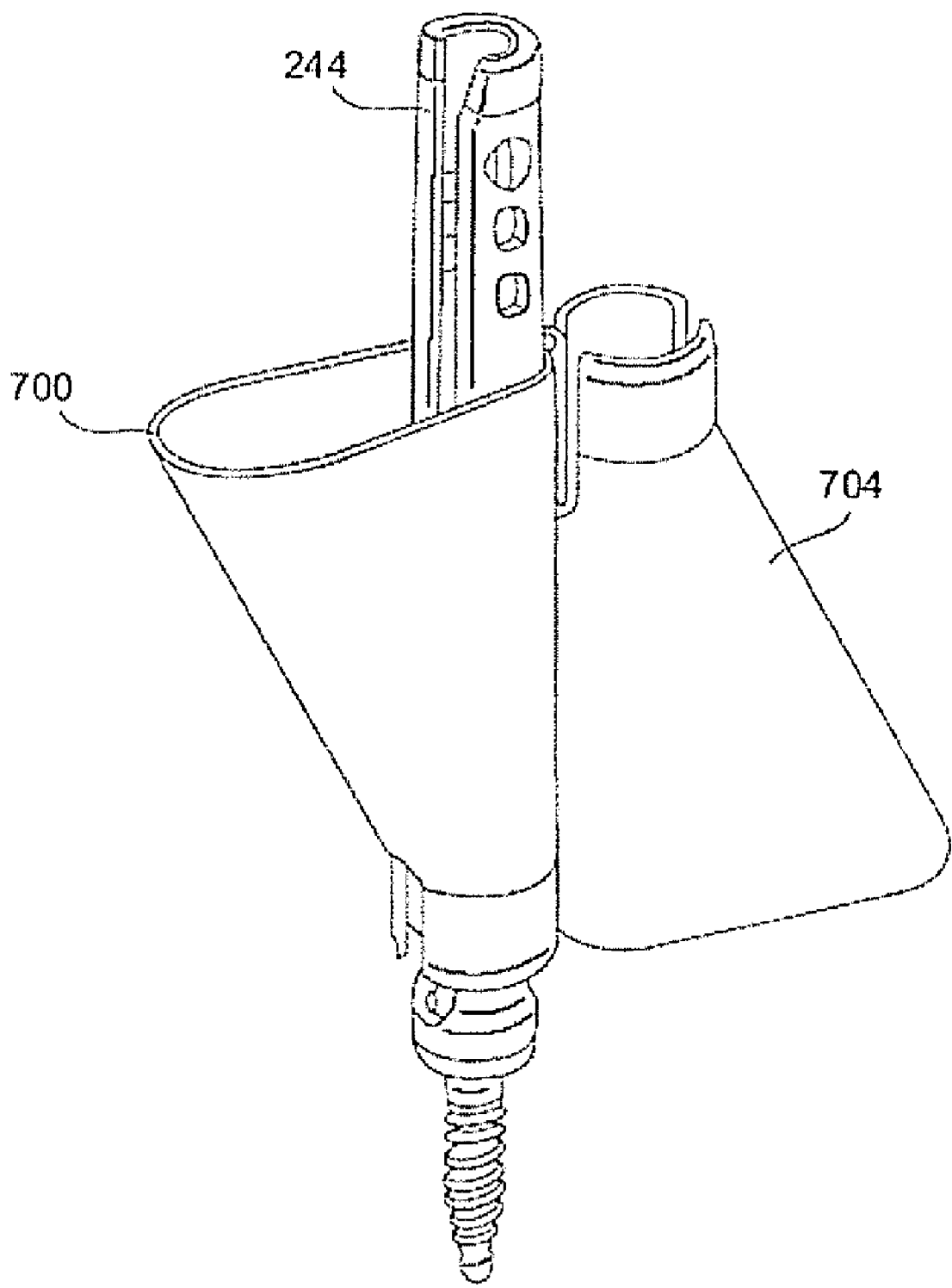
FIG. 91 is a diagrammatic representation of an embodiment of multiple dilators.

According to an embodiment, multiple dilators can be used in conjunction with each other. FIG. 91, for example, depicts a dilator 700 coupled to sleeve 244 and dilator 704 rest against dilator 700 and sleeve 244. In this embodiment, dilators 700 and 704 are in inverted configurations from each other. Dilator 700 can provide a working space that allows an elongated member to be inserted percutaneously while dilator 704 maintains a clear workspace about the collars. The dilators may be of similar design or may be different. In FIG. 91, for example, dilator 700 couples to sleeve 244 via a frictional fit while dilator 704 relies on tissue tension to remain in place against dilator 700 and sleeve 244.

Further modifications and alternative embodiments will be apparent to those skilled in the art in view of this description. Accordingly, this description is to be construed as illustrative only and is for the purpose of teaching those skilled in the art the general manner of carrying out the teachings of the disclosure. It is to be understood that the embodiments shown and described herein are to be taken as the presently preferred embodiments. Elements and materials may be substituted for those illustrated and described herein, parts and processes may be reversed, and certain features may be utilized independently, all as would be apparent to one skilled in the art after having the benefit of this disclosure. Changes may be made in the elements described herein without departing from the spirit and scope of the following claims

What is claimed is:

1. A spinal stabilization surgical method comprising:
    forming an incision at a desired site through skin of a patient;
    forming a first assembly, the first assembly comprising:
        a first bone fastener;
        a first collar coupled to the first bone fastener; and
        a first sleeve removably coupled to the first collar;
        wherein the first bone fastener is fastened to a first vertebra, wherein the first sleeve extends through the incision when the first bone fastener is fastened to the first vertebra;
    forming a second assembly, the second assembly comprising:
        a second bone fastener;
        a second collar coupled to the second bone fastener; and
        a second sleeve removably coupled to the second collar;
    positioning the first assembly in the incision;
    positioning a dilator in the incision to displace tissue proximate to the first sleeve, wherein the dilator is positioned so that more tissue is displaced on a first side of the first sleeve than on a second side of the first sleeve, wherein positioning the dilator in the incision includes placing the dilator over the first sleeve and moving the dilator along the first sleeve into the incision, wherein the dilator comprises:
        a first opening a first diameter;
        a second opening having a second diameter that is different than the first diameter; and
        a working channel running from the first opening to the second opening;
    moving at least a first portion of an elongated member into the working channel;
    moving the first portion of the elongated member to the second assembly;

seating the first portion of the elongated member in the second collar; and seating a second portion of the elongated member in the first collar.

2. The method of claim 1, wherein the elongated member enters the working channel through the first opening and exterior to the first sleeve.

3. The method of claim 1, wherein the positioning the dilator further comprises positioning the dilator so that at least a majority of the tissue displaced is on the opposite side of the first sleeve from the second sleeve.

4. The method of claim 1, further comprising moving the first portion of the elongated member into the dilator through the first opening, through the first assembly and out the dilator through the second opening prior to moving the first portion of the elongated member to the second assembly.

5. The method of claim 4, wherein the first portion of the elongated member passes through the first assembly prior to exiting the dilator.

6. The method of claim 4, wherein the first portion of the elongated member exits the dilator prior to passing through the first assembly.

7. The method of claim 1, further comprising guiding the elongated member through a third assembly coupled to a third vertebra between the first and second vertebrae.

8. The method of claim 1, wherein guiding the first portion of the elongated member to the second assembly further comprises percutaneously moving the first portion of the elongated member to the second assembly.

9. The method of claim 1, wherein positioning the dilator further comprises positioning the dilator such that at least a portion of the first sleeve passes through the dilator.

10. The method of claim 1, wherein the second bone fastener is fastened to a second vertebra, wherein the second sleeve extends through the incision when the second bone fastener is fastened to the second vertebra.

11. A spinal stabilization surgical method comprising:
   forming a first assembly, the first assembly comprising:
      a first bone fastener;
      a first collar; and
      a first sleeve;
      wherein the first bone fastener is fastened to a first vertebra;
   forming a second assembly, the second assembly comprising:
      a second bone fastener;
      a second collar; and
      a second sleeve;
   positioning a dilator in an incision through which the first assembly enters a patient to displace tissue proximate to the first sleeve, wherein the dilator comprises:
      a first opening;
      a second opening; and
      a working channel running from the first opening to the second opening;
   moving at least a first portion of an elongated member into the working channel;
   moving the first portion of the elongated member to the second assembly;
   seating the first portion of the elongated member in the second collar;
   seating a second portion of the elongated member in the first collar; and
   moving the first portion of the elongated member through a portion of the first sleeve prior to the first portion of the elongated member entering the dilator.

12. A spinal stabilization surgical method comprising:
   forming an incision at a desired site through skin of a patient;
   forming a first assembly, the first assembly comprising:
      a first bone fastener;
      a first collar coupled to the first bone fastener; and
      a first sleeve removably coupled to the first collar;
      wherein when the first bone fastener is fastened to a first vertebra, the first sleeve extends through the incision;
   forming a second assembly, the second assembly comprising:
      a second bone fastener;
      a second collar coupled to the second bone fastener; and
      a second sleeve removably coupled to the second collar;
      wherein when the second bone fastener is fastened to a second vertebra, the second sleeve extends outside of the patient;
   positioning a dilator in the incision through which the first assembly enters the patient to displace tissue proximate to the first sleeve, wherein the dilator comprises:
      a first opening having a first diameter;
      a second opening having a second diameter, the second diameter being different than the first diameter;
      a working channel running from the first opening to the second opening;
      a first wall approximately parallel to the first sleeve; and
      a second wall at an angle relative to the first wall, wherein the first wall and the second wall at least partially define the working channel;
   moving at least a first portion of an elongated member into the working channel;
   moving the first portion of the elongated member to the second assembly;
   seating the first portion of the elongated member in the second collar; and
   seating a second portion of the elongated member in the first collar.

13. The method of claim 12, wherein the dilator further comprises a first sleeve receiving section shaped to receive the first sleeve and form a frictional fit with the first sleeve.

14. The method of claim 13, wherein the first sleeve receiving section has an approximately constant cross section.

15. The method of claim 12, wherein the second opening comprises a section approximately parallel to the first opening.

16. The method of claim 12, wherein the dilator is positioned such that the first opening is exterior to the patient and the second opening is proximate to the first collar.

17. The method of claim 12, wherein the second opening comprises a section approximately perpendicular to the first opening.

18. The method of claim 17, wherein positioning further comprises positioning the dilator so that the section of the second opening at least partially overlaps an opening in the first assembly.

19. The method of claim 18, wherein the second opening comprises a second section perpendicular to the first opening and wherein the elongated member overhangs the first collar through the second section when the second portion of the elongated member is seated in the first collar.

20. The method of claim 12, wherein the first opening has a smaller radius of curvature proximate to the first wall than the second wall.

21. The method of claim 12, wherein the second wall is at an angle of approximately 30-45 degrees from the first wall.

22. The method of claim 12, further comprising:
   securing the second portion of the elongated member to the first collar with a first closure member; and
   securing the first portion of the elongated member to the second collar with a second closure member.

* * * * *